United States Patent
Kehne et al.

(10) Patent No.: US 6,228,808 B1
(45) Date of Patent: May 8, 2001

(54) CARBAMOYLPHENYLSULFONYLUREAS, PROCESSES FOR THEIR PREPARATION AND THEIR USE AS HERBICIDES AND PLANT GROWTH REGULATORS

(75) Inventors: Heinz Kehne; Lothar Willms, both of Hofheim; Christian Waldraff, Frankfurt; Hansjörg Dietrich, Kriftel; Hermann Bieringer, Eppstein; Christopher Rosinger, Hofheim; Thomas Auler, Kelsterbach, all of (DE)

(73) Assignee: Hoechst Schering AgrEvo GmbH, Berlin (DE)

( * ) Notice: Subject to any disclaimer, the term of this patent is extended or adjusted under 35 U.S.C. 154(b) by 0 days.

(21) Appl. No.: 09/182,763

(22) Filed: Oct. 30, 1998

(30) Foreign Application Priority Data

Nov. 3, 1997 (DE) .............................. 197 48 470

(51) Int. Cl.$^7$ ...................... A01N 43/54; C07D 239/48; C07D 239/69
(52) U.S. Cl. ..................... 504/239; 504/242; 504/243; 544/319; 544/321
(58) Field of Search ................... 544/319, 321; 504/239, 242, 243

(56) References Cited

U.S. PATENT DOCUMENTS

| | | | |
|---|---|---|---|
| 4,302,241 | * 11/1981 | Levitt et al. | 544/321 |
| 4,521,597 | * 6/1985 | Kristinsson et al. | 544/321 |
| 5,104,440 | * 4/1992 | Meyer et al. | 544/321 |
| 5,385,923 | * 1/1995 | Latimer et al. | 548/211 |
| 5,886,176 | * 3/1999 | Muller | 544/321 |

\* cited by examiner

Primary Examiner—Richard L. Raymond
Assistant Examiner—Venkataraman Balasubramanian

(74) Attorney, Agent, or Firm—Frommer Lawrence & Haug LLP

(57) ABSTRACT

Compounds of the formula (I) or salts thereof

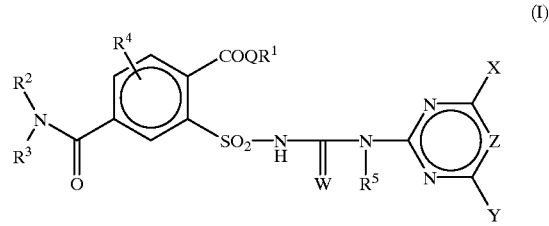

in which $R^1$, $R^3$=H, (subst.) hydrocarbon radical (HC) or (subst.) heterocyclyl which, including substituents, have 1–30 carbon atoms, $R^2 = R^0 - Q^0 -$, in which $R^0$=H, (subst.) HC or (subst.) heterocyclyl radical, in each case having 1–30 carbon atoms including substituents, and $Q^0$=a direct bond or $-O-$, $-SO_2-$, $-NH-$, $-N[(C_1-C_6) \text{alkyl}]-$, $-CO-$, $-CO-NH-$ or $-O-CO-NH-$; $R^4$=H, halogen, $NO_2$, CN, $(C_1-C_4)$alkyl, $(C_1-C_4)$alkoxy, $[(C_1-C_4)\text{alkyl}]$carbonyl or $[(C_1-C_4)\text{alkoxy}]$carbonyl, where each of the last four radicals may be halogenated; $R^5$=H or $(C_1-C_4)$alkyl; Q=O or NR*; R*=H. $(C_1-C_4)$alkyl, $(C_3-C_4)$alkenyl or $(C_3-C_4)$alkynyl, where each of the last three radicals may be substituted by halogen, $(C_1-C_4)$alkoxy and/or $(C_1-C_4)$alkylthio, W=O or S; X,Y=H, halogen, $(C_1-C_4)$alkyl, $(C_1-C_4)$alkoxy, $(C_1-C_4)$alkylthio, where each of the last three radicals may be substituted by halogen, $(C_1-C_4)$alkoxy and/or $(C_1-C_4)$alkylthio, or mono- or di$[(C_1-C_4)\text{alkyl}]$amino, $(C_3-C_4)$cycloalkyl, $(C_2-C_5)$alkenyl, $(C_2-C_5)$alkynyl, $(C_2-C_5)$alkenyloxy or $(C_2-C_5)$alkynyloxy, Z=CH or N, are suitable as herbicides or plant growth regulators, for example for controlling harmful plants in crop plants, including transgenic crop plants. They can be prepared by processes according to claim 6, via intermediates, some of which are novel.

10 Claims, No Drawings

CARBAMOYLPHENYLSULFONYLUREAS, PROCESSES FOR THEIR PREPARATION AND THEIR USE AS HERBICIDES AND PLANT GROWTH REGULATORS

It is known that phenylsulfonylureas substituted by carbamoyl groups have herbicidal properties. These are symmetric derivatives of isophthalic acid (formula A; U.S. Pat. No. 4,302,241).

(A)

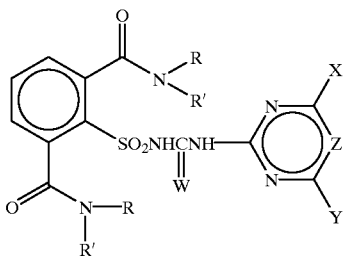

Surprisingly, we have now found terephthalic acid ester amides or diamides which are particularly suitable for use as herbicides or plant growth regulators.

The present invention provides compounds of the formula (I) or salts thereof (I)

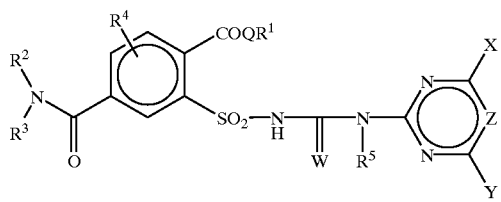

in which $R^1$ is a hydrogen atom, a hydrocarbon radical or a heterocyclyl radical, where each of the two last mentioned radicals is unsubstituted or substituted and has, including substituents, 1 to 30 carbon atoms, preferably 1 to 20 carbon atoms, $R^2$ is a group of the formula $R^0-Q^0-$, in which $R^0$ is a hydrogen atom, a hydrocarbon radical or a heterocyclyl radical, where each of the two last mentioned radicals is unsubstituted or substituted and has, including substituents, 1 to 30 carbon atoms, preferably 1 to 20 carbon atoms, and $Q^0$ is a direct bond or a divalent group of the formula —O—, —SO$_2$—, —NH—, —N[($C_1$–$C_6$)alkyl]-, —CO—, —CO—NH— or —O—CO—NH—, $R^3$ is a hydrogen atom, a hydrocarbon radical or a heterocyclyl radical, where each of the two last mentioned radicals is unsubstituted or substituted and has, including substituents, 1 to 30 carbon atoms, preferably 1 to 20 carbon atoms, $R^4$ is H, halogen, $NO_2$, CN, ($C_1$–$C_4$)alkyl, ($C_1$–$C_4$)alkoxy, [($C_1$–$C_4$)alkyl]-carbonyl or [($C_1$–$C_4$)alkoxy]carbonyl, where each of the four last mentioned radicals is unsubstituted or substituted in the alkyl moiety by one or more halogen atoms, $R^5$ is H or ($C_1$–$C_4$)alkyl, preferably H or $CH_3$, Q is O or NR*, R* is H, ($C_1$–$C_4$)alkyl, ($C_3$–$C_4$)alkenyl or ($C_3$–$C_4$) alkynyl, where each of the three last mentioned radicals is unsubstituted or substituted by one or more radicals selected from the group consisting of halogen, ($C_1$–$C_4$) alkoxy and ($C_1$–$C_4$)alkylthio, W is an oxygen or sulfur atom, X,Y independently of one another are H, halogen, ($C_1$–$C_4$)alkyl, ($C_1$–$C_4$)alkoxy, ($C_1$–$C_4$)alkylthio, where each of the three last mentioned radicals is unsubstituted or substituted by one or more radicals selected from the group consisting of halogen, ($C_1$–$C_4$)alkoxy and ($C_1$–$C_4$)alkylthio, or are mono- or di[($C_1$–$C_4$)alkyl] amino, ($C_3$–$C_4$)cycloalkyl, ($C_2$–$C_5$)alkenyl, ($C_2$–$C_5$) alkynyl, ($C_2$–$C_5$)alkenyloxy or ($C_2$–$C_5$)alkynyloxy and Z is CH or N.

The compounds of the formula (I) can form salts where the hydrogen of the —SO$_2$—NH— group is replaced by an agriculturally suitable cation. These salts are, for example, metal salts, in particular alkali metal salts or alkaline earth metal salts, in particular sodium salts and potassium salts, or else ammonium salts or salts with organic amines. Likewise, salt formation can be carried out by adding an acid to basic groups, such as, for example, amino and alkylamino. Suitable acids for this purpose are strong inorganic and organic acids, for example HCl, HBr, $H_2SO_4$ or $HNO_3$.

In the formula (I) and all formulae below, the carbon-containing radicals, such as alkyl, alkoxy, haloalkyl, haloalkoxy, alkylamino and alkylthio, and the corresponding unsaturated and/or substituted radicals, can in each case be straight-chain or branched in the carbon skeleton. Unless specifically stated otherwise, the lower carbon skeletons, for example having 1 to 6 carbon atoms, or in the case of unsaturated groups having 2 to 6 carbon atoms, are preferred for these radicals. Alkyl radicals, also in the composed meanings such as alkoxy, haloalkyl, etc., are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meaning of the unsaturated radicals which are possible and which correspond to the alkyl radicals; alkenyl denotes, for example, allyl, 1-methylprop-2-en-1-yl, 2-methylprop-2-en-1-yl, but-2-en-1-yl, but-3-en-1-yl, 1-methyl-but-3-en-1-yl and 1-methyl-but-2-en-1-yl; alkynyl is, for example, propargyl, but-2-in-1-yl, but-3-in-1-yl, 1-methyl-but-3-in-1-yl.

Alkenyl in the form "($C_3$–$C_4$)alkenyl" and "($C_3$–$C_6$) alkenyl" preferably denotes an alkenyl radical having 3 to 4 and 3 to 6 carbon atoms, respectively, where the double bond is not at the carbon atom which is linked to the remainder of the molecule of the compound (I) ("yl" position). This applies correspondingly to ($C_3$–$C_4$)alkynyl, etc.

Cycloalkyl is a carbocyclic saturated ring system having 3–8 carbon atoms, for example cyclopropyl, cyclobutyl, cyclopentyl or cyclohexyl.

Halogen is, for example, fluorine, chlorine, bromine or iodine. Haloalkyl, -alkenyl and -alkynyl are alkyl, alkenyl or alkynyl which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this applies correspondingly to haloalkenyl and other halogen-substituted radicals.

A hydrocarbon radical is a straight-chain, branched or cyclic and saturated or unsaturated aliphatic or aromatic hydrocarbon radical, for example alkyl, alkenyl, alkynyl, cycloalkyl, cycloalkenyl or aryl; aryl in this context is a mono-, bi- or polycyclic aromatic system, for example phenyl, naphthyl, tetrahydronaphthyl, indenyl, indanyl, pentalenyl, fluorenyl and the like, preferably phenyl; a hydrocarbon radical is preferably alkyl, alkenyl or alkynyl having up to 12 carbon atoms or cycloalkyl having 3, 4, 5, 6 or 7 ring atoms or phenyl.

A heterocyclic radical or ring (heterocyclyl) can be saturated, unsaturated or heteroaromatic; preferably, it contains one or more heteroatoms in the ring, preferably selected from the group consisting of N, O and S; it is preferably an aliphatic heterocyclyl radical having 3 to 7 ring atoms or a heteroaromatic radical having 5 or 6 ring atoms and contains 1, 2 or 3 heteroatoms. The heterocyclic radical can be, for example, a heteroaromatic radical or ring (heteroaryl), such as, for example, a mono-, bi- or polycyclic aromatic system in which at least one ring contains one or more heteroatoms, for example pyridyl, pyrimidinyl, pyridazinyl, pyrazinyl, triazinyl, thienyl, thiazolyl, oxazolyl, furyl, pyrrolyl, pyrazolyl and imidazolyl, or it is a partially or fully hydrogenated radical such as oxiranyl, oxetanyl, pyrrolidyl, piperidyl, piperazinyl, dioxolanyl, morpholinyl, tetrahydrofuryl. Substituents which are suitable for a substituted heterocyclic radical are the substituents mentioned further below, and additionally also oxo. The oxo group can also be present on the hetero ring atoms which may exist at various oxidation levels, for example on N and S.

Substituted radicals, such as substituted hydrocarbon radicals, for example substituted alkyl, alkenyl, alkynyl, aryl, phenyl and benzyl, or substituted heterocyclyl or heteroaryl are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino, such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and also unsaturated aliphatic radicals which correspond to the abovementioned saturated hydrocarbon-containing radicals, such as alkenyl, alkynyl, alkenyloxy, alkynyloxy etc. Preferred among radicals having carbon atoms are those having 1 to 4 carbon atoms, in particular 1 or 2 carbon atoms. Preferred are, in general, substituents selected from the group consisting of halogen, for example fluorine and chlorine, $(C_1-C_4)$alkyl, preferably methyl or ethyl, $(C_1-C_4)$haloalkyl, preferably trifluoromethyl, $(C_1-C_4)$alkoxy, preferably methoxy or ethoxy, $(C_1-C_4)$haloalkoxy, nitro and cyano. Especially preferred in this context are the substituents methyl, methoxy and chlorine. Optionally substituted phenyl is preferably phenyl which is unsubstituted or mono- or polysubstituted, preferably up to trisubstituted, by identical or different radicals selected from the group consisting of halogen, $(C_1-C_4)$alkyl, $(C_1-C_4)$alkoxy, $(C_1-C_4)$haloalkyl, $(C_1-C_4)$haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Mono- or disubstituted amino is a chemically stable radical selected from the group consisting of the substituted amino radicals, which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred in this context are alkyl radicals having 1 to 4 carbon atoms; aryl is in this context preferably phenyl or substituted phenyl; acyl is as defined further below, preferably $(C_1-C_4)$alkanoyl. This also applies correspondingly to substituted hydroxylamino or hydrazino.

An acyl radical is the radical of an organic acid, for example the radical of a carboxylic acid and radicals of acids derived therefrom, such as thiocarboxylic acid, optionally N-substituted iminocarboxylic acids or the radical of carbonic monoesters, of optionally N-substituted carbamic acid, of sulfonic acids, sulfinic acids, phosphonic acids and phosphinic acids. Acyl is, for example, formyl, alkylcarbonyl such as [$(C_1-C_4)$alkyl]carbonyl, phenylcarbonyl, where the phenyl ring may be substituted, for example as shown above for phenyl, or alkyloxycarbonyl, phenyloxycarbonyl, benzyloxycarbonyl, alkylsulfonyl, alkylsulfinyl, N-alkyl-1-iminoalkyl and other radicals of organic acids.

The invention also provides all stereoisomers embraced by formula (I) and mixtures of these. Such compounds of formula (I) contain one or more asymmetric carbon atoms or else double bonds which are not mentioned separately in formula (I). Formula (I) embraces all possible stereoisomers which are defined by their specific spatial form, such as enantiomers, diastereomers and Z and E isomers; they can be obtained by customary methods from mixtures of the stereoisomers or be prepared by stereoselective reactions in combination with the use of stereochemically pure starting materials.

The abovementioned examples of radicals or ranges of radicals which come under the general terms such as "alkyl", "acyl", "substituted radicals", etc., are not meant to be complete lists. The general terms also include the definitions of ranges of radicals in groups of preferred compounds given further below, in particular ranges of radicals which include specific radicals from the examples in the tables.

Compounds of the formula (I) according to the invention or their salts which are of particular interest, mainly for reasons of a higher herbicidal activity, better selectivity and/or because they can be prepared more easily are those in which $R^1$ is H, $(C_1-C_6)$alkyl, $(C_3-C_6)$alkenyl, $(C_3-C_6)$alkynyl, where each of the three last mentioned radicals is unsubstituted or substituted by one or more radicals selected from the group consisting of halogen, unsubstituted and substituted phenyl, unsubstituted and substituted heterocyclyl having 3 to 6 ring atoms, unsubstituted and substituted $(C_3-C_6)$cycloalkyl, $(C_1-C_4)$alkoxy, $(C_1-C_4)$alkylthio, [$(C_1-C_4)$alkoxy]carbonyl and [$(C_1-C_4)$haloalkoxy]carbonyl, or is unsubstituted or substituted $(C_3-C_6)$cycloalkyl, unsubstituted or substituted phenyl, unsubstituted or substituted heterocyclyl having 3 to 6 ring atoms and/or $R^2$ is a group of the formula $R^0—Q^0—$,
in which $R^0$ is a hydrogen atom, $(C_1-C_{12})$alkyl, $(C_3-C_{12})$alkenyl or $(C_3-C_{12})$alkynyl, where each of the three last mentioned radicals is unsubstituted or substituted by one or more radicals selected from the group consisting of halogen, $(C_1-C_6)$alkoxy, $(C_1-C_6)$haloalkoxy, $(C_1-C_6)$alkylthio, $(C_1-C_6)$haloalkylthio, $(C_1-C_6)$alkylsulfinyl, $(C_1-C_6)$haloalkylsulfinyl, $(C_1-C_6)$alkylsulfonyl, $(C_1-C_6)$haloalkylsulfonyl, [$(C_1-C_6)$alkoxy]carbonyl, [$(C_1-C_6)$haloalkoxy]carbonyl, $CONR^6R^7$, $SO_2NR^6R^7$, CN, OH, $(C_3-C_6)$cycloalkyl, $NR^8R^9$, unsubstituted phenyl, substituted phenyl, unsubstituted heterocyclyl and substituted heterocyclyl, or is unsubstituted or substituted $(C_3-C_6)$cycloalkyl, unsubstituted or substituted $(C_3-C_6)$cycloalkenyl, unsubstituted or substituted heterocyclyl or unsubstituted or substituted phenyl and in which $Q^0$ is a direct bond or a divalent group of the formula —O—, —SO$_2$—, —NH—, —N[(C$_1$–C$_6$)alkyl]-, —CO—, —CO—NH— or —O—CO—NH—, and $R^3$ independently of one another are defined as $R^0$ in the radical $R^2$, or $R^2$ and $R^3$ together with the nitrogen atom are a heterocycle of 3–6 ring atoms which is saturated or unsaturated, which may, in addition to the nitrogen atom, contain one or two atoms selected from the group consisting of N, O and S and which is unsubstituted or substituted by one or more radicals selected from the group consisting of $(C_1-C_6)$alkyl, $(C_1-C_6)$alkoxy, halogen, [(C$_1$–C$_6$)alkoxy]carbonyl, $(C_1-C_6)$haloalkyl and oxo, and/or $R^6$ and $R^7$ independently of one another are H, $(C_1-C_6)$alkyl, $(C_3-C_6)$alkenyl, $(C_3-C_6)$alkynyl or unsubstituted or substituted phenyl or $R^6$ and $R^7$ together with the nitrogen atom are a heterocyclic ring having 5 or 6 ring members which may optionally contain further heteroatoms selected from the group consisting of N, O and S and which is unsubstituted or mono- or polysubstituted by radicals selected from the group consisting of $(C_1-C_4)$alkyl and oxo, and $R^8$ and $R^9$ independently of one another and independently of $R^6$ and $R^7$ are as defined under $R^6$ and $R^7$ or are $(C_1-C_4)$alkylcarbonyl, $(C_1-C_4)$haloalkylcarbonyl, $(C_1-C_4)$-alkoxycarbonyl or $(C_1-C_4)$alkylsulfonyl, Q is O or NR*, where R* is as defined above, and/or X and Y independently of one another are H, halogen, $(C_1-C_4)$alkyl, $(C_1-C_4)$alkoxy, $(C_1-C_4)$alkylthio, where each of the three last mentioned radicals is unsubstituted or substituted by one or more radicals selected from the group consisting of halogen, $(C_1-C_3)$alkoxy and $(C_1-C_4)$alkylthio, are mono- or di[(C$_1$–C$_4$)alkyl] amino, $(C_3-C_6)$cycloalkyl, $(C_3-C_5)$alkenyl, $(C_3-C_5)$alkenyloxy or $(C_3-C_5)$alkynyloxy and Z is CH or N, where substituted phenyl, substituted heterocyclyl, substituted cycloalkyl or substituted cycloalkenyl preferably carries one or more radicals selected from the group consisting of halogen, $(C_1-C_4)$alkyl, $(C_1-C_4)$haloalkyl, $(C_1-C_4)$alkoxy-$(C_1-C_4)$alkyl, di-[(C$_1$–C$_4$)alkoxy]-$(C_1-C_4)$alkyl, $(C_1-C_4)$haloalkoxy, $(C_1-C_4)$alkylthio, $(C_1-C_4)$alkylsulfinyl, $(C_1-C_4)$haloalkylsulfinyl, $(C_1-C_4)$alkylsulfonyl, $(C_1-C_4)$haloalkylsulfonyl, NR$^8$R$^9$, [(C$_1$–C$_4$)alkoxy]carbonyl, [(C$_1$–C$_4$)haloalkoxy]carbonyl, [(C$_1$–C$_4$)alkyl]carbonyl, OH, phenyl, CN and NO$_2$ as substituents and where each of the radicals $R^1$, $R^2$ and $R^3$ has, including substituents, 1 to 20 carbon atoms, preferably 1 to 16 carbon atoms.

Of particular interest are compounds of the formula (I) according to the invention in which $R^1$ is H, $(C_1-C_6)$alkyl, $(C_3-C_6)$alkenyl or $(C_3-C_6)$alkynyl, where each of the three last mentioned radicals is unsubstituted or substituted by one or more radicals selected from the group consisting of halogen, phenyl, $(C_1-C_4)$alkoxy, $(C_1-C_4)$alkylthio and [(C$_1$–C$_4$)alkoxy] carbonyl or is $(C_3-C_6)$cycloalkyl, $(C_3-C_6)$cycloalkyl $(C_1-C_3)$alkyl, heterocyclyl having 3 to 6 ring atoms or heterocyclyl-$(C_1-C_3)$alkyl having 3 to 6 ring atoms, where each of the four last mentioned radicals is unsubstituted or substituted by one or more radicals selected from the group consisting of halogen, $(C_1-C_4)$ alkyl and $(C_1-C_4)$alkoxy, and/or $R^2$ is a group of the formula $R^0$—$Q^0$—, in which $R^0$ is a hydrogen atom, $(C_1-C_8)$alkyl, $(C_3-C_8)$alkenyl or $(C_3-C_8)$alkynyl, where each of the three last mentioned radicals is unsubstituted or substituted by one or more radicals selected from the group consisting of halogen, $(C_1-C_4)$alkoxy, $(C_1-C_4)$haloalkoxy, $(C_1-C_4)$alkylthio, $(C_1-C_4)$haloalkylthio, $(C_1-C_4)$alkylsulfinyl, $(C_1-C_4)$ haloalkylsulfinyl, $(C_1-C_4)$alkylsulfonyl, $(C_1-C_4)$ haloalkylsulfonyl, [(C$_1$–C$_6$)alkoxy]carbonyl, CONR$^6$R$^7$, SO$_2$NR$^6$R$^7$, CN, OH, $(C_3-C_6)$cycloalkyl, NR$^8$R$^9$, phenyl, which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$alkylsufonyl, NR$^8$R$^9$, [(C$_1$–C$_4$)alkoxy]carbonyl, [(C$_1$–C$_4$)alkyl]carbonyl, phenyl, [(C$_1$–C$_4$)alkyl]carbonyl, CN and NO$_2$ and heterocyclyl which is unsubstituted or substituted by one or more radicals selected from the group consisting of halogen, $(C_1-C_4)$alkyl, $(C_1-C_4)$haloalkyl, $(C_1-C_4)$ alkoxy, $(C_1-C_4)$haloalkoxy, $(C_1-C_4)$alkylthio, $(C_1-C_4)$ alkylsulfinyl, $(C_1-C_4)$alkylsulfonyl, NR$^8$R$^9$, [(C$_1$–C$_4$) alkoxy]carbonyl, [(C$_1$–C$_4$)alkyl]carbonyl, phenyl, [(C$_1$–C$_4$)alkyl]carbonyl, CN and NO$_2$, or is $(C_3-C_6)$ cycloalkyl, which is unsubstituted or substituted by one or more radicals selected from the group consisting of halogen, $(C_1-C_4)$alkyl, $(C_1-C_4)$haloalkyl, $(C_1-C_4)$ alkoxy, $(C_1-C_4)$haloalkoxy, [(C$_1$–C$_4$)alkoxy]carbonyl, CN, OH and phenyl, or is $(C_3-C_6)$cycloalkenyl, which is unsubstituted or substituted by one or more radicals selected from the group consisting of halogen, $(C_1-C_4)$alkyl, $(C_1-C_4)$ haloalkyl, $(C_1-C_4)$alkoxy and [(C$_1$–C$_4$)alkoxy] carbonyl, or is heterocyclyl or phenyl, where each of the two last mentioned radicals is unsubstituted or substituted by one or more radicals selected from the group consisting of halogen, $(C_1-C_4)$alkyl, $(C_1-C_4)$ haloalkyl, $(C_1-C_4)$alkoxy, $(C_1-C_4)$haloalkoxy, $(C_1-C_4)$alkylthio, $(C_1-C_4)$alkylsulfinyl, $(C_1-C_4)$ alkylsufonyl, NR$^8$R$^9$, [(C$_1$–C$_4$)alkoxy]carbonyl, [(C$_1$–C$_4$)alkyl]carbonyl, phenyl, [(C$_1$–C$_4$)alkyl] carbonyl, CN and NO$_2$, and $Q^0$ is a direct bond or a divalent group of the formula —O—, —SO$_2$—, —NH—, —CO— NH— or —O—CO—NH—, preferably is a direct bond or —O—, —SO$_2$— or —NH—, $R^3$ independently of one another is defined as $R^0$ in the radical $R^2$, or $R^2$ and $R^3$ together with the nitrogen atom are a heterocycle of 3–6 ring atoms which is saturated or unsaturated and which may, in addition to the nitrogen atom, contain one or two heteroatoms selected from the group consisting of N, O and S and which is unsubstituted or substituted by one or more radicals selected from the group consisting of $(C_1-C_3)$alkyl, $(C_1-C_3)$alkoxy, halogen, [(C$_1$–C$_3$)-alkoxy]carbonyl, $(C_1-C_3)$haloalkyl and oxo, and/or $R^6$ and $R^7$ independently of one another represent H, $(C_1-C_4)$alkyl, $(C_3-C_4)$alkenyl, $(C_3-C_4)$alkynyl or phenyl, which is unsubstituted or substituted by one or more radicals selected from the group consisting of halogen, $(C_1-C_4)$alkyl, $(C_1-C_4)$haloalkyl, $(C_1-C_4)$alkoxy, $(C_1-C_4)$alkylthio, $(C_1-C_4)$alkylsulfonyl, $[(C_1-C_4)$alkoxy]carbonyl, CN and $NO_2$, preferably is H or $(C_1-C_4)$Alkyl, or $R^6$ and $R^7$ together with the nitrogen atom are a heterocyclic ring having 5 or 6 ring members which may optionally contain other heteroatoms selected from the group consisting of N, O and S and which is unsubstituted or mono- or polysubstituted by radicals selected from the group consisting of $(C_1-C_4)$alkyl and oxo, preferably are, together with the nitrogen atom, a heterocyclic ring having 5 or 6 ring members which may optionally contain a further heteroatom selected from the group consisting of N and O and which is unsubstituted or mono- or polysubstituted by radicals selected from the group consisting of $(C_1-C_4)$ alkyl and oxo, and/or $R^8$ and $R^9$ independently of one another and independently of $R^6$ and $R^7$ are as defined under $R^6$ and $R^7$ or are $(C_1-C_4)$alkylcarbonyl, $(C_1-C_4)$haloalkylcarbonyl, $(C_1-C_4)$-alkoxycarbonyl or $(C_1-C_4)$alkylsulfonyl, and Q is O or NR*, where R* is as defined further above, and/or X and Y independently of one another are H, halogen, $(C_1-C_4)$alkyl, $(C_1-C_4)$alkoxy, $(C_1-C_4)$alkylthio, where each of the three last mentioned radicals is unsubstituted or substituted by one or more radicals selected from the group consisting of halogen, $(C_1-C_3)$alkoxy and $(C_1-C_4)$alkylthio, are mono- or di[$(C_1-C_4)$alkyl] amino, $(C_3-C_6)$cycloalkyl, $(C_3-C_5)$alkenyl, $(C_3-C_5)$alkenyloxy or $(C_3-C_5)$alkynyloxy and Z is CH or N.

Of particular interest are also compounds of the formula (I) according to the invention and salts thereof in which $R^1$ is $(C_1-C_6)$alkyl, which is unsubstituted or substituted by one or more radicals selected from the group consisting of halogen and $(C_1-C_4)$alkoxy, or is 3-oxetanyl, $(C_3-C_4)$alkenyl or $(C_3-C_4)$alkynyl, and/or $R^2$ is H, $(C_1-C_6)$alkyl, $(C_3-C_6)$alkenyl, $(C_3-C_6)$alkynyl, where each of the three last mentioned radicals is unsubstituted or substituted by one or more radicals selected from the group consisting of halogen, $(C_1-C_4)$alkoxy, $(C_1-C_4)$alkylthio, $(C_1-C_4)$alkylsulfonyl, $[(C_1-C_4)$alkoxy]carbonyl, $(C_3-C_6)$cycloalkyl, CN and OH, or is $(C_3-C_6)$cycloalkyl, which is unsubstituted or substituted by one or more radicals selected from the group consisting of halogen, $(C_1-C_4)$alkyl, $(C_1-C_4)$alkoxy, $[(C_1-C_4)$alkoxy]carbonyl, CN and OH, or is $(C_3-C_6)$cycloalkenyl, $(C_1-C_4)$alkoxy, $(C_1-C_4)$alkenyloxy, $(C_1-C_4)$alkylsulfonyl, $(C_1-C_4)$alkylamino or di[$(C_1-C_4)$alkyl]amino and $R^3$ is H, $(C_1-C_6)$alkyl, $(C_3-C_6)$alkenyl, $(C_3-C_6)$alkynyl, where each of the three last mentioned radicals is unsubstituted or substituted by one or more radicals selected from the group consisting of halogen, $(C_1-C_4)$alkoxy, $(C_1-C_4)$alkylthio, $(C_1-C_4)$alkylsulfonyl, $[(C_1-C_4)$alkoxy]carbonyl, $(C_3-C_6)$cycloalkyl, CN and OH, or is $(C_3-C_6)$cycloalkyl, which is unsubstituted or substituted by one or more radicals selected from the group consisting of halogen, $(C_1-C_4)$alkyl, $(C_1-C_4)$alkoxy, $[(C_1-C_4)$alkoxy]carbonyl, CN and OH, or is $(C_3-C_6)$cycloalkenyl or $R^2$ and $R^3$ together with the nitrogen atom are a heterocycle of 3–6 ring atoms which is saturated or unsaturated, which may, in addition to the nitrogen atom, contain one or two atoms selected from the group consisting of N, O and S and which is unsubstituted or substituted by one or more radicals selected from the group consisting of halogen, $(C_1-C_3)$alkyl, $(C_1-C_3)$alkoxy, oxo and $[(C_1-C_3)$alkoxy]carbonyl, and/or $R^4$ is H, $(C_1-C_4)$alkyl, $(C_1-C_4)$haloalkyl, $(C_1-C_4)$alkoxy or halogen, and/or $R^5$ is H or methyl, and/or R* is H or $(C_1-C_4)$alkyl, and/or X and Y independently of one another are $(C_1-C_4)$alkyl, $(C_1-C_4)$alkoxy, where each of the two last mentioned radicals is unsubstituted or substituted by one or more halogen atoms, or are $(C_1-C_4)$alkylthio, halogen or mono- or di[$(C_1-C_2)$alkyl]amino and/or W is an oxygen atom.

Preferred compounds of the formula (I) according to the invention or salts thereof are those in which $R^2$ and $R^3$ independently of one another are H, $(C_1-C_4)$ alkyl, $(C_1-C_3)$alkenyl, $(C_1-C_3)$alkynyl, $(C_1-C_3)$ cycloalkyl or $(C_3-C_6)$cycloalkenyl, and/or $R^4$ is H, $(C_1-C_3)$alkyl or halogen, and/or R* is $(C_1-C_3)$alkyl, and/or X is $(C_1-C_2)$alkyl, $(C_1-C_2)$alkoxy, $(C_1-C_2)$alkylthio, $(C_1-C_2)$haloalkyl or $(C_1-C_2)$haloalkoxy and Y is $(C_1-C_2)$alkyl, $(C_1-C_2)$alkoxy, halogen, $NHCH_3$ or $N(CH_3)_2$.

Particularly preferred compounds of the formula (I) according to the invention or salts thereof are those in which $R^1$ is $(C_1-C_3)$alkyl, allyl or propargyl and/or $R^4$ is H and/or Q is an oxygen atom.

Particular preference is also given to compounds of the formula (I) according to the invention and salts thereof which contain a combination of radicals from the above-mentioned compounds of particular interest or the preferred compounds, and also those which contain one or more radicals from the compounds listed in Tables 1 and 2 (see below).

The present invention also provides processes for preparing the compounds of the formula (I) according to the invention or salts thereof, which comprises a) reacting a compound of the formula (II)

(II)

with a heterocyclic carbamate of the formula (III), (III)

in which R is optionally substituted aryl or an aliphatic radical, preferably phenyl or $(C_1-C_4)$alkyl, or b) reacting a sulfonylcarbamate of the formula (IV)

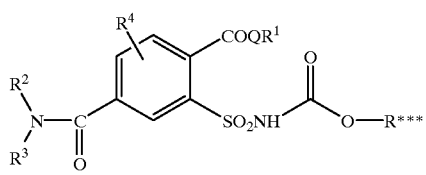
(IV)

in which R is optionally substituted phenyl or ($C_1$–$C_4$) alkyl with an amino heterocycle of the formula (V)

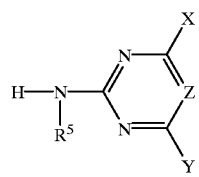
(V)

or c) reacting a sulfonyl isocyanate of the formula (VI)

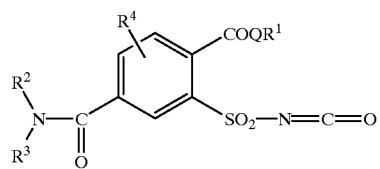
(VI)

with an amino heterocycle of the formula (V) or d) reacting a sulfonamide of the formula (II) with a (thio)isocyanate of the formula (VII)

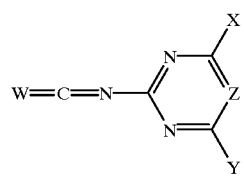
(VII)

in the presence of a base or e) reacting an amino heterocycle of the formula (V) initially under base-catalysis with a carbonate, for example diphenyl carbonate, and reacting the intermediate formed in a one-pot reaction with a sulfonamide of the formula (II) (see variant a), where in the formulae (II)–(VII) the radicals or groups $R^1$–$R^5$, W, X, Y and Z are as defined in formula (I) and in process variants a) to c) and e), initially compounds (I) where W=O are obtained.

The compounds of the formulae (II) and (III) are preferably reacted base-catalyzed in an inert organic solvent, such as, for example, dichloromethane, acetonitrile, dioxane or THF, at temperatures between 0° C., preferably 20° C., and at the boiling point of the solvent. Suitable bases here are, for example, organic amine bases, such as 1,8-diazabicyclo[5.4.0]undec-7-ene (DBU), or alkali metal hydroxides, such as, for example, NaOH, in particular when $R^0$=(subst.) phenyl (cf. EP-A44807), or trimethylaluminum or triethylaluminum, the two last mentioned compounds in particular when $R^0$=alkyl (cf. EP-A-166 516). The base in question is employed here in the range of 1 to 3 molar equivalents, for example, based on the compound of the formula (II).

The sulfonamides (II) and the structurally related compounds of the formulae (IV) and (VI) are novel compounds. The compounds and their preparation also form part of the subject matter of this invention.

The compounds of the formula (II) are obtained, for example, starting from compounds of the formula (VIII)

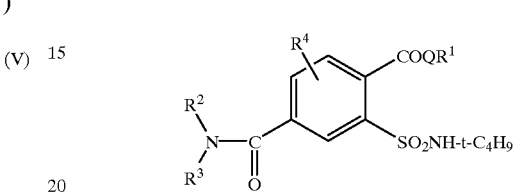
(VIII)

in which $R^1$–$R^4$ are as defined in formula (I), by reaction with a strong acid (cf. in this context WO 89/10921). Suitable strong acids are, for example, mineral acids, such as $H_2SO_4$ or HCl, or strong organic acids, such as trifluoro acetic acid. The tert-butyl protective group is cleaved off, for example, at temperatures from –20° C. to the respective reflux temperature of the reaction mixture, preferably at from 0° C. to 40° C. The reaction can be carried out neat or else in an inert solvent, such as, for example, dichloromethane or trichloromethane.

Alternatively, the sulfonamides of the formula (II) where Q=O are also obtainable starting from the saccharin derivatives of the formula (IX) by reaction with gaseous hydrogen chloride in the presence of an alcohol of the formula $R^1OH$ ($R^1$–$R^4$ are as defined in the formula (I)

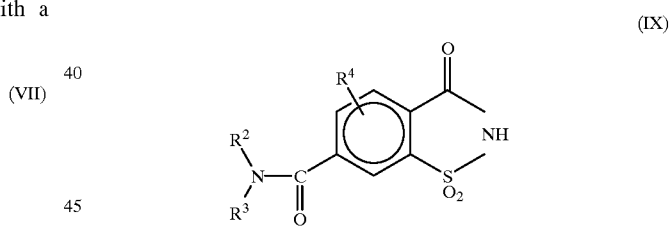
(IX)

The reaction is carried out, for example, at temperatures between 0° C. and the boiling point of the alcohol $R^1OH$, and the alcohol $R^1OH$ may at the same time serve as solvent (cf. in this context: U.S. Pat. No. 4,566,898; J. Pharmaceutical Sciences 56, 134 1967)). A further synthesis possibility for preparing the compounds of the formula II) consists in reacting the sulfonyl chlorides of the formula (X) with ammonia,

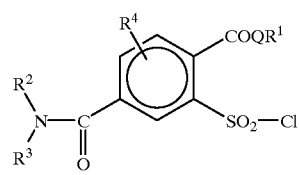
(X)

where the radicals $R^1$ to $R^4$ and Q are as defined in the formula (I). The reaction is carried out, for example, in inert solvents, such as, for example, dichloromethane, tetrahydrofuran (THF), dioxan, toluene or dimethylformamide (DMF), at temperatures of from −70° C. to the boiling point of the solvent, preferably up to 25° C. It is preferred here to use an amount of ammonia of 1.5–2.5 equivalents, based on the sulfonyl chloride.

The intermediates of the formula (VIII) are obtained, for example, in accordance with scheme 1:

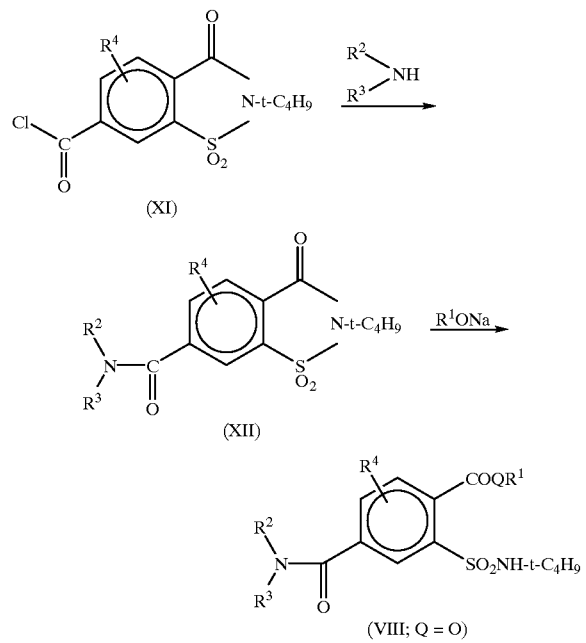

The compounds of the formula (XI) are described in WO 96/05182. Their reaction with amines to give the amides of the formula (XII) is carried out by methods which are known in principle (cf. Houben-Weyl "Methoden der Organischen Chemie", 4th Ed., Vol. 8, p. 655 ff, Thieme Verlag, Stuttgart, 1952).

A base-catalyzed opening of the saccharin ring in (XII) finally leads to the compounds of the formula (VII) where Q=O, where the alcohol $R^1OH$ in question serves as solvent and the base used is the corresponding alkoxide, preferably the sodium alkoxide. The reaction is preferably carried out at temperatures between −20° C. and the boiling point of the alcohol. Similar to known methods, the compounds (VII) where Q=NR* are obtained from the compounds (VII) where Q=O by reaction with the amines $HNR^1R^*$, where $R^1$ and R* are as defined in formula (I) (cf. Houben-Weyl, "Methoden der Organischen Chemie", 4th Ed., Vol. 8, p. 658 ff, Thieme Verlag, Stuttgart, 1952).

A further method for synthesizing compounds of the formula (VII) consists in the opening of the saccharin ring in (XII) using an equivalent of potassium hydroxide. The reaction is carried out, for example, in aqueous ethanol, acetone, acetonitrile or pyridine, at temperatures of from 25° C. to the boiling point of the solvent mixture. The resulting potassium carboxylate of the formula (VIII), in which Q=O and $R^1$=K, can subsequently be alkylated using 1 to 5 equivalents of alkyl halide R-Hal, preferably in the presence of 1,4,7,10,13,16-hexacyclooctane (18-crown-6), for example of 0.1 equivalents of 18-crown6 under phase-transfer conditions, to give the compound (VIII; Q=O, $R^1$=R). The reaction is carried out, for example, in acetonitrile or benzene, at temperatures between 25° C. and the boiling point of the solvent (cf. in this context Tetrahedron Lett. 28, 2417–2420 (1974)).

Besides the synthesis route described in WO 96/05182, the acyl chlorides of the formula (XI) are advantageously obtained in accordance with scheme 2.

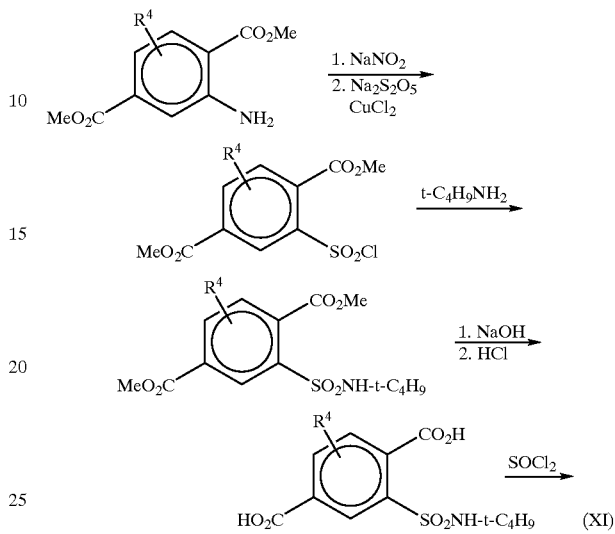

The starting material dimethyl aminoterephthalate, for example, is commercially available; all reaction steps can be carried out similar to methods known from the literature.

The intermediates (IX) can be obtained in accordance with scheme 3.

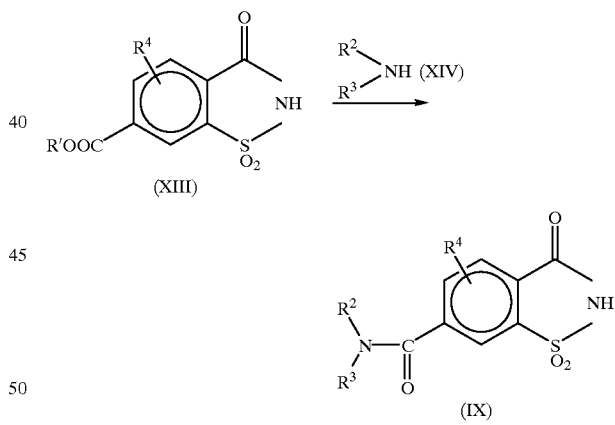

In the compounds of the formulae of schemes 1 to 3, in particular of the formulae (VIII) and (IX), (XI), (XII), (XIII) and (XIV), the radicals $R^1$–$R^4$ are as defined in formula (I). $R^1$ in formula (XIII), scheme 3, is H or an optionally substituted hydrocarbon radical, such as ($C_1$–$C_4$)alkyl, ($C_1$–$C_4$)haloalkyl or phenyl. In the case where R'=H, the carboxyl function first has to be activated by a suitable agent. Suitable agents are, in particular, alkyl chloroformates, such as, for example, isobutyl chloroformate, carbonyidiimidazole or dicyclohexylcarbodiimide. The reaction is carried out, for example, in an inert solvent at temperatures between −20° C. and the boiling point of the solvent. The starting material (XIII) where R'=$R^4$=H is known (cf. in this context Chem. Ber. 115, 1740 (1982)). The esters of the formula (XIII) where R'=($C_1$–$C_6$)

alkyl are described in WO 96/05184. Their reaction with the amines (XIV) is preferably carried out in an inert solvent at temperatures between 20° C. and the boiling point of the solvent.

Secondary alkyl- or allylamines of the formula (XIV) can be prepared by reacting primary amines with halogen compounds using methods which are known in principle (cf. in this context Ind. J. Chem. 15B, 135 (1977); J. Am. Chem. Soc. 81, 719, 722, 727 (1959); Bull. Chim. Soc. France II, 9–10, 395 (1984); Tetrahedron 29, 4118 (1973)).

Many of the amines (XIV) are commercially available or can be prepared similarly to methods which are generally known to the person skilled in the art.

The invention also provides the saccharin derivatives of the formula (IX)' and their preparation

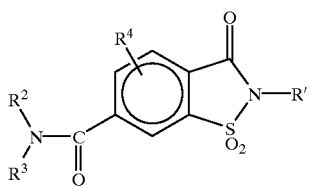

in which $R^1$ to $R^4$ are as defined in formula (I) according to claim 1 and R' is a protective group such as alkyl, in particular tert-butyl, and which preferably include the compounds (IX) and (XII).

The intermediates of the formula (X) can be obtained in accordance with scheme 4.

Scheme 4

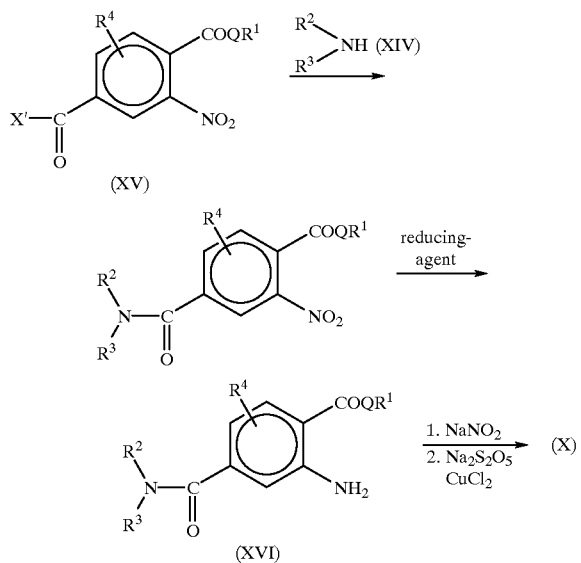

In the formulae of scheme 4, the radicals $R_1$–$R^4$ and Q are as defined in formula (I) and X' is OH or Cl. In the case where X'=OH, for example the compound where $R^1$=methyl, $R^4$=H and Q=O is commercially available. Other compounds of the type (XV) are obtainable by known routes (cf. in this context Monatsh. Chem. 23, 406, 410, 412 (1902)). To react the compounds (XV) where X'=OH with the amines (XIV), the carboxyl function first has to be activated using a suitable agent. Suitable agents are, in particular, alkyl chloroformates, such as, for example, isobu-tyl chloroformate, carbonyldiimidazole or dicyclohexylcarbodiimide. The reaction is carried out, for example, in an inert solvent at temperatures between −20° C. and the boiling point of the solvent. In the case where X'=Cl, some of the compounds (XV) are known, or they can be prepared similarly to known methods (cf. in this context J. Chem. Soc. 113, 66 (1918)). Their reaction to give amides is likewise carried out similarly to known methods (cf. in this context Houben-Weyl, "Methoden der organischen Chemie", 4th Ed., Vol. 8, p. 655 ff, Thieme Verlag Stuttgart, 1952). The further reactions to give the aniline derivatives (XVI) or the sulfonyl chlorides (X) can be carried out similarly to known methods; cf. Houben-Weyl, "Methoden der organischen Chemie", 4th Ed., Vol.11/1, p. 360 ff, Thieme Verlag Stuttgart, 1957 or ibid. 9, p. 579ff, 1955.

The carbamates of the formula (III) can be prepared by methods which are described in the South African patent applications 82/5671 and 82/5045 or EP-A 70804 (U.S. Pat. No. 4,480,101) or RD 275056.

The reaction of the compounds (IV) with the amino heterocycles (V) is preferably carried out in inert aprotic solvents, such as, for example, dioxane, acetonitrile or tetrahydrofuran, at temperatures between 0° C. and the boiling point of the solvent. The required starting materials (V) are known from the literature or can be prepared by methods known from the literature. The phenylsulfonylcarbamates of the formula (IV) are obtained similarly to U.S. Pat. No. 4,684,393 or U.S. Pat. No. 4,743,290.

The phenylsulfonyl isocyanates of the formula (VI) can be prepared and reacted with the amino heterocycles (V) similarly to U.S. Pat. No. 4,481,029.

The (thio)isocyanates of the formula (VII) are obtainable by processes known from the literature (EP-A-232067, EP-A-166516). The reaction of the (thio)isocyanates (VII) with compounds (II) is carried out, for example, at from −10° C. to 100° C., preferably from 20° C. to 100° C., in an inert aprotic solvent, such as, for example, acetone or acetonitrile, in the presence of a suitable base, for example $N(C_2H_5)_3$ or $K_2CO_3$.

Avoiding the isolation of intermediates, such as, for example, the isocyanates of the formula (VI), the compounds of the formula (I) can also be prepared directly from the sulfonyl chlorides (X) and the amino heterocycles (V) in the presence of an alkali metal cyanate or ammonium cyanate and pyridine (cf. in this context U.S. Pat. No. 5,157,119).

The reaction of an amino heterocycle of the formula (V) with diphenyl carbonate and a sulfonamide of the formula (II) in a one-pot reaction can be carried out in accordance with EP-A-562 575.

The abovementioned compounds of the formulae (II), (IV), (VI), (VIII) and (X) are structurally related novel intermediates of the formula (II)*

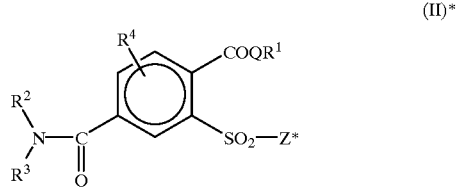

in which Z*=$NH_2$, NHCOOR*, NCO, NH-tert-butyl or Cl and $R_1$–$R^4$ R* and Q are as defined in formula (I) or formula (IV).

The salts of the compounds of the formula (I) are preferably prepared in inert polar solvents, such as, for example, water, methanol or acetone, at temperatures of from 0° C. to 100° C. Suitable bases for preparing the salts according to the invention are, for example, alkali metal carbonates, such as potassium carbonate, alkali metal hydroxides and alkaline earth metal hydroxides, for example NaOH or KOH, or alkali metal alkoxides, such as sodium methoxide or sodium tert-butoxide, or ammonia or ethanolamine. The "inert solvents" mentioned in the process variants above are to be understood as meaning in each case solvents which are inert under the reaction conditions in question, but which need not be inert under any reaction conditions.

The compounds of the formula (I) according to the invention and their salts, hereinbelow together referred to as compounds of the formula (I) (according to the invention), have an outstanding herbicidal activity against a broad spectrum of economically important monocotyledonous and dicotyledonous harmful plants. The active compounds also act efficiently on perennial weeds which produce shoots from rhizomes, root stocks or other perennial organs and which are difficult to control. In this context, it is immaterial whether the substances are applied pre-sowing, pre-emergence or post-emergence. Specifically, examples may be mentioned of some representatives of the monocotyledonous and dicotyledonous weed flora which can be controlled by the compounds according to the invention, without these being a restriction to certain species. Examples of weed species on which the active compounds act efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the spectrum of action extends to species such as, for example, Galium, Viola, Veronica, Lamium, Stellaria, Amaranthus, Sinapis, lpomoea, Matricaria, Abutilon and Sida from amongst the annuals, and Convolvulus, Cirsium, Rumex and Artemisia in the case of the perennial weeds.

The active ingredients according to the invention also effect outstanding control of weeds which occur under the specific conditions of rice growing such as, for example, Echinochloa, Sagittaria, Alisma, Eleocharis, Scirpus and Cyperus. If the compounds according to the invention are applied to the soil surface prior to germination, then the weed seedlings are either prevented completely from emerging, or the weeds grow until they have reached the cotyledon stage but then their growth stops, and, eventually, after three to four weeks have elapsed, they die completely.

If the active compounds are applied post-emergence to the green parts of the plants, growth also stops drastically a very short time after the treatment and the weed plants remain at the developmental stage of the point in time of application, or they die completely after a certain time, so that in this manner competition by the weeds, which is harmful to the crop plants, is eliminated at a very early point in time and in a sustained manner.

Although the compounds according to the invention have an excellent herbicidal activity against monocotyledonous and dicotyledonous weeds, crop plants of economically important crops such as, for example, wheat, barley, rye, rice, corn, sugarbeet, cotton and soya, are not damaged at all, or only to a negligible extent. For these reasons, the present compounds are highly suitable for selectively controlling undesired plant growth in plantings for agricultural use or in plantings of ornamentals.

In addition, the substances according to the invention have outstanding growth-regulating properties in crop plants. They engage in the plant metabolism in a regulating manner and can this be employed for the targeted control of plant constituents and for facilitating harvesting, for example by provoking desiccation and stunted growth. Furthermore, they are also suitable for generally regulating and inhibiting undesirable vegetative growth, without destroying the plants in the process. Inhibition of vegetative growth plays an important role in many monocotyledon and dicotyledon crops because lodging can be reduced hereby, or prevented completely.

Owing to their herbicidal and plant growth-regulatory properties, the active compounds can also be employed for controlling harmful plants in crops of known or still to be developed genetically engineered plants. The transgenic plants generally have particularly advantageous properties, for example resistance to certain pesticides, in particular certain herbicides, resistance to plant diseases or causative organisms of plant diseases, such as certain insects or microorganisms such as fungi, bacteria or viruses. Other particular properties relate, for example, to the quantity, quality, storage-stability, composition and to specific ingredients of the harvested product. Thus, transgenic plants having an increased starch content or a modified quality of the starch or those having a different fatty acid composition of the harvested produce are known.

The use of the compounds of the formula (I) according to the invention or their salts in economically important transgenic crops of useful and ornamental plants, for example of cereal, such as wheat, barley, rye, oats, millet, rice, maniok and corn, or else in crops of sugarbeet, cotton, soya, rapeseed, potato, tomato, pea and other vegetable species is preferred. The compounds of the formula (I) can preferably be used as herbicides in crops of useful plants which are resistant or which have been made resistant by genetic engineering toward the phytotoxic effects of the herbicides.

Conventional ways for preparing novel plants which have modified properties compared to known plants comprise, for example, traditional breeding methods and the generation of mutants. Alternatively, novel plants having modified properties can be generated with the aid of genetic engineering methods (see, for example, EP-A 0 221 044, EP-A 0 131 624). For example, there have been described several cases of genetically engineered changes in crop plants in order to modify the starch synthesized in the plants (for example WO 92/11376, WO 92/14827, WO 91/19806), transgenic crop plants which are resistant to certain herbicides of the glufosinate- (cf., for-example, EP-A 0 242 236, EP-A 0 242 246) or glyphosate-type (WO 92/00377), or of the sulfonylurea-type (EP-A 0 257 993, U.S. Pat. No. 5,013,659), transgenic crop plants, for example cotton, having the ability to produce Bacillus thuringiensis toxins (Bt toxins) which impart resistance to certain pests to the plants (EP-A 0 142 924, EP-A 0 193 259), transgenic crop plants having a modified fatty acid composition (WO 91/13972).

Numerous molecular biological techniques which allow the preparation of novel transgenic plants having modified properties are known in principle; see, for example, Sambrook et al., 1989, Molecular Cloning, A Laboratory Manual, 2nd ed. Cold Spring Harbor Laboratory Press, Cold Spring Harbor, N.Y.; or Winnacker "Gene und Klone" [Genes and Clones], VCH Weinheim, 2nd edition 1996, or Christou, "Trends in Plant Science" 1 (1996) 423–431). In order to carry out such genetic engineering manipulations, it is possible to introduce nucleic acid molecules into plasmids which allow a mutagenesis or a change in the sequence to occur by recombination of DNA sequences. Using the abovementioned standard processes it is possible, for example, to exchange bases, to remove partial sequences or to add natural or synthetic sequences. To link the DNA fragments with each other, it is possible to attach adaptors or linkers to the fragments.

Plant cells having a reduced activity of a gene product can be prepared, for example, by expressing at least one appropriate antisense-RNA, a sense-RNA to achieve a cosuppression effect, or by expressing at least one appropriately constructed ribozyme which specifically cleaves transcripts of the abovementioned gene product.

To this end it is possible to employ both DNA molecules which comprise the entire coding sequence of a gene product including any flanking sequences that may be present, and DNA molecules which comprise only parts of the coding sequence, it being necessary for these parts to be long enough to cause an antisense effect in the cells. It is also possible to use DNA sequences which have a high degree of homology to the coding sequences of a gene product but which are not entirely identical.

When expressing nucleic acid molecules in plants, the synthesized protein can be localized in any desired compartment of the plant cells. However, to achieve localization in a certain compartment, it is, for example, possible to link the coding region with DNA sequences which ensure localization in a certain compartment. Such sequences are known to the person skilled in the art (see, for example, Braun et al., EMBO J. 11 (1992), 3219–3227; Wolter et al., Proc. Natl. Acad. Sci. U.S.A. 85 (1988), 846–850; Sonnewald et al., Plant J. 1 (1991), 95–106).

The transgenic plant cells can be regenerated to whole plants using known techniques. The transgenic plants can in principle be plants of any desired plant species, i.e. both monocotyledonous and dicotyledonous plants.

In this manner, it is possible to obtain transgenic plants which have modified properties by overexpression, suppression or inhibition of homologous (=natural) genes or gene sequences or by expression of heterologous (=foreign) genes or gene sequences.

The compounds (I) according to the invention can preferably be used in transgenic crops which are resistant to herbicides from the group consisting of the sulfonylureas, glufosinate-ammonium or glyphosate-isopropylammonium and analogous active compounds.

When using the active compounds according to the invention in transgenic crops, in addition to the effects against harmful plants which can be observed in other crops, there are frequently effects which are specific for the application in the respective transgenic crop, for example a modified or specifically broadened spectrum of weeds which can be controlled, modified application rates which can be used for the application, preferably good combinability with the herbicides to which the transgenic crops are resistant, and an effect on the growth and the yield of the transgenic crop plants.

The invention therefore also provides for the use of the compounds (I) according to the invention as herbicides for controlling harmful plants in transgenic crop plants.

The novel compounds can be applied in the customary formulations in the form of wettable powders, emulsifiable concentrates, sprayable solutions, dusts or granules. The invention therefore also provides herbicidal and plant growth-regulating compositions comprising compounds of the formula (I).

The compounds of the formula (I) can be formulated in various ways depending on the prevailing biological and/or chemico-physical parameters. Examples of suitable formulation options are: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing compositions, granules for broadcasting and soil application, granules (GR) in the form of microgranules, spray granules, coating granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Technology], Volume 7, C. Hauser Verlag Munich, 4th. Edition 1986; Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and other additives, are likewise known and are described, for example, in Watkins, "Handbook of Insecticide Dust Diluents and Carriers", 2nd Ed., Darland Books, Caldwell N.J., H.v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Edition 1986.

Based on these formulations it is also possible to produce combinations with other pesticidally active substances, for example insecticides, acaricides, herbicides and fungicides, and also with safeners, fertilizers and/or growth regulators, for example in the form of a ready-mix or tank mix.

Wettable powders are preparations which are uniformly dispersible in water and which contain, in addition to the active compound and as well as a diluent or inert substance, surfactants of ionic and/or nonionic type (wetting agents, dispersants), for example polyethoxylated alkyl phenols, polyethoxylated fatty alcohols, polyethoxylated fatty amines, fatty alcohol polyglycol ethersulfates, alkanesulfonates, alkylbenzenesulfonates, sodium ligninsulfonate, sodium 2,2'-dinaphthylmethane-6,6'-disulfonate, sodium dibutylnaphthalenesulfonate or else sodium oleoylmethyltaurinate. To prepare the wettable powders, the herbicidally active compounds are finely ground, for example in customary apparatus such as hammer mills, fan mills and air-jet mills, and are mixed simultaneously or subsequently with the formulation auxiliaries.

Emulsifiable concentrates are prepared by dissolving the active compound in an organic solvent, for example butanol, cyclohexanone, dimethylformamide, xylene or else relatively high-boiling aromatic compounds or hydrocarbons or mixtures of the organic solvents, with the addition of one or more surfactants of ionic and/or nonionic type (emulsifiers). Examples of emulsifiers which can be used are calcium alkylarylsulfonates, such as Ca dodecylbenzenesulfonate, or nonionic emulsifiers, such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters or polyoxyethylene sorbitan esters, for example polyoxyethylene sorbitan fatty acid esters.

Dusts are obtained by grinding the active compound with finely divided solid substances, for example talc, natural clays, such as kaolin, bentonite and pyrophyllite, or diatomaceous earth.

Suspension concentrates can be water- or oil-based. They can be prepared, for example, by wet milling using commercially customary bead mills, with or without the addition of surfactants as already mentioned above, for example, in the case of the other formulation types.

Emulsions, for example oil-in-water emulsions (EW), can be prepared for example by means of stirrers, colloid mills and/or static mixers using aqueous organic solvents and, if desired, surfactants as already mentioned above, for example, in the case of the other formulation types.

Granules can be prepared either by spraying the active compound onto adsorptive, granulated inert material or by applying active-compound concentrates to the surface of carriers such as sand, kaolinites or granulated inert material, by means of adhesive binders, for example polyvinyl alcohol, sodium polyacrylate or else mineral oils. Suitable active compounds can also be granulated in the manner which is customary for the preparation of fertilizer granules, if desired as a mixture with fertilizers.

Water-dispersible granules are generally prepared by the customary processes, such as spray-drying, fluidized-bed granulation, disk granulation, mixing using high-speed mixers, and extrusion without solid inert material. For the preparation of disk, fluidized-bed, extruder and spray granules, see for example processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th Ed., McGraw-Hill, New York 1973, pp. 8–57.

For further details on the formulation of crop protection products, see for example G. C. Klingman, "Weed Control as a Science", John Wiley and Sons Inc., New York, 1961, pages 81–96 and J. D. Freyer, S. A. Evans, "Weed Control Handbook", 5th Ed., Blackwell Scientific Publications, Oxford, 1968, pages 101–103.

The agrochemical formulations generally contain from 0.1 to 99% by weight, in particular from 0.1 to 95% by weight, of active compound of the formula (I). In wettable powders the concentration of active compound is, for example, from about 10 to 90% by weight, the remainder to 100% by weight consisting of customary formulation constituents. In emulsifiable concentrates the concentration of active compound can be from about 1 to 90%, preferably from 5 to 80%, by weight. Formulations in the form of dusts contain from 1 to 30% by weight of active compound, preferably most commonly from 5 to 20% by weight of active compound, while sprayable solutions contain from about 0.05 to 80%, preferably from 2 to 50%, by weight of active compound. In the case of water-dispersible granules the content of active compound depends partly on whether the active compound is in liquid or solid form and on the granulation auxiliaries, fillers, etc. that are used. In water-dispersible granules the content of active compound, for example, is between 1 and 95% by weight, preferably between 10 and 80% by weight.

In addition, said formulations of active compound may comprise the tackifiers, wetting agents, dispersants, emulsifiers, penetrants, preservatives, antifreeze agents, solvents, fillers, carriers, colorants, antifoams, evaporation inhibitors and pH and viscosity regulators which are customary in each case.

Suitable active ingredients which can be combined with the active ingredients according to the invention in mixed formulations or in a tank mix are, for example, known active ingredients as described in for example Weed Research 26, 441–445 (1986), or "The Pesticide Manual", 11th edition, The British Crop Protection Council and the Royal Soc. of Chemistry, 1997 and in the literature cited therein. For example the following active ingredients may be mentioned as herbicides which are known from the literature and which can be combined with the compounds of the formula (I) (note: the compounds are either named by the "common name" in accordance with the International Organization for Standardization (ISO) or by the chemical names, if appropriate together with a customary code number): acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azafenidin; azimsulfurone (DPX-A8947); aziprotryn; barban; BAS 516 H, i.e. 5-fluoro-2-phenyl-4H-3,1-benzoxazin-4-one; BAS 620 H; BAS 65400 H; BAY FOE 5043; benazolin; benfluralin; benfuresate; bensulfuron-methyl; bensulide; bentazone; benzofenap; benzofluor; benzoylprop-ethyl; benzthiazuron; bialaphos; bifenox; bispyribac-Na; bromacil; bromobutide; bromofenoxim; bromoxynil; bromuron; buminafos; busoxinone; butachlor; butamifos; butenachlor; buthidazole; butralin; butroxydim; butylate; cafenstrole (CH-900); caloxydim; carbetamide; cafentrazone ethyl; CDAA, i.e. 2-chloro-N,N-di-2-propenylacetamide; CDEC, i.e. 2-chloroallyl diethyidithio-carbamate; chlomethoxyfen; chloramben; chlorazifop-butyl, chlorbromuron; chlorbufam; chlorfenac; chlorflurecol-methyl; chloridazon; chlorimuron ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cloransulam-methyl; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diclosulam, i.e. N-(2,6-dichlorophenyl)-5-ethoxy-7-fluoro[1,2,4]triazolo[1, 5-c]pyrimidine-2-sulfonamide; diethatyl; difenoxuron; difenzoquat; diflufenican; diflufenzopyr (BAS 654 00H), difemuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)—N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); flupyrsulfuron-methyl-sodium; fluridone; flurochloridone;

fluroxypyr; flurtamone; fluthiacet-methyl; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox; imazapyr; imazaquin and salts such as the ammonium salt; imazethamethapyr; imazethapyr; imazosulfuron; indanofan (MK-243), ioxynil; isocarbamid; isopropalin; isoproturon; isouron; isoxaben; isoxaflutole; isoxapyrifop; karbutilate; lactofen; lenacil; linuron; MCPA; MCPB; mecoprop; mefenacet; mefluidid; metamitron; metazachlor; methabenzthiazuron; metham; methazole; methoxyphenone; methyidymron; metobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, i.e. 6-chloro-N-(3-chloro-2-propenyl)-5-methyl-N-phenyl-3-pyridazin-amine; MT 5950, i.e. N-[3-chloro-4-(1-methylethyl)-phenyl]-2-methyl-pentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxasulfuron; oxaziclomefone (MY-100); oxyfluorfen; paraquat; pebulate; pendimethalin; pentaoxazone (KPP-314); perfluidone; phenisopham; phenmedipham; picloram; piperophos; piributicarb; pirifenopbutyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyroflufen-ethyl; pyrazolinate; pyrazon; pyrazosulfuron-ethyl; pyrazoxyfen; pyribenzoxim (LGC-40836); pyributicarb; pyridate; pyriminobac-methyl; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; sulcotrione; sulfentrazon (FMC-97285, F-6285); sulfazuron; sulfometuron-methyl; sulfosate (ICI-A0224); sulfosulfuron; TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazol-1-carboxamide; thenylchlor (NSK-850); thiazafluron; thiazopyr (Mon-13200); thidiazimin (SN-24085); thifensulfuron-methyl; thiobencarb; tiocarbazil; tralkoxydim; tri-allate; triasulfuron; triaziflam; triazofenamide; tribenuron-methyl; triclopyr; tridiphane; trietazine; trifluralin; triflusulfuron and its esters (for example methyl ester, DPX-66037); trimeturon; tsitodef; vernolate; WL 110547, i.e. 5-phenoxy-1-[3-(trifluoromethyl)phenyl]-1H-tetrazole; JTC-101; UBH-509; D489; LS 82-556; KPP-300; NC-324; NC-330; KH-218; DPX—N8189; SC-0774; DOWCO-535; DK-8910; V-53482; PP600; MBH-001; KIH-9201; ET-751; KIH4127 and KIH-2023.

For use, the formulations which are present in commercially available form are, if appropriate, diluted in the customary manner, for example using water in the case of wettable powders, emulsifiable concentrates, dispersions and water-dispersible granules. Products in the form of dusts, granules for soil application or broadcasting and sprayable solutions are usually not further diluted with other inert substances prior to use.

The application rate of the compounds of the formula (I) required varies with the external conditions, such as temperature, humidity, the nature of the herbicide used and the like. It can vary within wide limits, for example between 0.001 and 10.0 kg/ha or more of active substance, but it is preferably between 0.005 and 5 kg/ha.

A. CHEMICAL EXAMPLES

Example A1

Dimethyl chlorosulfonylterephthalate

At 10° C., a solution of 36.2 g (0.52 mol) of sodium nitrite in 100 ml of water was added over a period of approximately 20 minutes to a solution of 104.6 g (0.5 mol) of dimethyl aminoterephthalate in 500 ml of glacial acetic acid and 165 ml of conc. hydrochloric acid. The mixture was stirred at this temperature for another 10 min, small amounts of undissolved material were filtered off and the filtrate was added dropwise at 15–20° C. and over a period of 35 min to a solution which had been prepared as follows: At room temperature, 8.5 g (0.1 mol) of $CuCl_2$ in 100 ml of water were added dropwise to 360 ml of conc. hydrochloric acid, and the mixture was cooled to 5° C. A solution of 118.8 g (0.625 mol) of $Na_2S_2O_5$ in 180 ml of water was added dropwise to this mixture.

After addition of the diazonium salt solution, the mixture was stirred at 15–20° C. for another 30 min and subsequently poured into 2 l of ice-water. The mixture was extracted with diethyl ether and the ether phase was washed with water, dried and concentrated, giving 118.3 g (81% of theory) of dimethyl chlorosulfonylterephthalate as a brown oil which was used for the following reaction without purification.

Example A2

Dimethyl tert-butylsulfamoylterephthalate

At 5° C., 59.1 g (0.81 mol) of tert-butylamine were added dropwise to a solution of 118.3 g (0.4 mol) of crude dimethyl chlorosulfonylterephthalate (from Example A1) in 500 ml of dichloromethane, and the mixture was stirred at room temperature for another 1 h. The reaction solution was washed with water, dried and concentrated. Trituration of the crude product with heptane gave 106.7 g (81% of theory) of dimethyl tert-butylsulfamoylterephthalate of m.p. 132–134° C.

Example A3 tert-Butylsulfamoylterephthalic acid

At 50° C., 45.0 g (1.13 mol) of sodium hydroxide in 600 ml of water were added dropwise to a solution of 106.0 g (0.32 mol) of dimethyl tert-butylsulfamoylterephthalate in 1600 ml of methanol. The mixture was stirred at reflux temperature for 2 h and evaporated, the residue was taken up in approximately 500 ml of water and a pH of 1 was established using conc. hydrochloric acid. The precipitated solid was filtered off with suction and dried. This gave 87.4 g (90% of theory) of tert-butylsulfamoylterephthalic acid of m.p. 210–213° C.

Example A4

2-tert-Butylsaccharin-6-carbonyl chloride 15.0 g of (0.05 mol) of tert-butylsulfamoylterephthalic acid in 95 ml of thionyl chloride were heated under reflux for 8 h. The mixture was concentrated and the residue was triturated with ethyl acetate. This gave 14.6 g (97% of theory) of 2-tert-butylsaccharin-6-carbonyl chloride of m.p. 185–186° C.

Example A5
N-isopropyl-2-tert-butylsaccharin-6-carboxamide

At 10° C., 2.6 g (0.044 mol) of isopropylamine were added dropwise to 6.0 g (0.02 mol) of 2-tert-butylsaccharin-6-carbonyl chloride in 30 ml of THF, and the mixture was stirred at 10–15° C. for another 3 h. The mixture was poured into water and extracted with dichloromethane and the organic phase was washed with water, dried and concentrated. This gave 5.6 g (86% of theory) of N-isopropyl-2-tert-butylsaccharin-6-carboxamide of m.p. 152–154° C.

Example A6
Methyl 2-tert-butylsulfamoyl-4-isopropylcarbamoylbenzoate 22.0 g (0.068 mol) of N-isopropyl-2-tert-butylsaccharinn-carboxamide were added to a solution of 1.56 g (0.068 mol) of sodium in 250 ml of abs. methanol and the mixture was stirred at room temperature for 5 h. The mixture was concentrated, the residue was taken up in dichloromethane and the solution was washed with 2N HCl and water, dried and concentrated. This gave 20.8 g (86% of theory) of methyl 2-tert-butylsulfamoyl-4-isopropylcarbamoylbenzoate of m.p. 159 to 160° C.

Example A7
Methyl 4-isopropylcarbamoyl-2-sulfamoylbenzoate

At room temperature, 19.6 g (0.055 mol) of methyl 2-tert-butylsulfamoyl-4-isopropylcarbamoylbenzoate were stirred in 200 ml of trifluoroacetic acid for 3 h. The mixture was concentrated and the residue was triturated with diethyl ether and filtered off. This gave 15.6 g (95% of theory) of methyl 4-isopropylcarbamoyl-2-sulfamoylbenzoate of m.p. 203–205° C.

Example A8
Methyl 2-[3-(4,6-dimethoxypyrimidin-2-yl)ureidosulfonyl]-4-isopropyl-carbamoylbenzoate 2.6 g (8.6 mmol) of methyl 4-isopropylcarbamoyl-2-sulfamoylbenzoate and 2.8 g (10.3 mmol) of phenyl N-(4,6-dimethoxypyrimidin-2-yl)carbamate were initially charged in 50 ml of acetonitrile. At room temperature, 2.9 g (19 mmol) of 1,8-diazabicyclo[5.4.0]undec-7-ene (DBU) were added dropwise, and the mixture was stirred at this temperature for 3 h. The mixture was poured into ice-water and the pH was adjusted to 1 using 2N hydrochloric acid. The precipitated solid was filtered off with suction and washed with water. After drying, 3.9 g (94% of theory) of methyl 2-[3-(4,6-dimethoxypyrimidin-2-yl)ureidosulfonyl]-4-isopropylcarbamoylbenzoate of m.p. 149–151° C. (decomp.) were obtained.

Example A9
Methyl 2-[3-(4,6-dimethoxypyrimidin-2-yl)ureidosulfonyl]-4-pyrrolidinocarbonylbenzoate, sodium salt Similarly to Examples A5 to A8, and using pyrrolidine as amine in Example A5, methyl 2-[3-(4,6-dimethoxypyrimidin-2-yl)ureidosulfonyl]-4-pyrrolidinocarbonylbenzoate was prepared first. 0.2 g (1.1 mmol) of a 30% strength sodium methoxide solution in methanol was subsequently added dropwise to 0.5 g (1.0 mmol) of this compound in 15 ml of methanol at room temperature. The mixture was stirred at room temperature for 2 h and filtered off with suction, and the residue was washed with methanol and dried. This gave 0.5 g (96% of theory) of methyl 2-[3-(4,6-dimethoxypyrimidin-2-yl)-ureidosulfonyl]-4-pyrrolidinocarbonylbenzoate, sodium salt, of m.p. 233–235° C. (decomp.).

Example A 10
N,N-dimethyl-2-tert-butylsulfamoyl-4-carbamoylbenzamide

Similarly to Examples A5 to A6, and using ammonia as basic reagent in Example A5, methyl 2-tert-butylsulfamoyl-4-carbamoylbenzoate was prepared first. At room temperature, 3.0 g (0.01 mol) of this compound were subsequently added to a solution of 45 g (1.0 mol) of dimethylamine in 60 ml of methanol, and the reaction mixture was left standing at room temperature for 7 h. The mixture was concentrated and the desired product was isolated by silica gel column chromatography (mobile phase: ethyl acetate; $R_f$≈0.2). This gave 1.0 g (31% of theory) of N,N-dimethyl-2-tert-butylsulfamoyl-4-carbamoylbenzamide of a glass-like consistency.

Example A11
N,N-dimethyl-4-carbamoyl-2-sulfamoylbenzamide

At room temperature, 1.0 g (3.1 mmol) of N,N-dimethyl-2-tert-butylsulfamoyl-4-carbamoylbenzamide in 10 ml of trifluoroacetic acid was stirred for 2.5 h. The mixture was concentrated and the residue was triturated with diethyl ether, filtered off with suction and dried. This gave 0.53 g (63% of theory) of N,N-dimethyl-4-carbamoyl-2- sulfamoylbenzamide of m.p. 202–205° C.

Example A12
N,N-dimethyl-2-[3-(4,6-dimethoxypyrimidin-2-yl) ureidosulfonyl]-4-carbamoylbenzamide 0.53 g (2.0 mmol) of N,N-dimethyl-4-carbamoyl-2-sulfamoylbenzamide and 0.59 g (2.2 mmol) of phenyl N-(2,4-dimethoxypyrimidin-2-yl)carbamate were initially charged in 15 ml of acetonitrile. At room temperature, 0.39 g (2.5 mmol) of 1,8-diazabicyclo[5.4.0]undec-7-ene (DBU) were added dropwise, and the mixture was stirred at this temperature for 3 h. The mixture was poured into water and a pH of approximately 2 was established using 2 N hydrochloric acid. The aqueous phase was extracted three times with $CH_2Cl_2$. The organic phase was washed with 2 N hydrochloric acid and water, dried and concentrated. The residue was triturated with diisopropyl ether. The mixture was filtered off with suction and dried, giving 0.60 g (67% of theory) of N,N-dimethyl-2-[3-(4,6-dimethoxypyrimidin-2-yl)ureidosulfonyl]-4-carbamoylbenzamide of m.p. 194–196° C. (decomp.).

Example A13
N-Allylisopropylamine 20.7 g (0.35 mol) of isopropylamine were added dropwise to a solution of 8.0 g (0.2 mol) of sodium hydroxide in 25 ml of water. The mixture was subsequently admixed dropwise over a period of 1 h with 15.3 g (0.2 mol) of allyl chloride, and the temperature was kept at 35–40° C. during this time. The mixture was heated at 60° C. for a further 2.5 h and then allowed to cool. For work-up, the phases were separated and the aqueous phase was extracted with ether. The organic phases were combined, dried over sodium hydroxide, decantered and distilled. This gave 9.6 g (48% of theory) of colorless N-allylisopropylamine of b.p. 96–98° C.

Example A14
2-tert-Butylsulfamoyl-4-dimethylcarbamoylbenzoic acid, potassium salt At 25° C. and with stirring, 254 ml of a 0.25 M aqueous solution of potassium hydroxide were poured into a solution of 19.7 g (63.5 mmol) of 2-tert-butylsaccharin-6-dimethylamide in 235 ml of ethanol. The mixture was subsequently heated under reflux for 6 h, and then allowed to cool and evaporated to dryness. This gave 23.3 g (100% of theory) of 2-tert-butylsulfamoyl-4-dimethylcarbamoylbenzoic acid, potassium salt, of m.p. >260° C. as a colorless solid.

Example A15
Ethyl 2-tert-butylsulfamoyl-4-dimethylcarbamoylbenzoate

A suspension of 3.0 g (8.2 mmol) of the potassium salt of 2-tert-butylsulfamoyl-4-dimethylcarbamoylbenzoic acid, and 0.21 g (0.79 mmol) of 1,4,7,10,13,16-hexaoxacyclooctane in 25 ml of acetonitrile was stirred at room temperature for half an hour, and 890 mg (8.2 mmol) of bromoethane were then added. The mixture was subsequently heated under reflux for 6 h and then allowed to cool to room temperature. For work-up, the reaction mixture was diluted with ethyl acetate and extracted with 1 M aqueous hydrochloric acid solution, saturated aqueous sodium bicarbonate solution and water. The organic phase was dried over sodium sulfate, filtered off and concentrated. This gave 2.31 g (79% of theory) of ethyl 2-tert-butylsulfamoyl-4-dimethylcarbamoylbenzoate as a colorless solid of m.p. 101 to 102.5° C.

The compounds described in Tables 1 and 2 below are obtained by or similar to the Examples A1–A15 above.

Abbreviations in Tables 1 and 2:

m.p.=melting point in ° C.

(D)=melting point with decomposition

Bu=n-butyl; correspondingly pentyl=n-pentyl, hexyl=n-hexyl

Et=ethyl

Me=methyl

Ph=phenyl

Pr, i-Pr, c-Pr=n-propyl, isopropyl and cyclopropyl, respectively A diradical such as butylene of the formula

in the columns for $R^2$, $R^3$ means that $R^2$ and $R^3$ together are the diradical bridge and, together with the nitrogen atom of the group $R^2R^3N$, form a cyclic amine.

T1 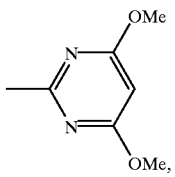

T2 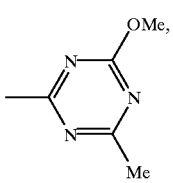

T3 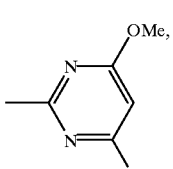

T4 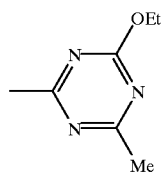

T5 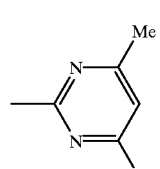

T6 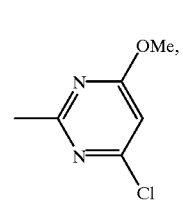

T7 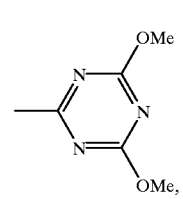

T8 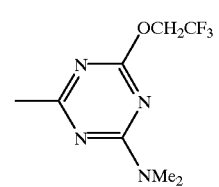

T9 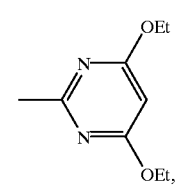

T10 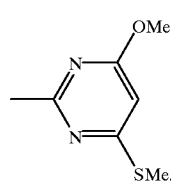

T11 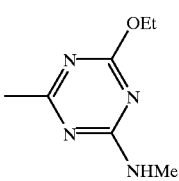

-continued

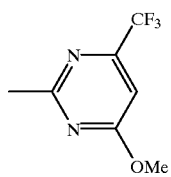
T12

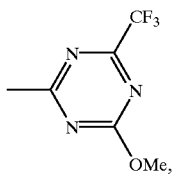
T13

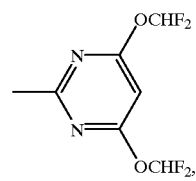
T14

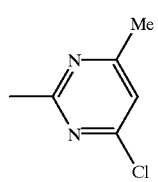
T15

Het = heterocycle, where Het denotes one of the radicals T1 to T15

TABLE 1

Compounds of the formula (Ia)

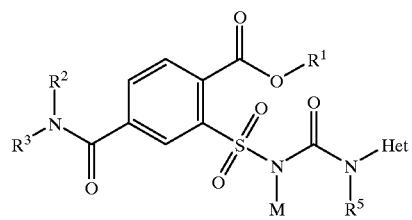

(Ia)

| Ex. | $R^1$ | $R^2$ | $R^3$ | $R^5$ | M | Het | m.p. |
|---|---|---|---|---|---|---|---|
| 1. | Me | H | H | H | H | T1 | 129–132(D) |
| 2. | Me | H | H | H | Na | T1 | 262–264(D) |
| 3. | Me | H | H | H | H | T2 | 154–156(D) |
| 4. | Me | H | H | H | Na | T2 | 219–221(D) |
| 5. | Me | H | H | H | H | T3 | |
| 6. | Me | H | H | H | Na | T3 | |
| 9. | Me | H | H | H | H | T5 | |
| 10. | Me | H | H | H | Na | T5 | |
| 11. | Me | H | H | H | H | T6 | 113–115(D) |
| 12. | Me | H | H | H | Na | T6 | 182–184(D) |
| 13. | Me | H | H | H | H | T7 | 169–172(D) |
| 14. | Me | H | H | H | Na | T7 | 194–196(D) |
| 15. | Me | H | H | H | H | T8 | |
| 16. | Me | H | H | H | Na | T8 | |
| 17. | Me | H | H | H | H | T9 | |
| 18. | Me | H | H | H | Na | T9 | |
| 19. | Me | H | H | H | H | T10 | |
| 20. | Me | H | H | H | Na | T10 | |
| 21. | Me | H | H | H | H | T11 | |
| 22. | Me | H | H | H | Na | T11 | |
| 23. | Me | H | H | H | H | T12 | |
| 24. | Me | H | H | H | Na | T12 | |
| 25. | Me | H | H | H | H | T13 | |
| 26. | Me | H | H | H | Na | T13 | |
| 27. | Me | H | H | H | H | T14 | |
| 28. | Me | H | H | H | Na | T14 | |
| 29. | Me | H | H | H | H | T15 | |
| 30. | Me | H | H | H | Na | T15 | |
| 31. | Me | Me | H | H | H | T1 | 119–122(D) |
| 32. | Me | Me | H | H | Na | T1 | 249–251(D) |
| 33. | Me | Me | H | H | H | T2 | 175–177(D) |
| 34. | Me | Me | H | H | Na | T2 | 113–116(D) |
| 35. | Me | Me | H | H | H | T3 | |
| 36. | Me | Me | H | H | Na | T3 | |
| 37. | Me | Me | H | H | H | T4 | |
| 38. | Me | Me | H | H | Na | T4 | |
| 39. | Me | Me | H | H | H | T5 | |

TABLE 1-continued

Compounds of the formula (Ia)

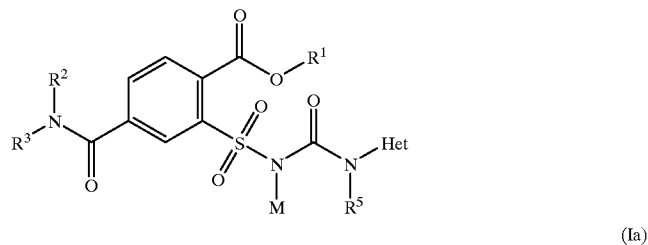

(Ia)

| Ex. | R¹ | R² | R³ | R⁵ | M | Het | m.p. |
|---|---|---|---|---|---|---|---|
| 40. | Me | Me | H | H | Na | T5 | |
| 41. | Me | Me | H | H | H | T6 | 119–121(D) |
| 42. | Me | Me | H | H | Na | T6 | 186–188(D) |
| 43. | Me | Me | H | H | H | T7 | 158–160(D) |
| 44. | Me | Me | H | H | Na | T7 | 219–221(D) |
| 45. | Me | Me | H | H | H | T8 | |
| 46. | Me | Me | H | H | Na | T8 | |
| 47. | Me | Me | H | H | H | T9 | |
| 48. | Me | Me | H | H | Na | T9 | |
| 49. | Me | Me | H | H | H | T10 | |
| 50. | Me | Me | H | H | Na | T10 | |
| 51. | Me | Me | H | H | H | T11 | |
| 52. | Me | Me | H | H | Na | T11 | |
| 53. | Me | Me | H | H | H | T12 | |
| 54. | Me | Me | H | H | Na | T12 | |
| 55. | Me | Me | H | H | H | T13 | |
| 56. | Me | Me | H | H | Na | T13 | |
| 57. | Me | Me | H | H | H | T14 | |
| 58. | Me | Me | H | H | Na | T14 | |
| 59. | Me | Me | H | H | H | T15 | |
| 60. | Me | Me | H | H | Na | T15 | |
| 61. | Me | Et | H | H | H | T1 | 179–181(D) |
| 62. | Me | Et | H | H | Na | T1 | 189–192(D) |
| 63. | Me | Et | H | H | H | T2 | 150–152(D) |
| 64. | Me | Et | H | H | Na | T2 | 186–188(D) |
| 65. | Me | Et | H | H | H | T3 | |
| 66. | Me | Et | H | H | Na | T3 | |
| 67. | Me | Et | H | H | H | T4 | |
| 68. | Me | Et | H | H | Na | T4 | |
| 69. | Me | Et | H | H | H | T5 | |
| 70. | Me | Et | H | H | Na | T5 | |
| 71. | Me | Et | H | H | H | T6 | 113–115(D) |
| 72. | Me | Et | H | H | Na | T6 | 180–182(D) |
| 73. | Me | Et | H | H | H | T7 | |
| 74. | Me | Et | H | H | Na | T7 | |
| 75. | Me | Et | H | H | H | T8 | |
| 76. | Me | Et | H | H | Na | T8 | |
| 77. | Me | Et | H | H | H | T9 | |
| 78. | Me | Et | H | H | Na | T9 | |
| 79. | Me | Et | H | H | H | T10 | |
| 80. | Me | Et | H | H | Na | T10 | |
| 81. | Me | Et | H | H | H | T11 | |
| 82. | Me | Et | H | H | Na | T11 | |
| 83. | Me | Et | H | H | H | T12 | |
| 84. | Me | Et | H | H | Na | T12 | |
| 85. | Me | Et | H | H | H | T13 | |
| 86. | Me | Et | H | H | Na | T13 | |
| 87. | Me | Et | H | H | H | T14 | |
| 88. | Me | Et | H | H | Na | T14 | |
| 89. | Me | Et | H | H | H | T15 | |
| 90. | Me | i-Pr | H | H | Na | T15 | |
| 91. | Me | i-Pr | H | H | H | T1 | 149–151(D) |
| 92. | Me | i-Pr | H | H | Na | T1 | 272–176(D) |
| 93. | Me | i-Pr | H | H | H | T2 | 106–108(D) |
| 94. | Me | i-Pr | H | H | Na | T2 | 185–187(D) |
| 95. | Me | i-Pr | H | H | H | T3 | |
| 96. | Me | i-Pr | H | H | Na | T3 | |
| 97. | Me | i-Pr | H | H | H | T4 | |
| 98. | Me | i-Pr | H | H | Na | T4 | |
| 99. | Me | i-Pr | H | H | H | T5 | |
| 100. | Me | i-Pr | H | H | Na | T5 | |
| 101. | Me | i-Pr | H | H | H | T6 | 109–111(D) |

TABLE 1-continued

Compounds of the formula (Ia)

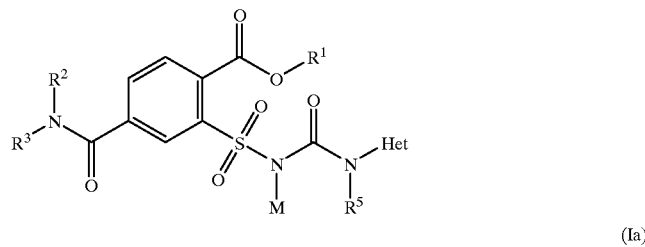

(Ia)

| Ex. | R¹ | R² | R³ | R⁵ | M | Het | m.p. |
|---|---|---|---|---|---|---|---|
| 102. | Me | i-Pr | H | H | Na | T6 | 173–178(D) |
| 103. | Me | i-Pr | H | H | H | T7 | 160–162(D) |
| 104. | Me | i-Pr | H | H | Na | T7 | 188–191(D) |
| 105. | Me | i-Pr | H | H | H | T8 | |
| 106. | Me | i-Pr | H | H | Na | T8 | |
| 107. | Me | i-Pr | H | H | H | T9 | |
| 108. | Me | i-Pr | H | H | Na | T9 | |
| 109. | Me | i-Pr | H | H | H | T10 | |
| 110. | Me | i-Pr | H | H | Na | T10 | |
| 111. | Me | Pr | H | H | H | T1 | |
| 112. | Me | Pr | H | H | Na | T1 | |
| 113. | Me | Pr | H | H | H | T2 | |
| 114. | Me | Pr | H | H | Na | T2 | |
| 115. | Me | Pr | H | H | H | T3 | |
| 116. | Me | Pr | H | H | Na | T3 | |
| 117. | Me | Pr | H | H | H | T6 | |
| 118. | Me | Pr | H | H | Na | T6 | |
| 119. | Me | Pr | H | H | H | T7 | |
| 120. | Me | Pr | H | H | Na | T7 | |
| 121. | Me | Allyl | H | H | H | T1 | 114–117(D) |
| 122. | Me | Allyl | H | H | Na | T1 | 186–190(D) |
| 123. | Me | Allyl | H | H | H | T2 | 167–169(D) |
| 124. | Me | Allyl | H | H | Na | T2 | 183–185(D) |
| 125. | Me | Allyl | H | H | H | T3 | |
| 126. | Me | Allyl | H | H | Na | T3 | |
| 127. | Me | Allyl | H | H | H | T4 | |
| 128. | Me | Allyl | H | H | Na | T4 | |
| 129. | Me | Allyl | H | H | H | T5 | |
| 130. | Me | Allyl | H | H | Na | T5 | |
| 131. | Me | Allyl | H | H | H | T6 | 96–98(D) |
| 132. | Me | Allyl | H | H | Na | T6 | 172–174(D) |
| 133. | Me | Allyl | H | H | H | T7 | 146–148(D) |
| 134. | Me | Allyl | H | H | Na | T7 | 168–170(D) |
| 135. | Me | Allyl | H | H | H | T8 | |
| 136. | Me | Allyl | H | H | Na | T8 | |
| 137. | Me | Allyl | H | H | H | T9 | |
| 138. | Me | Allyl | H | H | Na | T9 | |
| 139. | Me | Allyl | H | H | H | T10 | |
| 140. | Me | Allyl | H | H | Na | T10 | |
| 141. | Me | Allyl | H | H | H | T11 | |
| 142. | Me | Allyl | H | H | Na | T11 | |
| 143. | Me | Allyl | H | H | H | T12 | |
| 144. | Me | Allyl | H | H | Na | T12 | |
| 145. | Me | Allyl | H | H | H | T13 | |
| 146. | Me | Allyl | H | H | Na | T13 | |
| 147. | Me | Allyl | H | H | H | T14 | |
| 148. | Me | Allyl | H | H | Na | T14 | |
| 149. | Me | Allyl | H | H | H | T15 | |
| 150. | Me | Allyl | H | H | Na | T15 | |
| 151. | Me | Propargyl | H | H | H | T1 | 119–121(D) |
| 152. | Me | Propargyl | H | H | Na | T1 | 234–237(D) |
| 153. | Me | Propargyl | H | H | H | T2 | |
| 154. | Me | Propargyl | H | H | Na | T2 | |
| 155. | Me | Propargyl | H | H | H | T3 | |
| 156. | Me | Propargyl | H | H | Na | T3 | |
| 157. | Me | Propargyl | H | H | H | T4 | |
| 158. | Me | Propargyl | H | H | Na | T4 | |
| 159. | Me | Propargyl | H | H | H | T5 | |
| 160. | Me | Propargyl | H | H | Na | T5 | |
| 161. | Me | Propargyl | H | H | H | T6 | |
| 162. | Me | Propargyl | H | H | Na | T6 | |
| 163. | Me | Propargyl | H | H | H | T7 | |

TABLE 1-continued

Compounds of the formula (Ia)

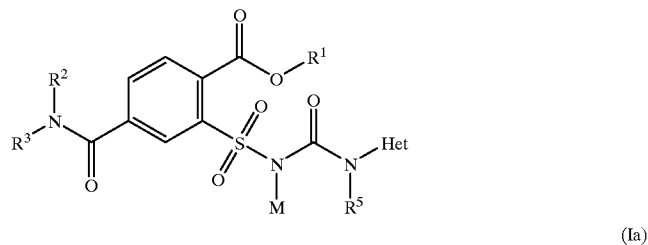

(Ia)

| Ex. | R¹ | R² | R³ | R⁵ | M | Het | m.p. |
|---|---|---|---|---|---|---|---|
| 164. | Me | Propargyl | H | H | Na | T7 | |
| 165. | Me | Propargyl | H | H | H | T8 | |
| 166. | Me | Propargyl | H | H | Na | T8 | |
| 167. | Me | Propargyl | H | H | H | T9 | |
| 168. | Me | Propargyl | H | H | Na | T9 | |
| 169. | Me | Propargyl | H | H | H | T10 | |
| 170. | Me | Propargyl | H | H | Na | T10 | |
| 171. | Me | Propargyl | H | H | H | T11 | |
| 172. | Me | Propargyl | H | H | Na | T11 | |
| 173. | Me | Propargyl | H | H | H | T12 | |
| 174. | Me | Propargyl | H | H | Na | T12 | |
| 175. | Me | Propargyl | H | H | H | T13 | |
| 176. | Me | Propargyl | H | H | Na | T13 | |
| 177. | Me | Propargyl | H | H | H | T14 | |
| 178. | Me | Propargyl | H | H | Na | T14 | |
| 179. | Me | Propargyl | H | H | H | T15 | |
| 180. | Me | Propargyl | H | H | Na | T15 | |
| 181. | Me | CH₂=CHCHMe | H | H | H | T1 | |
| 182. | Me | CH₂=CHCHMe | H | H | Na | T1 | |
| 183. | Me | CH₂=CHCHMe | H | H | H | T2 | |
| 184. | Me | CH₂=CHCHMe | H | H | Na | T2 | |
| 185. | Me | CH₂=CHCHMe | H | H | H | T3 | |
| 186. | Me | CH₂=CHCHMe | H | H | Na | T3 | |
| 187. | Me | CH₂=CHCHMe | H | H | H | T4 | |
| 188. | Me | CH₂=CHCHMe | H | H | Na | T4 | |
| 189. | Me | CH₂=CHCHMe | H | H | H | T5 | |
| 190. | Me | CH₂=CHCHMe | H | H | Na | T5 | |
| 191. | Me | CH₂=CHCHMe | H | H | H | T6 | |
| 192. | Me | CH₂=CHCHMe | H | H | Na | T6 | |
| 193. | Me | CH₂=CHCHMe | H | H | H | T7 | |
| 194. | Me | CH₂=CHCHMe | H | H | Na | T7 | |
| 195. | Me | CH₂=CHCHMe | H | H | H | T8 | |
| 196. | Me | CH₂=CHCHMe | H | H | Na | T8 | |
| 197. | Me | CH₂=CHCHMe | H | H | H | T9 | |
| 198. | Me | CH₂=CHCHMe | H | H | Na | T9 | |
| 199. | Me | CH₂=CHCHMe | H | H | H | T10 | |
| 200. | Me | CH₂=CHCHMe | H | H | Na | T10 | |
| 201. | Me | CH₂=CHCHMe | H | H | H | T11 | |
| 202. | Me | CH₂=CHCHMe | H | H | Na | T11 | |
| 203. | Me | CH₂=CHCHMe | H | H | H | T12 | |
| 204. | Me | CH₂=CHCHMe | H | H | Na | T12 | |
| 205. | Me | CH₂=CHCHMe | H | H | H | T13 | |
| 206. | Me | CH₂=CHCHMe | H | H | Na | T13 | |
| 207. | Me | CH₂=CHCHMe | H | H | H | T14 | |
| 208. | Me | CH₂=CHCHMe | H | H | Na | T14 | |
| 209. | Me | CH₂=CHCHMe | H | H | H | T15 | |
| 210. | Me | CH₂=CHCHMe | H | H | Na | T15 | |
| 211. | Me | MeCH=CHCH₂ | H | H | H | T1 | |
| 212. | Me | MeCH=CHCH₂ | H | H | Na | T1 | |
| 213. | Me | MeCH=CHCH₂ | H | H | H | T2 | |
| 214. | Me | MeCH=CHCH₂ | H | H | Na | T2 | |
| 215. | Me | MeCH=CHCH₂ | H | H | H | T3 | |
| 216. | Me | MeCH=CHCH₂ | H | H | Na | T3 | |
| 217. | Me | MeCH=CHCH₂ | H | H | H | T4 | |
| 218. | Me | MeCH=CHCH₂ | H | H | Na | T4 | |
| 219. | Me | MeCH=CHCH₂ | H | H | H | T5 | |
| 220. | Me | MeCH=CHCH₂ | H | H | Na | T5 | |
| 221. | Me | MeCH=CHCH₂ | H | H | H | T6 | |
| 222. | Me | MeCH=CHCH₂ | H | H | Na | T6 | |
| 223. | Me | MeCH=CHCH₂ | H | H | H | T7 | |
| 224. | Me | MeCH=CHCH₂ | H | H | Na | T7 | |
| 225. | Me | MeCH=CHCH₂ | H | H | H | T8 | |

TABLE 1-continued

Compounds of the formula (Ia)

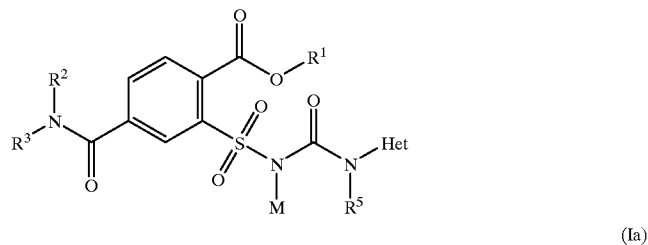

(Ia)

| Ex. | R¹ | R² | R³ | R⁵ | M | Het | m.p. |
|---|---|---|---|---|---|---|---|
| 226. | Me | MeCH=CHCH₂ | H | H | Na | T8 | |
| 227. | Me | MeCH=CHCH₂ | H | H | H | T9 | |
| 228. | Me | MeCH=CHCH₂ | H | H | Na | T9 | |
| 229. | Me | MeCH=CHCH₂ | H | H | H | T10 | |
| 230. | Me | MeCH=CHCH₂ | H | H | Na | T10 | |
| 231. | Me | MeCH=CHCH₂ | H | H | H | T11 | |
| 232. | Me | MeCH=CHCH₂ | H | H | Na | T11 | |
| 233. | Me | MeCH=CHCH₂ | H | H | H | T12 | |
| 234. | Me | MeCH=CHCH₂ | H | H | Na | T12 | |
| 235. | Me | MeCH=CHCH₂ | H | H | H | T13 | |
| 236. | Me | MeCH=CHCH₂ | H | H | Na | T13 | |
| 237. | Me | MeCH=CHCH₂ | H | H | H | T14 | |
| 238. | Me | MeCH=CHCH₂ | H | H | Na | T14 | |
| 239. | Me | MeCH=CHCH₂ | H | H | H | T15 | |
| 240. | Me | MeCH=CHCH₂ | H | H | Na | T15 | |
| 241. | Me | CH₂=CMeCH₂ | H | H | H | T1 | |
| 242. | Me | CH₂=CMeCH₂ | H | H | Na | T1 | |
| 243. | Me | CH₂=CMeCH₂ | H | H | H | T2 | |
| 244. | Me | CH₂=CMeCH₂ | H | H | Na | T2 | |
| 245. | Me | CH₂=CMeCH₂ | H | H | H | T3 | |
| 246. | Me | CH₂=CMeCH₂ | H | H | Na | T3 | |
| 247. | Me | CH₂=CMeCH₂ | H | H | H | T4 | |
| 248. | Me | CH₂=CMeCH₂ | H | H | Na | T4 | |
| 249. | Me | CH₂=CMeCH₂ | H | H | H | T5 | |
| 250. | Me | CH₂=CMeCH₂ | H | H | Na | T5 | |
| 251. | Me | CH₂=CMeCH₂ | H | H | H | T6 | |
| 252. | Me | CH₂=CMeCH₂ | H | H | Na | T6 | |
| 253. | Me | CH₂=CMeCH₂ | H | H | H | T7 | |
| 254. | Me | CH₂=CMeCH₂ | H | H | Na | T7 | |
| 255. | Me | CH₂=CMeCH₂ | H | H | H | T8 | |
| 256. | Me | CH₂=CMeCH₂ | H | H | Na | T8 | |
| 257. | Me | CH₂=CMeCH₂ | H | H | H | T9 | |
| 258. | Me | CH₂=CMeCH₂ | H | H | Na | T9 | |
| 259. | Me | CH₂=CMeCH₂ | H | H | H | T10 | |
| 260. | Me | CH₂=CMeCH₂ | H | H | Na | T10 | |
| 261. | Me | CH₂=CMeCH₂ | H | H | H | T11 | |
| 262. | Me | CH₂=CMeCH₂ | H | H | Na | T11 | |
| 263. | Me | CH₂=CMeCH₂ | H | H | H | T12 | |
| 264. | Me | CH₂=CMeCH₂ | H | H | Na | T12 | |
| 265. | Me | CH₂=CMeCH₂ | H | H | H | T13 | |
| 266. | Me | CH₂=CMeCH₂ | H | H | Na | T13 | |
| 267. | Me | CH₂=CMeCH₂ | H | H | H | T14 | |
| 268. | Me | CH₂=CMeCH₂ | H | H | Na | T14 | |
| 269. | Me | CH₂=CMeCH₂ | H | H | H | T15 | |
| 270. | Me | CH₂=CMeCH₂ | H | H | Na | T15 | |
| 271. | Me | Me | Me | H | H | T1 | 92–94(D) |
| 272. | Me | Me | Me | H | Na | T1 | glasslike |
| 273. | Me | Me | Me | H | H | T2 | 163–165(D) |
| 274. | Me | Me | Me | H | Na | T2 | 139–141(D) |
| 275. | Me | Me | Me | H | H | T3 | |
| 276. | Me | Me | Me | H | Na | T3 | |
| 277. | Me | Me | Me | H | H | T4 | |
| 278. | Me | Me | Me | H | Na | T4 | |
| 279. | Me | Me | Me | H | H | T5 | |
| 280. | Me | Me | Me | H | Na | T5 | |
| 281. | Me | Me | Me | H | H | T6 | |
| 282. | Me | Me | Me | H | Na | T6 | |
| 283. | Me | Me | Me | H | H | T7 | |
| 284. | Me | Me | Me | H | Na | T7 | |
| 285. | Me | Me | Me | H | H | T8 | |
| 286. | Me | Me | Me | H | Na | T8 | |
| 287. | Me | Me | Me | H | H | T9 | |

TABLE 1-continued

Compounds of the formula (Ia)

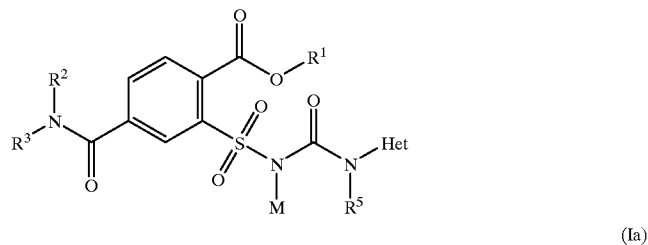

(Ia)

| Ex. | R¹ | R² | R³ | R⁵ | M | Het | m.p. |
|---|---|---|---|---|---|---|---|
| 288. | Me | Me | Me | H | Na | T9 | |
| 289. | Me | Me | Me | H | H | T10 | |
| 290. | Me | Me | Me | H | Na | T10 | |
| 291. | Me | Me | Me | H | H | T11 | |
| 292. | Me | Me | Me | H | Na | T11 | |
| 293. | Me | Me | Me | H | H | T12 | |
| 294. | Me | Me | Me | H | Na | T12 | |
| 295. | Me | Me | Me | H | H | T13 | |
| 296. | Me | Me | Me | H | Na | T13 | |
| 297. | Me | Me | Me | H | H | T14 | |
| 298. | Me | Me | Me | H | Na | T14 | |
| 299. | Me | Me | Me | H | H | T15 | |
| 300. | Me | Me | Me | H | Na | T15 | |
| 301. | Me | CH₂CH₂F | H | H | H | T1 | 129–131(D) |
| 302. | Me | CH₂CH₂F | H | H | Na | T1 | 168–170(D) |
| 303. | Me | CH₂CH₂F | H | H | H | T2 | |
| 304. | Me | CH₂CH₂F | H | H | Na | T2 | |
| 305. | Me | CH₂CH₂F | H | H | H | T3 | |
| 306. | Me | CH₂CH₂F | H | H | Na | T3 | |
| 307. | Me | CH₂CH₂F | H | H | H | T4 | |
| 308. | Me | CH₂CH₂F | H | H | Na | T4 | |
| 309. | Me | CH₂CH₂F | H | H | H | T5 | |
| 310. | Me | CH₂CH₂F | H | H | Na | T5 | |
| 311. | Me | CH₂CH₂F | H | H | H | T6 | |
| 312. | Me | CH₂CH₂F | H | H | Na | T6 | |
| 313. | Me | CH₂CH₂F | H | H | H | T7 | |
| 314. | Me | CH₂CH₂F | H | H | Na | T7 | |
| 315. | Me | CH₂CH₂F | H | H | H | T8 | |
| 316. | Me | CH₂CH₂F | H | H | Na | T8 | |
| 317. | Me | CH₂CH₂F | H | H | H | T9 | |
| 318. | Me | CH₂CH₂F | H | H | Na | T9 | |
| 319. | Me | CH₂CH₂F | H | H | H | T10 | |
| 320. | Me | CH₂CH₂F | H | H | Na | T10 | |
| 321. | Me | CH₂CH₂F | H | H | H | T11 | |
| 322. | Me | CH₂CH₂F | H | H | Na | T11 | |
| 323. | Me | CH₂CH₂F | H | H | H | T12 | |
| 324. | Me | CH₂CH₂F | H | H | Na | T12 | |
| 325. | Me | CH₂CH₂F | H | H | H | T13 | |
| 326. | Me | CH₂CH₂F | H | H | Na | T13 | |
| 327. | Me | CH₂CH₂F | H | H | H | T14 | |
| 328. | Me | CH₂CH₂F | H | H | Na | T14 | |
| 329. | Me | CH₂CH₂F | H | H | H | T15 | |
| 330. | Me | CH₂CH₂F | H | H | Na | T15 | |
| 331. | Me | CH₂CF₃ | H | H | H | T1 | 121–123(D) |
| 332. | Me | CH₂CF₃ | H | H | Na | T1 | |
| 333. | Me | CH₂CF₃ | H | H | H | T2 | |
| 334. | Me | CH₂CF₃ | H | H | Na | T2 | |
| 335. | Me | CH₂CF₃ | H | H | H | T3 | |
| 336. | Me | CH₂CF₃ | H | H | Na | T3 | |
| 337. | Me | CH₂CF₃ | H | H | H | T4 | |
| 338. | Me | CH₂CF₃ | H | H | Na | T4 | |
| 339. | Me | CH₂CF₃ | H | H | H | T5 | |
| 340. | Me | CH₂CF₃ | H | H | Na | T5 | |
| 341. | Me | CH₂CF₃ | H | H | H | T6 | |
| 342. | Me | CH₂CF₃ | H | H | Na | T6 | |
| 343. | Me | CH₂CF₃ | H | H | H | T7 | |
| 344. | Me | CH₂CF₃ | H | H | Na | T7 | |
| 345. | Me | CH₂CF₃ | H | H | H | T8 | |
| 346. | Me | CH₂CF₃ | H | H | Na | T8 | |
| 347. | Me | CH₂CF₃ | H | H | H | T9 | |
| 348. | Me | CH₂CF₃ | H | H | Na | T9 | |
| 349. | Me | CH₂CF₃ | H | H | H | T10 | |

TABLE 1-continued

Compounds of the formula (Ia)

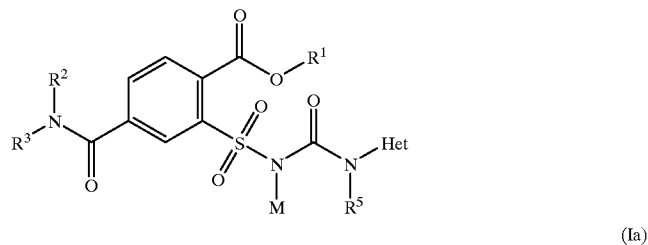

(Ia)

| Ex. | R¹ | R² | R³ | R⁵ | M | Het | m.p. |
|---|---|---|---|---|---|---|---|
| 350. | Me | CH$_2$CF$_3$ | H | H | Na | T10 | |
| 351. | Me | CH$_2$CF$_3$ | H | H | H | T11 | |
| 352. | Me | CH$_2$CF$_3$ | H | H | Na | T11 | |
| 353. | Me | CH$_2$CF$_3$ | H | H | H | T12 | |
| 354. | Me | CH$_2$CF$_3$ | H | H | Na | T12 | |
| 355. | Me | CH$_2$CF$_3$ | H | H | H | T13 | |
| 356. | Me | CH$_2$CF$_3$ | H | H | Na | T13 | |
| 357. | Me | CH$_2$CF$_3$ | H | H | H | T14 | |
| 358. | Me | CH$_2$CF$_3$ | H | H | Na | T14 | |
| 359. | Me | CH$_2$CF$_3$ | H | H | H | T15 | |
| 360. | Me | CH$_2$CF$_3$ | H | H | Na | T15 | |
| 361. | Me | Allyl | Me | H | H | T1 | 178–180(D) |
| 362. | Me | Allyl | Me | H | Na | T1 | 139–141(D) |
| 363. | Me | Allyl | Me | H | H | T2 | |
| 364. | Me | Allyl | Me | H | Na | T2 | |
| 365. | Me | Allyl | Me | H | H | T3 | |
| 366. | Me | Allyl | Me | H | Na | T3 | |
| 367. | Me | Allyl | Me | H | H | T4 | |
| 368. | Me | Allyl | Me | H | Na | T4 | |
| 369. | Me | Allyl | Me | H | H | T5 | |
| 370. | Me | Allyl | Me | H | Na | T5 | |
| 371. | Me | Allyl | Me | H | H | T6 | |
| 372. | Me | Allyl | Me | H | Na | T6 | |
| 373. | Me | Allyl | Me | H | H | T7 | |
| 374. | Me | Allyl | Me | H | Na | T7 | |
| 375. | Me | Allyl | Me | H | H | T8 | |
| 376. | Me | Allyl | Me | H | Na | T8 | |
| 377. | Me | Allyl | Me | H | H | T9 | |
| 378. | Me | Allyl | Me | H | Na | T9 | |
| 379. | Me | Allyl | Me | H | H | T10 | |
| 380. | Me | Allyl | Me | H | Na | T10 | |
| 381. | Me | Allyl | Me | H | H | T11 | |
| 382. | Me | Allyl | Me | H | Na | T11 | |
| 383. | Me | Allyl | Me | H | H | T12 | |
| 384. | Me | Allyl | Me | H | Na | T12 | |
| 385. | Me | Allyl | Me | H | H | T13 | |
| 386. | Me | Allyl | Me | H | Na | T13 | |
| 387. | Me | Allyl | Me | H | H | T14 | |
| 388. | Me | Allyl | Me | H | Na | T14 | |
| 389. | Me | Allyl | Me | H | H | T15 | |
| 390. | Me | Allyl | Me | H | Na | T15 | |
| 391. | Me | Allyl | Et | H | H | T1 | 160–162(D) |
| 392. | Me | Allyl | Et | H | Na | T1 | 145–147(D) |
| 393. | Me | Allyl | Et | H | H | T2 | |
| 394. | Me | Allyl | Et | H | Na | T2 | |
| 395. | Me | Allyl | Et | H | H | T3 | |
| 396. | Me | Allyl | Et | H | Na | T3 | |
| 397. | Me | Allyl | Et | H | H | T4 | |
| 398. | Me | Allyl | Et | H | Na | T4 | |
| 399. | Me | Allyl | Et | H | H | T5 | |
| 400. | Me | Allyl | Et | H | Na | T5 | |
| 401. | Me | Allyl | Et | H | H | T6 | |
| 402. | Me | Allyl | Et | H | Na | T6 | |
| 403. | Me | Allyl | Et | H | H | T7 | |
| 404. | Me | Allyl | Et | H | Na | T7 | |
| 405. | Me | Allyl | i-Pr | H | H | T1 | 125–127(D) |
| 406. | Me | Allyl | i-Pr | H | Na | T1 | 148–150(D) |
| 407. | Me | Allyl | i-Pr | H | H | T2 | |
| 408. | Me | Allyl | i-Pr | H | Na | T2 | |
| 409. | Me | Allyl | i-Pr | H | H | T3 | |
| 410. | Me | Allyl | i-Pr | H | Na | T3 | |
| 411. | Me | Allyl | i-Pr | H | H | T4 | |

TABLE 1-continued

Compounds of the formula (Ia)

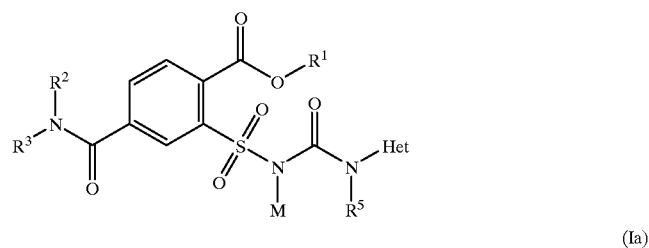

(Ia)

| Ex. | R¹ | R² | R³ | R⁵ | M | Het | m.p. |
|---|---|---|---|---|---|---|---|
| 412. | Me | Allyl | i-Pr | H | Na | T4 | |
| 413. | Me | Allyl | i-Pr | H | H | T5 | |
| 414. | Me | Allyl | i-Pr | H | Na | T5 | |
| 415. | Me | Allyl | i-Pr | H | H | T6 | |
| 416. | Me | Allyl | i-Pr | H | Na | T6 | |
| 417. | Me | Allyl | i-Pr | H | H | T7 | |
| 418. | Me | Allyl | i-Pr | H | Na | T7 | |
| 419. | Me | Allyl | i-Pr | H | H | T8 | |
| 420. | Me | Allyl | i-Pr | H | Na | T8 | |
| 421. | Me | Allyl | i-Pr | H | H | T9 | |
| 422. | Me | Allyl | i-Pr | H | Na | T9 | |
| 423. | Me | Allyl | i-Pr | H | H | T10 | |
| 424. | Me | Allyl | i-Pr | H | Na | T10 | |
| 425. | Me | Allyl | i-Pr | H | H | T11 | |
| 426. | Me | Allyl | i-Pr | H | Na | T11 | |
| 427. | Me | Allyl | i-Pr | H | H | T12 | |
| 428. | Me | Allyl | i-Pr | H | Na | T12 | |
| 429. | Me | Allyl | i-Pr | H | H | T13 | |
| 430. | Me | Allyl | i-Pr | H | Na | T13 | |
| 431. | Me | Allyl | i-Pr | H | H | T14 | |
| 432. | Me | Allyl | i-Pr | H | Na | T14 | |
| 433. | Me | Allyl | i-Pr | H | H | T15 | |
| 434. | Me | Allyl | i-Pr | H | Na | T15 | |
| 435. | Me | Allyl | Pr | H | H | T1 | 115–117(D) |
| 436. | Me | Allyl | Pr | H | Na | T1 | 150–152(D) |
| 437. | Me | Allyl | Pr | H | H | T2 | |
| 438. | Me | Allyl | Pr | H | Na | T2 | |
| 439. | Me | Allyl | Pr | H | H | T3 | |
| 440. | Me | Allyl | Pr | H | Na | T3 | |
| 441. | Me | Allyl | Pr | H | H | T4 | |
| 442. | Me | Allyl | Pr | H | Na | T4 | |
| 443. | Me | Allyl | Pr | H | H | T5 | |
| 444. | Me | Allyl | Pr | H | Na | T5 | |
| 445. | Me | Allyl | Pr | H | H | T6 | |
| 446. | Me | Allyl | Pr | H | Na | T6 | |
| 447. | Me | Allyl | Pr | H | H | T7 | |
| 448. | Me | Allyl | Pr | H | Na | T7 | |
| 449. | Me | Allyl | Allyl | H | H | T1 | 166–168(D) |
| 450. | Me | Allyl | Allyl | H | Na | T1 | 147–149(D) |
| 451. | Me | Allyl | Allyl | H | H | T2 | |
| 452. | Me | Allyl | Allyl | H | Na | T2 | |
| 453. | Me | Allyl | Allyl | H | H | T3 | |
| 454. | Me | Allyl | Allyl | H | Na | T3 | |
| 455. | Me | Allyl | Allyl | H | H | T4 | |
| 456. | Me | Allyl | Allyl | H | Na | T4 | |
| 457. | Me | Allyl | Allyl | H | H | T5 | |
| 458. | Me | Allyl | Allyl | H | Na | T5 | |
| 459. | Me | Allyl | Allyl | H | H | T6 | |
| 460. | Me | Allyl | Allyl | H | Na | T6 | |
| 461. | Me | Allyl | Allyl | H | H | T7 | |
| 462. | Me | Allyl | Allyl | H | Na | T7 | |
| 463. | Me | Allyl | Allyl | H | H | T8 | |
| 464. | Me | Allyl | Allyl | H | Na | T8 | |
| 465. | Me | Allyl | Allyl | H | H | T9 | |
| 466. | Me | Allyl | Allyl | H | Na | T9 | |
| 467. | Me | Allyl | Allyl | H | H | T10 | |
| 468. | Me | Allyl | Allyl | H | Na | T10 | |
| 469. | Me | Allyl | Allyl | H | H | T11 | |
| 470. | Me | Allyl | Allyl | H | Na | T11 | |
| 471. | Me | Allyl | Allyl | H | H | T12 | |
| 472. | Me | Allyl | Allyl | H | Na | T12 | |
| 473. | Me | Allyl | Allyl | H | H | T13 | |

TABLE 1-continued

Compounds of the formula (Ia)

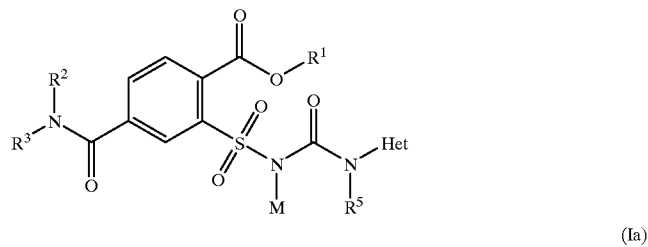

(Ia)

| Ex. | R¹ | R² | R³ | R⁵ | M | Het | m.p. |
|---|---|---|---|---|---|---|---|
| 474. | Me | Allyl | Allyl | H | Na | T13 | |
| 475. | Me | Allyl | Allyl | H | H | T14 | |
| 476. | Me | Allyl | Allyl | H | Na | T14 | |
| 477. | Me | Allyl | Allyl | H | H | T15 | |
| 478. | Me | Allyl | Allyl | H | Na | T15 | |
| 479. | Et | H | H | H | H | T1 | 129–132(D) |
| 480. | Et | H | H | H | Na | T1 | 226–232(D) |
| 481. | Et | H | H | H | H | T2 | |
| 482. | Et | H | H | H | Na | T2 | |
| 483. | Et | H | H | H | H | T5 | |
| 484. | Et | H | H | H | Na | T5 | |
| 485. | Et | H | H | H | H | T6 | |
| 486. | Et | H | H | H | Na | T6 | |
| 487. | Et | H | H | H | H | T7 | |
| 488. | Et | H | H | H | Na | T7 | |
| 489. | Pr | H | H | H | H | T1 | |
| 490. | Pr | H | H | H | Na | T1 | |
| 491. | Pr | H | H | H | H | T2 | |
| 492. | Pr | H | H | H | Na | T2 | |
| 493. | Pr | H | H | H | H | T5 | |
| 494. | Pr | H | H | H | Na | T5 | |
| 495. | Pr | H | H | H | H | T6 | |
| 496. | Pr | H | H | H | Na | T6 | |
| 497. | Pr | H | H | H | H | T7 | |
| 498. | Pr | H | H | H | Na | T7 | |
| 499. | i-Pr | H | H | H | H | T1 | 158–161(D) |
| 500. | i-Pr | H | H | H | Na | T1 | 239–242(D) |
| 501. | i-Pr | H | H | H | H | T2 | |
| 502. | i-Pr | H | H | H | Na | T2 | |
| 503. | i-Pr | H | H | H | H | T5 | |
| 504. | i-Pr | H | H | H | Na | T5 | |
| 505. | i-Pr | H | H | H | H | T6 | |
| 506. | i-Pr | H | H | H | Na | T6 | |
| 507. | i-Pr | H | H | H | H | T7 | |
| 508. | i-Pr | H | H | H | Na | T7 | |
| 509. | c-Pr | H | H | H | H | T1 | |
| 510. | c-Pr | H | H | H | Na | T1 | |
| 511. | c-Pr | H | H | H | H | T2 | |
| 512. | c-Pr | H | H | H | Na | T2 | |
| 513. | c-Pr | H | H | H | H | T5 | |
| 514. | c-Pr | H | H | H | Na | T5 | |
| 515. | c-Pr | H | H | H | H | T6 | |
| 516. | c-Pr | H | H | H | Na | T6 | |
| 517. | c-Pr | H | H | H | H | T7 | |
| 518. | c-Pr | H | H | H | Na | T7 | |
| 519. | Bu | H | H | H | H | T1 | |
| 520. | Bu | H | H | H | Na | T1 | |
| 521. | Bu | H | H | H | H | T2 | |
| 522. | Bu | H | H | H | Na | T2 | |
| 523. | Bu | H | H | H | H | T5 | |
| 524. | Bu | H | H | H | Na | T5 | |
| 525. | Bu | H | H | H | H | T6 | |
| 526. | Bu | H | H | H | Na | T6 | |
| 527. | Bu | H | H | H | H | T7 | |
| 528. | Bu | H | H | H | Na | T7 | |
| 529. | CH₂-c-Pr | H | H | H | H | T1 | 131–133 |
| 530. | CH₂-c-Pr | H | H | H | Na | T1 | |
| 531. | CH₂-c-Pr | H | H | H | H | T2 | |
| 532. | CH₂-c-Pr | H | H | H | Na | T2 | |
| 533. | CH₂-c-Pr | H | H | H | H | T5 | |
| 534. | CH₂-c-Pr | H | H | H | Na | T5 | |
| 535. | CH₂-c-Pr | H | H | H | H | T6 | |

TABLE 1-continued

Compounds of the formula (Ia)

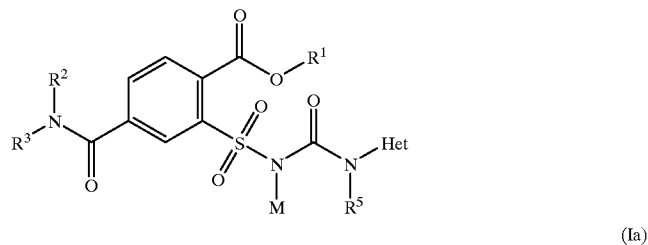

(Ia)

| Ex. | R¹ | R² | R³ | R⁵ | M | Het | m.p. |
|---|---|---|---|---|---|---|---|
| 536. | CH₂-c-Pr | H | H | H | Na | T6 | |
| 537. | CH₂-c-Pr | H | H | H | H | T7 | |
| 538. | CH₂-c-Pr | H | H | H | Na | T7 | |
| 539. | CH₂CH₂F | H | H | H | H | T1 | 130–133 |
| 540. | CH₂CH₂F | H | H | H | Na | T1 | |
| 541. | CH₂CH₂F | H | H | H | H | T2 | |
| 542. | CH₂CH₂F | H | H | H | Na | T2 | |
| 543. | CH₂CH₂F | H | H | H | H | T5 | |
| 544. | CH₂CH₂F | H | H | H | Na | T5 | |
| 545. | CH₂CH₂F | H | H | H | H | T6 | |
| 546. | CH₂CH₂F | H | H | H | Na | T6 | |
| 547. | CH₂CH₂F | H | H | H | H | T7 | |
| 548. | CH₂CH₂F | H | H | H | Na | T7 | |
| 549. | CH₂CH₂CF₃ | H | H | H | H | T1 | |
| 550. | CH₂CH₂CF₃ | H | H | H | Na | T1 | |
| 551. | CH₂CH₂CF₃ | H | H | H | H | T2 | |
| 552. | CH₂CH₂CF₃ | H | H | H | Na | T2 | |
| 553. | CH₂CH₂CF₃ | H | H | H | H | T5 | |
| 554. | CH₂CH₂CF₃ | H | H | H | Na | T5 | |
| 555. | CH₂CH₂CF₃ | H | H | H | H | T6 | |
| 556. | CH₂CH₂CF₃ | H | H | H | Na | T6 | |
| 557. | CH₂CH₂CF₃ | H | H | H | H | T7 | |
| 558. | CH₂CH₂CF₃ | H | H | H | Na | T7 | |
| 559. | 3-Oxetanyl | H | H | H | H | T1 | |
| 560. | 3-Oxetanyl | H | H | H | Na | T1 | |
| 561. | 3-Oxetanyl | H | H | H | H | T2 | |
| 562. | 3-Oxetanyl | H | H | H | Na | T2 | |
| 563. | 3-Oxetanyl | H | H | H | H | T5 | |
| 564. | 3-Oxetanyl | H | H | H | Na | T5 | |
| 565. | 3-Oxetanyl | H | H | H | H | T6 | |
| 566. | 3-Oxetanyl | H | H | H | Na | T6 | |
| 567. | 3-Oxetanyl | H | H | H | H | T7 | |
| 568. | 3-Oxetanyl | H | H | H | Na | T7 | |
| 569. | Et | Me | H | H | H | T1 | |
| 570. | Et | Me | H | H | Na | T1 | |
| 571. | Et | Me | H | H | H | T2 | |
| 572. | Et | Me | H | H | Na | T2 | |
| 573. | Et | Me | H | H | H | T5 | |
| 574. | Et | Me | H | H | Na | T5 | |
| 575. | Et | Me | H | H | H | T6 | |
| 576. | Et | Me | H | H | Na | T6 | |
| 577. | Et | Me | H | H | H | T7 | |
| 578. | Et | Me | H | H | Na | T7 | |
| 579. | Pr | Me | H | H | H | T1 | |
| 580. | Pr | Me | H | H | Na | T1 | |
| 581. | Pr | Me | H | H | H | T2 | |
| 582. | Pr | Me | H | H | Na | T2 | |
| 583. | Pr | Me | H | H | H | T5 | |
| 584. | Pr | Me | H | H | Na | T5 | |
| 585. | Pr | Me | H | H | H | T6 | |
| 586. | Pr | Me | H | H | Na | T6 | |
| 587. | Pr | Me | H | H | H | T7 | |
| 588. | Pr | Me | H | H | Na | T7 | |
| 589. | i-Pr | Me | H | H | H | T1 | |
| 590. | i-Pr | Me | H | H | Na | T1 | |
| 591. | i-Pr | Me | H | H | H | T2 | |
| 592. | i-Pr | Me | H | H | Na | T2 | |
| 593. | i-Pr | Me | H | H | H | T5 | |
| 594. | i-Pr | Me | H | H | Na | T5 | |
| 595. | i-Pr | Me | H | H | H | T6 | |
| 596. | i-Pr | Me | H | H | Na | T6 | |
| 597. | i-Pr | Me | H | H | H | T7 | |

TABLE 1-continued

Compounds of the formula (Ia)

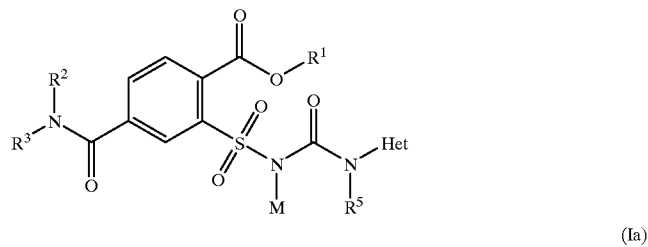

| Ex. | R¹ | R² | R³ | R⁵ | M | Het | m.p. |
|---|---|---|---|---|---|---|---|
| 598. | i-Pr | Me | H | H | Na | T7 | |
| 599. | c-Pr | Me | H | H | H | T1 | |
| 600. | c-Pr | Me | H | H | Na | T1 | |
| 601. | c-Pr | Me | H | H | H | T2 | |
| 602. | c-Pr | Me | H | H | Na | T2 | |
| 603. | c-Pr | Me | H | H | H | T5 | |
| 604. | c-Pr | Me | H | H | Na | T5 | |
| 605. | c-Pr | Me | H | H | H | T6 | |
| 606. | c-Pr | Me | H | H | Na | T6 | |
| 607. | c-Pr | Me | H | H | H | T7 | |
| 608. | c-Pr | Me | H | H | Na | T7 | |
| 609. | Bu | Me | H | H | H | T1 | |
| 610. | Bu | Me | H | H | Na | T1 | |
| 611. | Bu | Me | H | H | H | T2 | |
| 612. | Bu | Me | H | H | Na | T2 | |
| 613. | Bu | Me | H | H | H | T5 | |
| 614. | Bu | Me | H | H | Na | T5 | |
| 615. | Bu | Me | H | H | H | T6 | |
| 616. | Bu | Me | H | H | Na | T6 | |
| 617. | Bu | Me | H | H | H | T7 | |
| 618. | Bu | Me | H | H | Na | T7 | |
| 619. | CH₂-c-Pr | Me | H | H | H | T1 | |
| 620. | CH₂-c-Pr | Me | H | H | Na | T1 | |
| 621. | CH₂-c-Pr | Me | H | H | H | T2 | |
| 622. | CH₂-c-Pr | Me | H | H | Na | T2 | |
| 623. | CH₂-c-Pr | Me | H | H | H | T5 | |
| 624. | CH₂-c-Pr | Me | H | H | Na | T5 | |
| 625. | CH₂-c-Pr | Me | H | H | H | T6 | |
| 626. | CH₂-c-Pr | Me | H | H | Na | T6 | |
| 627. | CH₂-c-Pr | Me | H | H | H | T7 | |
| 628. | CH₂-c-Pr | Me | H | H | Na | T7 | |
| 629. | CH₂CH₂F | Me | H | H | H | T1 | |
| 630. | CH₂CH₂F | Me | H | H | Na | T1 | |
| 631. | CH₂CH₂F | Me | H | H | H | T2 | |
| 632. | CH₂CH₂F | Me | H | H | Na | T2 | |
| 633. | CH₂CH₂F | Me | H | H | H | T5 | |
| 634. | CH₂CH₂F | Me | H | H | Na | T5 | |
| 635. | CH₂CH₂F | Me | H | H | H | T6 | |
| 636. | CH₂CH₂F | Me | H | H | Na | T6 | |
| 637. | CH₂CH₂F | Me | H | H | H | T7 | |
| 638. | CH₂CH₂F | Me | H | H | Na | T7 | |
| 639. | CH₂CH₂CF₃ | Me | H | H | H | T1 | |
| 640. | CH₂CH₂CF₃ | Me | H | H | Na | T1 | |
| 641. | CH₂CH₂CF₃ | Me | H | H | H | T2 | |
| 642. | CH₂CH₂CF₃ | Me | H | H | Na | T2 | |
| 643. | CH₂CH₂CF₃ | Me | H | H | H | T5 | |
| 644. | CH₂CH₂CF₃ | Me | H | H | Na | T5 | |
| 645. | CH₂CH₂CF₃ | Me | H | H | H | T6 | |
| 646. | CH₂CH₂CF₃ | Me | H | H | Na | T6 | |
| 647. | CH₂CH₂CF₃ | Me | H | H | H | T7 | |
| 648. | CH₂CH₂CF₃ | Me | H | H | Na | T7 | |
| 649. | 3-Oxetanyl | Me | H | H | H | T1 | |
| 650. | 3-Oxetanyl | Me | H | H | Na | T1 | |
| 651. | 3-Oxetanyl | Me | H | H | H | T2 | |
| 652. | 3-Oxetanyl | Me | H | H | Na | T2 | |
| 653. | 3-Oxetanyl | Me | H | H | H | T5 | |
| 654. | 3-Oxetanyl | Me | H | H | Na | T5 | |
| 655. | 3-Oxetanyl | Me | H | H | H | T6 | |
| 656. | 3-Oxetanyl | Me | H | H | Na | T6 | |
| 657. | 3-Oxetanyl | Me | H | H | H | T7 | |
| 658. | 3-Oxetanyl | Me | H | H | Na | T7 | |
| 659. | Et | Et | H | H | H | T1 | |

TABLE 1-continued

Compounds of the formula (Ia)

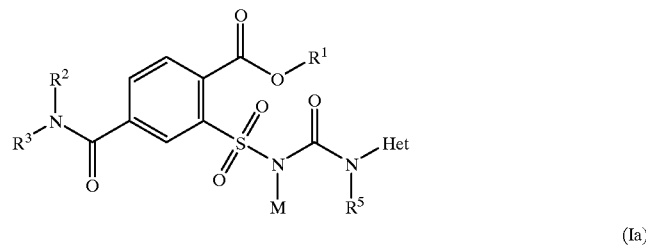

(Ia)

| Ex. | R¹ | R² | R³ | R⁵ | M | Het | m.p. |
|---|---|---|---|---|---|---|---|
| 660. | Et | Et | H | H | Na | T1 | |
| 661. | Et | Et | H | H | H | T2 | |
| 662. | Et | Et | H | H | Na | T2 | |
| 663. | Et | Et | H | H | H | T5 | |
| 664. | Et | Et | H | H | Na | T5 | |
| 665. | Et | Et | H | H | H | T6 | |
| 666. | Et | Et | H | H | Na | T6 | |
| 667. | Et | Et | H | H | H | T7 | |
| 668. | Et | Et | H | H | Na | T7 | |
| 669. | Pr | Et | H | H | H | T1 | |
| 670. | Pr | Et | H | H | Na | T1 | |
| 671. | Pr | Et | H | H | H | T2 | |
| 672. | Pr | Et | H | H | Na | T2 | |
| 673. | Pr | Et | H | H | H | T5 | |
| 674. | Pr | Et | H | H | Na | T5 | |
| 675. | Pr | Et | H | H | H | T6 | |
| 676. | Pr | Et | H | H | Na | T6 | |
| 677. | Pr | Et | H | H | H | T7 | |
| 678. | Pr | Et | H | H | Na | T7 | |
| 679. | i-Pr | Et | H | H | H | T1 | |
| 680. | i-Pr | Et | H | H | Na | T1 | |
| 681. | i-Pr | Et | H | H | H | T2 | |
| 682. | i-Pr | Et | H | H | Na | T2 | |
| 683. | i-Pr | Et | H | H | H | T5 | |
| 684. | i-Pr | Et | H | H | Na | T5 | |
| 685. | i-Pr | Et | H | H | H | T6 | |
| 686. | i-Pr | Et | H | H | Na | T6 | |
| 687. | i-Pr | Et | H | H | H | T7 | |
| 688. | i-Pr | Et | H | H | Na | T7 | |
| 699. | c-Pr | Et | H | H | H | T1 | |
| 690. | c-Pr | Et | H | H | Na | T1 | |
| 691. | c-Pr | Et | H | H | H | T2 | |
| 692. | c-Pr | Et | H | H | Na | T2 | |
| 693. | c-Pr | Et | H | H | H | T5 | |
| 694. | c-Pr | Et | H | H | Na | T5 | |
| 695. | c-Pr | Et | H | H | H | T6 | |
| 696. | c-Pr | Et | H | H | Na | T6 | |
| 697. | c-Pr | Et | H | H | H | T7 | |
| 698. | c-Pr | Et | H | H | Na | T7 | |
| 699. | Bu | Et | H | H | H | T1 | |
| 700. | Bu | Et | H | H | Na | T1 | |
| 701. | Bu | Et | H | H | H | T2 | |
| 702. | Bu | Et | H | H | Na | T2 | |
| 703. | Bu | Et | H | H | H | T5 | |
| 704. | Bu | Et | H | H | Na | T5 | |
| 705. | Bu | Et | H | H | H | T6 | |
| 706. | Bu | Et | H | H | Na | T6 | |
| 707. | Bu | Et | H | H | H | T7 | |
| 708. | Bu | Et | H | H | Na | T7 | |
| 709. | $CH_2$-c-Pr | Et | H | H | H | T1 | |
| 710. | $CH_2$-c-Pr | Et | H | H | Na | T1 | |
| 711. | $CH_2$-c-Pr | Et | H | H | H | T2 | |
| 712. | $CH_2$-c-Pr | Et | H | H | Na | T2 | |
| 713. | $CH_2$-c-Pr | Et | H | H | H | T5 | |
| 714. | $CH_2$-c-Pr | Et | H | H | Na | T5 | |
| 715. | $CH_2$-c-Pr | Et | H | H | H | T6 | |
| 716. | $CH_2$-c-Pr | Et | H | H | Na | T6 | |
| 717. | $CH_2$-c-Pr | Et | H | H | H | T7 | |
| 718. | $CH_2$-c-Pr | Et | H | H | Na | T7 | |
| 719. | $CH_2CH_2F$ | Et | H | H | H | T1 | |
| 720. | $CH_2CH_2F$ | Et | H | H | Na | T1 | |
| 721. | $CH_2CH_2F$ | Et | H | H | H | T2 | |

TABLE 1-continued

Compounds of the formula (Ia)

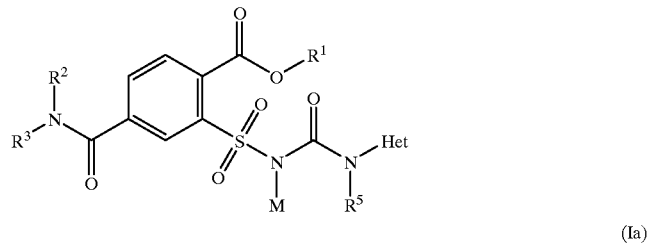

(Ia)

| Ex. | R$^1$ | R$^2$ | R$^3$ | R$^5$ | M | Het | m.p. |
|---|---|---|---|---|---|---|---|
| 722. | CH$_2$CH$_2$F | Et | H | H | Na | T2 | |
| 723. | CH$_2$CH$_2$F | Et | H | H | H | T5 | |
| 724. | CH$_2$CH$_2$F | Et | H | H | Na | T5 | |
| 725. | CH$_2$CH$_2$F | Et | H | H | H | T6 | |
| 726. | CH$_2$CH$_2$F | Et | H | H | Na | T6 | |
| 727. | CH$_2$CH$_2$F | Et | H | H | H | T7 | |
| 728. | CH$_2$CH$_2$F | Et | H | H | Na | T7 | |
| 729. | CH$_2$CH$_2$CF$_3$ | Et | H | H | H | T1 | |
| 730. | CH$_2$CH$_2$CF$_3$ | Et | H | H | Na | T1 | |
| 731. | CH$_2$CH$_2$CF$_3$ | Et | H | H | H | T2 | |
| 732. | CH$_2$CH$_2$CF$_3$ | Et | H | H | Na | T2 | |
| 733. | CH$_2$CH$_2$CF$_3$ | Et | H | H | H | T5 | |
| 734. | CH$_2$CH$_2$CF$_3$ | Et | H | H | Na | T5 | |
| 735. | CH$_2$CH$_2$CF$_3$ | Et | H | H | H | T6 | |
| 736. | CH$_2$CH$_2$CF$_3$ | Et | H | H | Na | T6 | |
| 737. | CH$_2$CH$_2$CF$_3$ | Et | H | H | H | T7 | |
| 738. | CH$_2$CH$_2$CF$_3$ | Et | H | H | Na | T7 | |
| 739. | 3-Oxetanyl | Et | H | H | H | T1 | |
| 740. | 3-Oxetanyl | Et | H | H | Na | T1 | |
| 741. | 3-Oxetanyl | Et | H | H | H | T2 | |
| 742. | 3-Oxetanyl | Et | H | H | Na | T2 | |
| 743. | 3-Oxetanyl | Et | H | H | H | T5 | |
| 744. | 3-Oxetanyl | Et | H | H | Na | T5 | |
| 745. | 3-Oxetanyl | Et | H | H | H | T6 | |
| 746. | 3-Oxetanyl | Et | H | H | Na | T6 | |
| 747. | 3-Oxetanyl | Et | H | H | H | T7 | |
| 748. | 3-Oxetanyl | Et | H | H | Na | T7 | |
| 749. | Et | i-Pr | H | H | H | T1 | 121–123(D) |
| 750. | Et | i-Pr | H | H | Na | T1 | |
| 751. | Et | i-Pr | H | H | H | T2 | |
| 752. | Et | i-Pr | H | H | Na | T2 | |
| 753. | Et | i-Pr | H | H | H | T5 | |
| 754. | Et | i-Pr | H | H | Na | T5 | |
| 755. | Et | i-Pr | H | H | H | T6 | |
| 756. | Et | i-Pr | H | H | Na | T6 | |
| 757. | Et | i-Pr | H | H | H | T7 | |
| 758. | Et | i-Pr | H | H | Na | T7 | |
| 759. | Pr | i-Pr | H | H | H | T1 | |
| 760. | Pr | i-Pr | H | H | Na | T1 | |
| 761. | Pr | i-Pr | H | H | H | T2 | |
| 762. | Pr | i-Pr | H | H | Na | T2 | |
| 763. | Pr | i-Pr | H | H | H | T5 | |
| 764. | Pr | i-Pr | H | H | Na | T5 | |
| 765. | Pr | i-Pr | H | H | H | T6 | |
| 766. | Pr | i-Pr | H | H | Na | T6 | |
| 767. | Pr | i-Pr | H | H | H | T7 | |
| 768. | Pr | i-Pr | H | H | Na | T7 | |
| 769. | i-Pr | i-Pr | H | H | H | T1 | 157–162(D) |
| 770. | i-Pr | i-Pr | H | H | Na | T1 | 209–213(D) |
| 771. | i-Pr | i-Pr | H | H | H | T2 | |
| 772. | i-Pr | i-Pr | H | H | Na | T2 | |
| 773. | i-Pr | i-Pr | H | H | H | T5 | |
| 774. | i-Pr | i-Pr | H | H | Na | T5 | |
| 775. | i-Pr | i-Pr | H | H | H | T6 | |
| 776. | i-Pr | i-Pr | H | H | Na | T6 | |
| 777. | i-Pr | i-Pr | H | H | H | T7 | |
| 778. | i-Pr | i-Pr | H | H | Na | T7 | |
| 779. | c-Pr | i-Pr | H | H | H | T1 | |
| 780. | c-Pr | i-Pr | H | H | Na | T1 | |
| 781. | c-Pr | i-Pr | H | H | H | T2 | |
| 782. | c-Pr | i-Pr | H | H | Na | T2 | |
| 783. | c-Pr | i-Pr | H | H | H | T5 | |

TABLE 1-continued

Compounds of the formula (Ia)

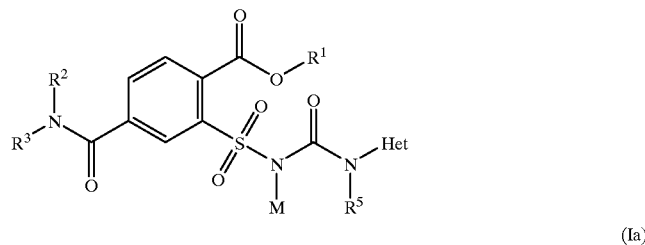

(Ia)

| Ex. | R$^1$ | R$^2$ | R$^3$ | R$^5$ | M | Het | m.p. |
|---|---|---|---|---|---|---|---|
| 784. | c-Pr | i-Pr | H | H | Na | T5 | |
| 785. | c-Pr | i-Pr | H | H | H | T6 | |
| 786. | c-Pr | i-Pr | H | H | Na | T6 | |
| 787. | c-Pr | i-Pr | H | H | H | T7 | |
| 788. | c-Pr | i-Pr | H | H | Na | T7 | |
| 789. | Bu | i-Pr | H | H | H | T1 | |
| 790. | Bu | i-Pr | H | H | Na | T1 | |
| 791. | Bu | i-Pr | H | H | H | T2 | |
| 792. | Bu | i-Pr | H | H | Na | T2 | |
| 793. | Bu | i-Pr | H | H | H | T5 | |
| 794. | Bu | i-Pr | H | H | Na | T5 | |
| 795. | Bu | i-Pr | H | H | H | T6 | |
| 796. | Bu | i-Pr | H | H | Na | T6 | |
| 797. | Bu | i-Pr | H | H | H | T7 | |
| 798. | Bu | i-Pr | H | H | Na | T7 | |
| 799. | CH$_2$-c-Pr | i-Pr | H | H | H | T1 | |
| 800. | CH$_2$-c-Pr | i-Pr | H | H | Na | T1 | |
| 801. | CH$_2$-c-Pr | i-Pr | H | H | H | T2 | |
| 802. | CH$_2$-c-Pr | i-Pr | H | H | Na | T2 | |
| 803. | CH$_2$-c-Pr | i-Pr | H | H | H | T5 | |
| 804. | CH$_2$-c-Pr | i-Pr | H | H | Na | T5 | |
| 805. | CH$_2$-c-Pr | i-Pr | H | H | H | T6 | |
| 806. | CH$_2$-c-Pr | i-Pr | H | H | Na | T6 | |
| 807. | CH$_2$-c-Pr | i-Pr | H | H | H | T7 | |
| 808. | CH$_2$-c-Pr | i-Pr | H | H | Na | T7 | |
| 809. | CH$_2$CH$_2$F | i-Pr | H | H | H | T1 | |
| 810. | CH$_2$CH$_2$F | i-Pr | H | H | Na | T1 | |
| 811. | CH$_2$CH$_2$F | i-Pr | H | H | H | T2 | |
| 812. | CH$_2$CH$_2$F | i-Pr | H | H | Na | T2 | |
| 813. | CH$_2$CH$_2$F | i-Pr | H | H | H | T5 | |
| 814. | CH$_2$CH$_2$F | i-Pr | H | H | Na | T5 | |
| 815. | CH$_2$CH$_2$F | i-Pr | H | H | H | T6 | |
| 816. | CH$_2$CH$_2$F | i-Pr | H | H | Na | T6 | |
| 817. | CH$_2$CH$_2$F | i-Pr | H | H | H | T7 | |
| 818. | CH$_2$CH$_2$F | i-Pr | H | H | Na | T7 | |
| 819. | CH$_2$CH$_2$CF$_3$ | i-Pr | H | H | H | T1 | |
| 820. | CH$_2$CH$_2$CF$_3$ | i-Pr | H | H | Na | T1 | |
| 821. | CH$_2$CH$_2$CF$_3$ | i-Pr | H | H | H | T2 | |
| 822. | CH$_2$CH$_2$CF$_3$ | i-Pr | H | H | Na | T2 | |
| 823. | CH$_2$CH$_2$CF$_3$ | i-Pr | H | H | H | T5 | |
| 824. | CH$_2$CH$_2$CF$_3$ | i-Pr | H | H | Na | T5 | |
| 825. | CH$_2$CH$_2$CF$_3$ | i-Pr | H | H | H | T6 | |
| 826. | CH$_2$CH$_2$CF$_3$ | i-Pr | H | H | Na | T6 | |
| 827. | CH$_2$CH$_2$CF$_3$ | i-Pr | H | H | H | T7 | |
| 828. | CH$_2$CH$_2$CF$_3$ | i-Pr | H | H | Na | T7 | |
| 829. | 3-Oxetanyl | i-Pr | H | H | H | T1 | |
| 830. | 3-Oxetanyl | i-Pr | H | H | Na | T1 | |
| 831. | 3-Oxetanyl | i-Pr | H | H | H | T2 | |
| 832. | 3-Oxetanyl | i-Pr | H | H | Na | T2 | |
| 833. | 3-Oxetanyl | i-Pr | H | H | H | T5 | |
| 834. | 3-Oxetanyl | i-Pr | H | H | Na | T5 | |
| 835. | 3-Oxetanyl | i-Pr | H | H | H | T6 | |
| 836. | 3-Oxetanyl | i-Pr | H | H | Na | T6 | |
| 837. | 3-Oxetanyl | i-Pr | H | H | H | T7 | |
| 838. | 3-Oxetanyl | i-Pr | H | H | Na | T7 | |
| 839. | Et | Me | Me | H | H | T1 | 180–182 |
| 840. | Et | Me | Me | H | Na | T1 | 218–221 |
| 841. | Et | Me | Me | H | H | T2 | |
| 842. | Et | Me | Me | H | Na | T2 | |
| 843. | Et | Me | Me | H | H | T5 | |
| 844. | Et | Me | Me | H | Na | T5 | |
| 845. | Et | Me | Me | H | H | T6 | |

TABLE 1-continued

Compounds of the formula (Ia)

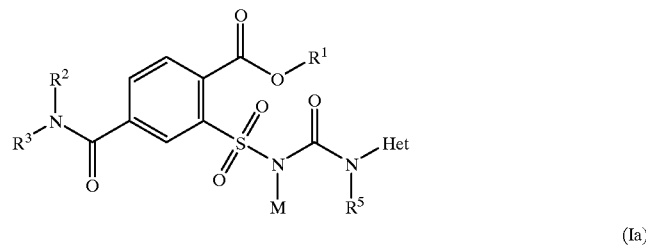

(Ia)

| Ex. | R¹ | R² | R³ | R⁵ | M | Het | m.p. |
|---|---|---|---|---|---|---|---|
| 846. | Et | Me | Me | H | Na | T6 | |
| 847. | Et | Me | Me | H | H | T7 | |
| 848. | Et | Me | Me | H | Na | T7 | |
| 849. | Pr | Me | Me | H | H | T1 | |
| 850. | Pr | Me | Me | H | Na | T1 | |
| 851. | Pr | Me | Me | H | H | T2 | |
| 852. | Pr | Me | Me | H | Na | T2 | |
| 853. | Pr | Me | Me | H | H | T5 | |
| 854. | Pr | Me | Me | H | Na | T5 | |
| 855. | Pr | Me | Me | H | H | T6 | |
| 856. | Pr | Me | Me | H | Na | T6 | |
| 857. | Pr | Me | Me | H | H | T7 | |
| 858. | Pr | Me | Me | H | Na | T7 | |
| 859. | i-Pr | Me | Me | H | H | T1 | 192–196(D) |
| 860. | i-Pr | Me | Me | H | Na | T1 | 202–207(D) |
| 861. | i-Pr | Me | Me | H | H | T2 | |
| 862. | i-Pr | Me | Me | H | Na | T2 | |
| 863. | i-Pr | Me | Me | H | H | T5 | |
| 864. | i-Pr | Me | Me | H | Na | T5 | |
| 865. | i-Pr | Me | Me | H | H | T6 | |
| 866. | i-Pr | Me | Me | H | Na | T6 | |
| 867. | i-Pr | Me | Me | H | H | T7 | |
| 868. | i-Pr | Me | Me | H | Na | T7 | |
| 869. | c-Pr | Me | Me | H | H | T1 | |
| 860. | c-Pr | Me | Me | H | Na | T1 | |
| 871. | c-Pr | Me | Me | H | H | T2 | |
| 872. | c-Pr | Me | Me | H | Na | T2 | |
| 873. | c-Pr | Me | Me | H | H | T5 | |
| 874. | c-Pr | Me | Me | H | Na | T5 | |
| 875. | c-Pr | Me | Me | H | H | T6 | |
| 876. | c-Pr | Me | Me | H | Na | T6 | |
| 877. | c-Pr | Me | Me | H | H | T7 | |
| 878. | c-Pr | Me | Me | H | Na | T7 | |
| 879. | Bu | Me | Me | H | H | T1 | |
| 880. | Bu | Me | Me | H | Na | T1 | |
| 881. | Bu | Me | Me | H | H | T2 | |
| 882. | Bu | Me | Me | H | Na | T2 | |
| 883. | Bu | Me | Me | H | H | T5 | |
| 884. | Bu | Me | Me | H | Na | T5 | |
| 885. | Bu | Me | Me | H | H | T6 | |
| 886. | Bu | Me | Me | H | Na | T6 | |
| 887. | Bu | Me | Me | H | H | T7 | |
| 888. | Bu | Me | Me | H | Na | T7 | |
| 889. | CH₂-c-Pr | Me | Me | H | H | T1 | 205–207 |
| 890. | CH₂-c-Pr | Me | Me | H | Na | T1 | 218–219 |
| 891. | CH₂-c-Pr | Me | Me | H | H | T2 | |
| 892. | CH₂-c-Pr | Me | Me | H | Na | T2 | |
| 893. | CH₂-c-Pr | Me | Me | H | H | T5 | |
| 894. | CH₂-c-Pr | Me | Me | H | Na | T5 | |
| 895. | CH₂-c-Pr | Me | Me | H | H | T6 | |
| 896. | CH₂-c-Pr | Me | Me | H | Na | T6 | |
| 897. | CH₂-c-Pr | Me | Me | H | H | T7 | |
| 898. | CH₂-c-Pr | Me | Me | H | Na | T7 | |
| 899. | CH₂CH₂F | Me | Me | H | H | T1 | |
| 900. | CH₂CH₂F | Me | Me | H | Na | T1 | |
| 901. | CH₂CH₂F | Me | Me | H | H | T2 | |
| 902. | CH₂CH₂F | Me | Me | H | Na | T2 | |
| 903. | CH₂CH₂F | Me | Me | H | H | T5 | |
| 904. | CH₂CH₂F | Me | Me | H | Na | T5 | |
| 905. | CH₂CH₂F | Me | Me | H | H | T6 | |
| 906. | CH₂CH₂F | Me | Me | H | Na | T6 | |
| 907. | CH₂CH₂F | Me | Me | H | H | T7 | |

TABLE 1-continued

Compounds of the formula (Ia)

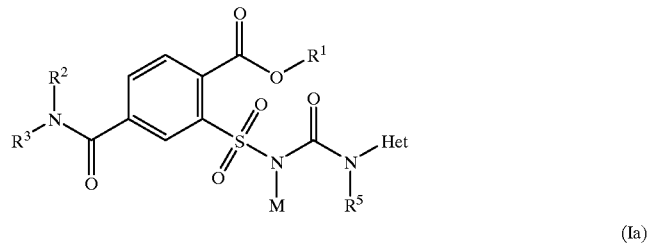

(Ia)

| Ex. | R¹ | R² | R³ | R⁵ | M | Het | m.p. |
|---|---|---|---|---|---|---|---|
| 908. | CH₂CH₂F | Me | Me | H | Na | T7 | |
| 909. | CH₂CH₂CF₃ | Me | Me | H | H | T1 | |
| 910. | CH₂CH₂CF₃ | Me | Me | H | Na | T1 | |
| 911. | CH₂CH₂CF₃ | Me | Me | H | H | T2 | |
| 912. | CH₂CH₂CF₃ | Me | Me | H | Na | T2 | |
| 913. | CH₂CH₂CF₃ | Me | Me | H | H | T5 | |
| 914. | CH₂CH₂CF₃ | Me | Me | H | Na | T5 | |
| 915. | CH₂CH₂CF₃ | Me | Me | H | H | T6 | |
| 916. | CH₂CH₂CF₃ | Me | Me | H | Na | T6 | |
| 917. | CH₂CH₂CF₃ | Me | Me | H | H | T7 | |
| 918. | CH₂CH₂CF₃ | Me | Me | H | Na | T7 | |
| 919. | 3-Oxetanyl | Me | Me | H | H | T1 | |
| 920. | 3-Oxetanyl | Me | Me | H | Na | T1 | |
| 921. | 3-Oxetanyl | Me | Me | H | H | T2 | |
| 922. | 3-Oxetanyl | Me | Me | H | Na | T2 | |
| 923. | 3-Oxetanyl | Me | Me | H | H | T5 | |
| 924. | 3-Oxetanyl | Me | Me | H | Na | T5 | |
| 925. | 3-Oxetanyl | Me | Me | H | H | T6 | |
| 926. | 3-Oxetanyl | Me | Me | H | Na | T6 | |
| 927. | 3-Oxetanyl | Me | Me | H | H | T7 | |
| 928. | 3-Oxetanyl | Me | Me | H | Na | T7 | |
| 929. | Et | Allyl | H | H | H | T1 | |
| 930. | Et | Allyl | H | H | Na | T1 | |
| 931. | Et | Allyl | H | H | H | T2 | |
| 932. | Et | Allyl | H | H | Na | T2 | |
| 933. | Et | Allyl | H | H | H | T5 | |
| 934. | Et | Allyl | H | H | Na | T5 | |
| 935. | Et | Allyl | H | H | H | T6 | |
| 936. | Et | Allyl | H | H | Na | T6 | |
| 937. | Et | Allyl | H | H | H | T7 | |
| 938. | Et | Allyl | H | H | Na | T7 | |
| 939. | Pr | Allyl | H | H | H | T1 | |
| 940. | Pr | Allyl | H | H | Na | T1 | |
| 941. | Pr | Allyl | H | H | H | T2 | |
| 942. | Pr | Allyl | H | H | Na | T2 | |
| 943. | Pr | Allyl | H | H | H | T5 | |
| 944. | Pr | Allyl | H | H | Na | T5 | |
| 945. | Pr | Allyl | H | H | H | T6 | |
| 946. | Pr | Allyl | H | H | Na | T6 | |
| 947. | Pr | Allyl | H | H | H | T7 | |
| 948. | Pr | Allyl | H | H | Na | T7 | |
| 949. | i-Pr | Allyl | H | H | H | T1 | |
| 950. | i-Pr | Allyl | H | H | Na | T1 | |
| 951. | i-Pr | Allyl | H | H | H | T2 | |
| 952. | i-Pr | Allyl | H | H | Na | T2 | |
| 953. | i-Pr | Allyl | H | H | H | T5 | |
| 954. | i-Pr | Allyl | H | H | Na | T5 | |
| 955. | i-Pr | Allyl | H | H | H | T6 | |
| 956. | i-Pr | Allyl | H | H | Na | T6 | |
| 957. | i-Pr | Allyl | H | H | H | T7 | |
| 958. | i-Pr | Allyl | H | H | Na | T7 | |
| 959. | c-Pr | Allyl | H | H | H | T1 | |
| 960. | c-Pr | Allyl | H | H | Na | T1 | |
| 961. | c-Pr | Allyl | H | H | H | T2 | |
| 962. | c-Pr | Allyl | H | H | Na | T2 | |
| 963. | c-Pr | Allyl | H | H | H | T5 | |
| 964. | c-Pr | Allyl | H | H | Na | T5 | |
| 965. | c-Pr | Allyl | H | H | H | T6 | |
| 966. | c-Pr | Allyl | H | H | Na | T6 | |
| 967. | c-Pr | Allyl | H | H | H | T7 | |
| 968. | c-Pr | Allyl | H | H | Na | T7 | |
| 969. | Bu | Allyl | H | H | H | T1 | |

TABLE 1-continued

Compounds of the formula (Ia)

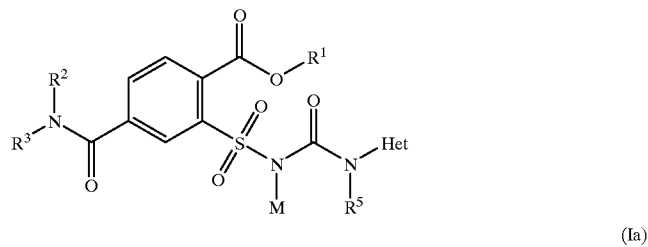

(Ia)

| Ex. | R¹ | R² | R³ | R⁵ | M | Het | m.p. |
|---|---|---|---|---|---|---|---|
| 970. | Bu | Allyl | H | H | Na | T1 | |
| 971. | Bu | Allyl | H | H | H | T2 | |
| 972. | Bu | Allyl | H | H | Na | T2 | |
| 973. | Bu | Allyl | H | H | H | T5 | |
| 974. | Bu | Allyl | H | H | Na | T5 | |
| 975. | Bu | Allyl | H | H | H | T6 | |
| 976. | Bu | Allyl | H | H | Na | T6 | |
| 977. | Bu | Allyl | H | H | H | T7 | |
| 978. | Bu | Allyl | H | H | Na | T7 | |
| 979. | $CH_2$-c-Pr | Allyl | H | H | H | T1 | |
| 980. | $CH_2$-c-Pr | Allyl | H | H | Na | T1 | |
| 981. | $CH_2$-c-Pr | Allyl | H | H | H | T2 | |
| 982. | $CH_2$-c-Pr | Allyl | H | H | Na | T2 | |
| 983. | $CH_2$-c-Pr | Allyl | H | H | H | T5 | |
| 984. | $CH_2$-c-Pr | Allyl | H | H | Na | T5 | |
| 985. | $CH_2$-c-Pr | Allyl | H | H | H | T6 | |
| 986. | $CH_2$-c-Pr | Allyl | H | H | Na | T6 | |
| 987. | $CH_2$-c-Pr | Allyl | H | H | H | T7 | |
| 988. | $CH_2$-c-Pr | Allyl | H | H | Na | T7 | |
| 989. | $CH_2CH_2F$ | Allyl | H | H | H | T1 | |
| 990. | $CH_2CH_2F$ | Allyl | H | H | Na | T1 | |
| 991. | $CH_2CH_2F$ | Allyl | H | H | H | T2 | |
| 992. | $CH_2CH_2F$ | Allyl | H | H | Na | T2 | |
| 993. | $CH_2CH_2F$ | Allyl | H | H | H | T5 | |
| 994. | $CH_2CH_2F$ | Allyl | H | H | Na | T5 | |
| 995. | $CH_2CH_2F$ | Allyl | H | H | H | T6 | |
| 996. | $CH_2CH_2F$ | Allyl | H | H | Na | T6 | |
| 997. | $CH_2CH_2F$ | Allyl | H | H | H | T7 | |
| 998. | $CH_2CH_2F$ | Allyl | H | H | Na | T7 | |
| 999. | $CH_2CH_2CF_3$ | Allyl | H | H | H | T1 | |
| 1000. | $CH_2CH_2CF_3$ | Allyl | H | H | Na | T1 | |
| 1001. | $CH_2CH_2CF_3$ | Allyl | H | H | H | T2 | |
| 1002. | $CH_2CH_2CF_3$ | Allyl | H | H | Na | T2 | |
| 1003. | $CH_2CH_2CF_3$ | Allyl | H | H | H | T5 | |
| 1004. | $CH_2CH_2CF_3$ | Allyl | H | H | Na | T5 | |
| 1005. | $CH_2CH_2CF_3$ | Allyl | H | H | H | T6 | |
| 1006. | $CH_2CH_2CF_3$ | Allyl | H | H | Na | T6 | |
| 1007. | $CH_2CH_2CF_3$ | Allyl | H | H | H | T7 | |
| 1008. | $CH_2CH_2CF_3$ | Allyl | H | H | Na | T7 | |
| 1009. | 3-Oxetanyl | Allyl | H | H | H | T1 | |
| 1010. | 3-Oxetanyl | Allyl | H | H | Na | T1 | |
| 1011. | 3-Oxetanyl | Allyl | H | H | H | T2 | |
| 1012. | 3-Oxetanyl | Allyl | H | H | Na | T2 | |
| 1013. | 3-Oxetanyl | Allyl | H | H | H | T5 | |
| 1014. | 3-Oxetanyl | Allyl | H | H | Na | T5 | |
| 1015. | 3-Oxetanyl | Allyl | H | H | H | T6 | |
| 1016. | 3-Oxetanyl | Allyl | H | H | Na | T6 | |
| 1017. | 3-Oxetanyl | Allyl | H | H | H | T7 | |
| 1018. | 3-Oxetanyl | Allyl | H | H | Na | T7 | |
| 1019. | Et | Allyl | Me | H | H | T1 | 180–182 |
| 1020. | Et | Allyl | Me | H | Na | T1 | 218–221 |
| 1021. | Et | Allyl | Me | H | H | T2 | |
| 1022. | Et | Allyl | Me | H | Na | T2 | |
| 1023. | Et | Allyl | Me | H | H | T5 | |
| 1024. | Et | Allyl | Me | H | Na | T5 | |
| 1025. | Et | Allyl | Me | H | H | T6 | |
| 1026. | Et | Allyl | Me | H | Na | T6 | |
| 1027. | Et | Allyl | Me | H | H | T7 | |
| 1028. | Et | Allyl | Me | H | Na | T7 | |
| 1029. | Pr | Allyl | Me | H | H | T1 | |
| 1030. | Pr | Allyl | Me | H | Na | T1 | |
| 1031. | Pr | Allyl | Me | H | H | T2 | |

TABLE 1-continued

Compounds of the formula (Ia)

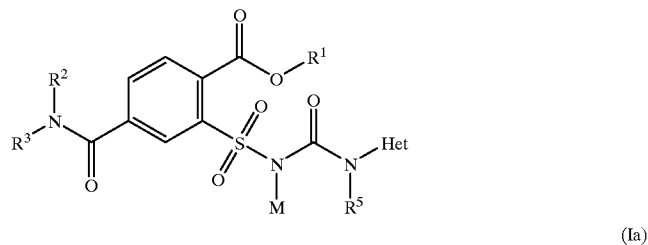

(Ia)

| Ex. | R¹ | R² | R³ | R⁵ | M | Het | m.p. |
|---|---|---|---|---|---|---|---|
| 1032. | Pr | Allyl | Me | H | Na | T2 | |
| 1033. | Pr | Allyl | Me | H | H | T5 | |
| 1034. | Pr | Allyl | Me | H | Na | T5 | |
| 1035. | Pr | Allyl | Me | H | H | T6 | |
| 1036. | Pr | Allyl | Me | H | Na | T6 | |
| 1037. | Pr | Allyl | Me | H | H | T7 | |
| 1038. | Pr | Allyl | Me | H | Na | T7 | |
| 1039. | i-Pr | Allyl | Me | H | H | T1 | |
| 1040. | i-Pr | Allyl | Me | H | Na | T1 | |
| 1041. | i-Pr | Allyl | Me | H | H | T2 | |
| 1042. | i-Pr | Allyl | Me | H | Na | T2 | |
| 1043. | i-Pr | Allyl | Me | H | H | T5 | |
| 1044. | i-Pr | Allyl | Me | H | Na | T5 | |
| 1045. | i-Pr | Allyl | Me | H | H | T6 | |
| 1046. | i-Pr | Allyl | Me | H | Na | T6 | |
| 1047. | i-Pr | Allyl | Me | H | H | T7 | |
| 1048. | i-Pr | Allyl | Me | H | Na | T7 | |
| 1049. | c-Pr | Allyl | Me | H | H | T1 | |
| 1050. | c-Pr | Allyl | Me | H | Na | T1 | |
| 1051. | c-Pr | Allyl | Me | H | H | T2 | |
| 1052. | c-Pr | Allyl | Me | H | Na | T2 | |
| 1053. | c-Pr | Allyl | Me | H | H | T5 | |
| 1054. | c-Pr | Allyl | Me | H | Na | T5 | |
| 1055. | c-Pr | Allyl | Me | H | H | T6 | |
| 1056. | c-Pr | Allyl | Me | H | Na | T6 | |
| 1057. | c-Pr | Allyl | Me | H | H | T7 | |
| 1058. | c-Pr | Allyl | Me | H | Na | T7 | |
| 1059. | Bu | Allyl | Me | H | H | T1 | |
| 1060. | Bu | Allyl | Me | H | Na | T1 | |
| 1061. | Bu | Allyl | Me | H | H | T2 | |
| 1062. | Bu | Allyl | Me | H | Na | T2 | |
| 1063. | Bu | Allyl | Me | H | H | T5 | |
| 1064. | Bu | Allyl | Me | H | Na | T5 | |
| 1065. | Bu | Allyl | Me | H | H | T6 | |
| 1066. | Bu | Allyl | Me | H | Na | T6 | |
| 1067. | Bu | Allyl | Me | H | H | T7 | |
| 1068. | Bu | Allyl | Me | H | Na | T7 | |
| 1069. | CH₂-c-Pr | Allyl | Me | H | H | T1 | |
| 1070. | CH₂-c-Pr | Allyl | Me | H | Na | T1 | |
| 1071. | CH₂-c-Pr | Allyl | Me | H | H | T2 | |
| 1072. | CH₂-c-Pr | Allyl | Me | H | Na | T2 | |
| 1073. | CH₂-c-Pr | Allyl | Me | H | H | T5 | |
| 1074. | CH₂-c-Pr | Allyl | Me | H | Na | T5 | |
| 1075. | CH₂-c-Pr | Allyl | Me | H | H | T6 | |
| 1076. | CH₂-c-Pr | Allyl | Me | H | Na | T6 | |
| 1077. | CH₂-c-Pr | Allyl | Me | H | H | T7 | |
| 1078. | CH₂-c-Pr | Allyl | Me | H | Na | T7 | |
| 1079. | CH₂CH₂F | Allyl | Me | H | H | T1 | |
| 1080. | CH₂CH₂F | Allyl | Me | H | Na | T1 | |
| 1081. | CH₂CH₂F | Allyl | Me | H | H | T2 | |
| 1082. | CH₂CH₂F | Allyl | Me | H | Na | T2 | |
| 1083. | CH₂CH₂F | Allyl | Me | H | H | T5 | |
| 1084. | CH₂CH₂F | Allyl | Me | H | Na | T5 | |
| 1085. | CH₂CH₂F | Allyl | Me | H | H | T6 | |
| 1086. | CH₂CH₂F | Allyl | Me | H | Na | T6 | |
| 1087. | CH₂CH₂F | Allyl | Me | H | H | T7 | |
| 1088. | CH₂CH₂F | Allyl | Me | H | Na | T7 | |
| 1089. | CH₂CH₂CF₃ | Allyl | Me | H | H | T1 | |
| 1090. | CH₂CH₂CF₃ | Allyl | Me | H | Na | T1 | |
| 1091. | CH₂CH₂CF₃ | Allyl | Me | H | H | T2 | |
| 1092. | CH₂CH₂CF₃ | Allyl | Me | H | Na | T2 | |
| 1093. | CH₂CH₂CF₃ | Allyl | Me | H | H | T5 | |

TABLE 1-continued

Compounds of the formula (Ia)

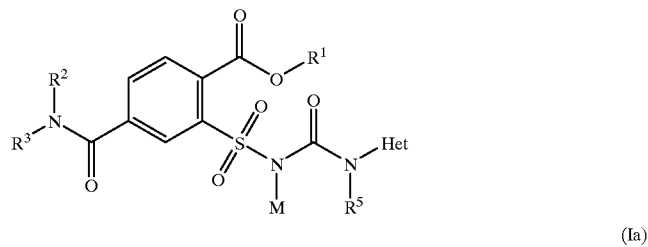

(Ia)

| Ex. | R¹ | R² | R³ | R⁵ | M | Het | m.p. |
|---|---|---|---|---|---|---|---|
| 1094. | CH₂CH₂CF₃ | Allyl | Me | H | Na | T5 | |
| 1095. | CH₂CH₂CF₃ | Allyl | Me | H | H | T6 | |
| 1096. | CH₂CH₂CF₃ | Allyl | Me | H | Na | T6 | |
| 1097. | CH₂CH₂CF₃ | Allyl | Me | H | H | T7 | |
| 1098. | CH₂CH₂CF₃ | Allyl | Me | H | Na | T7 | |
| 1099. | 3-Oxetanyl | Allyl | Me | H | H | T1 | |
| 1100. | 3-Oxetanyl | Allyl | Me | H | Na | T1 | |
| 1101. | 3-Oxetanyl | Allyl | Me | H | H | T2 | |
| 1102. | 3-Oxetanyl | Allyl | Me | H | Na | T2 | |
| 1103. | 3-Oxetanyl | Allyl | Me | H | H | T5 | |
| 1104. | 3-Oxetanyl | Allyl | Me | H | Na | T5 | |
| 1105. | 3-Oxetanyl | Allyl | Me | H | H | T6 | |
| 1106. | 3-Oxetanyl | Allyl | Me | H | Na | T6 | |
| 1107. | 3-Oxetanyl | Allyl | Me | H | H | T7 | |
| 1108. | 3-Oxetanyl | Allyl | Me | H | Na | T7 | |
| 1109. | Et | Allyl | Et | H | H | T1 | |
| 1110. | Et | Allyl | Et | H | Na | T1 | |
| 1111. | Et | Allyl | Et | H | H | T2 | |
| 1112. | Et | Allyl | Et | H | Na | T2 | |
| 1113. | Et | Allyl | Et | H | H | T5 | |
| 1114. | Et | Allyl | Et | H | Na | T5 | |
| 1115. | Et | Allyl | Et | H | H | T6 | |
| 1116. | Et | Allyl | Et | H | Na | T6 | |
| 1117. | Et | Allyl | Et | H | H | T7 | |
| 1118. | Et | Allyl | Et | H | Na | T7 | |
| 1119. | Pr | Allyl | Et | H | H | T1 | |
| 1120. | Pr | Allyl | Et | H | Na | T1 | |
| 1121. | Pr | Allyl | Et | H | H | T2 | |
| 1122. | Pr | Allyl | Et | H | Na | T2 | |
| 1123. | Pr | Allyl | Et | H | H | T5 | |
| 1124. | Pr | Allyl | Et | H | Na | T5 | |
| 1125. | Pr | Allyl | Et | H | H | T6 | |
| 1126. | Pr | Allyl | Et | H | Na | T6 | |
| 1127. | Pr | Allyl | Et | H | H | T7 | |
| 1128. | Pr | Allyl | Et | H | Na | T7 | |
| 1129. | i-Pr | Allyl | Et | H | H | T1 | |
| 1130. | i-Pr | Allyl | Et | H | Na | T1 | |
| 1131. | i-Pr | Allyl | Et | H | H | T2 | |
| 1132. | i-Pr | Allyl | Et | H | Na | T2 | |
| 1133. | i-Pr | Allyl | Et | H | H | T5 | |
| 1134. | i-Pr | Allyl | Et | H | Na | T5 | |
| 1135. | i-Pr | Allyl | Et | H | H | T6 | |
| 1136. | i-Pr | Allyl | Et | H | Na | T6 | |
| 1137. | i-Pr | Allyl | Et | H | H | T7 | |
| 1138. | i-Pr | Allyl | Et | H | Na | T7 | |
| 1139. | c-Pr | Allyl | Et | H | H | T1 | |
| 1140. | c-Pr | Allyl | Et | H | Na | T1 | |
| 1141. | c-Pr | Allyl | Et | H | H | T2 | |
| 1142. | c-Pr | Allyl | Et | H | Na | T2 | |
| 1143. | c-Pr | Allyl | Et | H | H | T5 | |
| 1144. | c-Pr | Allyl | Et | H | Na | T5 | |
| 1145. | c-Pr | Allyl | Et | H | H | T6 | |
| 1146. | c-Pr | Allyl | Et | H | Na | T6 | |
| 1147. | c-Pr | Allyl | Et | H | H | T7 | |
| 1148. | c-Pr | Allyl | Et | H | Na | T7 | |
| 1149. | Bu | Allyl | Et | H | H | T1 | |
| 1150. | Bu | Allyl | Et | H | Na | T1 | |
| 1151. | Bu | Allyl | Et | H | H | T2 | |
| 1152. | Bu | Allyl | Et | H | Na | T2 | |
| 1153. | Bu | Allyl | Et | H | H | T5 | |
| 1154. | Bu | Allyl | Et | H | Na | T5 | |
| 1155. | Bu | Allyl | Et | H | H | T6 | |

TABLE 1-continued

Compounds of the formula (Ia)

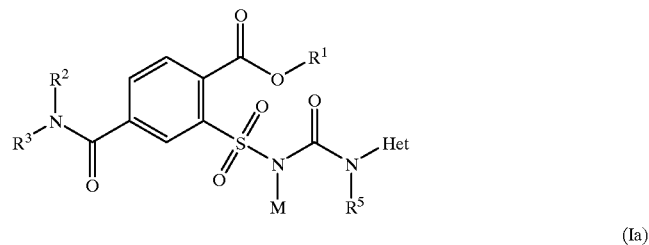

(Ia)

| Ex. | R¹ | R² | R³ | R⁵ | M | Het | m.p. |
|---|---|---|---|---|---|---|---|
| 1156. | Bu | Allyl | Et | H | Na | T6 | |
| 1157. | Bu | Allyl | Et | H | H | T7 | |
| 1158. | Bu | Allyl | Et | H | Na | T7 | |
| 1159. | CH₂-c-Pr | Allyl | Et | H | H | T1 | |
| 1160. | CH₂-c-Pr | Allyl | Et | H | Na | T1 | |
| 1161. | CH₂-c-Pr | Allyl | Et | H | H | T2 | |
| 1162. | CH₂-c-Pr | Allyl | Et | H | Na | T2 | |
| 1163. | CH₂-c-Pr | Allyl | Et | H | H | T5 | |
| 1164. | CH₂-c-Pr | Allyl | Et | H | Na | T5 | |
| 1165. | CH₂-c-Pr | Allyl | Et | H | H | T6 | |
| 1166. | CH₂-c-Pr | Allyl | Et | H | Na | T6 | |
| 1167. | CH₂-c-Pr | Allyl | Et | H | H | T7 | |
| 1168. | CH₂-c-Pr | Allyl | Et | H | Na | T7 | |
| 1169. | CH₂CH₂F | Allyl | Et | H | H | T1 | |
| 1170. | CH₂CH₂F | Allyl | Et | H | Na | T1 | |
| 1171. | CH₂CH₂F | Allyl | Et | H | H | T2 | |
| 1172. | CH₂CH₂F | Allyl | Et | H | Na | T2 | |
| 1173. | CH₂CH₂F | Allyl | Et | H | H | T5 | |
| 1174. | CH₂CH₂F | Allyl | Et | H | Na | T5 | |
| 1175. | CH₂CH₂F | Allyl | Et | H | H | T6 | |
| 1176. | CH₂CH₂F | Allyl | Et | H | Na | T6 | |
| 1177. | CH₂CH₂F | Allyl | Et | H | H | T7 | |
| 1178. | CH₂CH₂F | Allyl | Et | H | Na | T7 | |
| 1179. | CH₂CH₂CF₃ | Allyl | Et | H | H | T1 | |
| 1180. | CH₂CH₂CF₃ | Allyl | Et | H | Na | T1 | |
| 1181. | CH₂CH₂CF₃ | Allyl | Et | H | H | T2 | |
| 1182. | CH₂CH₂CF₃ | Allyl | Et | H | Na | T2 | |
| 1183. | CH₂CH₂CF₃ | Allyl | Et | H | H | T5 | |
| 1184. | CH₂CH₂CF₃ | Allyl | Et | H | Na | T5 | |
| 1185. | CH₂CH₂CF₃ | Allyl | Et | H | H | T6 | |
| 1186. | CH₂CH₂CF₃ | Allyl | Et | H | Na | T6 | |
| 1187. | CH₂CH₂CF₃ | Allyl | Et | H | H | T7 | |
| 1188. | CH₂CH₂CF₃ | Allyl | Et | H | Na | T7 | |
| 1189. | 3-Oxetanyl | Allyl | Et | H | H | T1 | |
| 1190. | 3-Oxetanyl | Allyl | Et | H | Na | T1 | |
| 1191. | 3-Oxetanyl | Allyl | Et | H | H | T2 | |
| 1192. | 3-Oxetanyl | Allyl | Et | H | Na | T2 | |
| 1193. | 3-Oxetanyl | Allyl | Et | H | H | T5 | |
| 1194. | 3-Oxetanyl | Allyl | Et | H | Na | T5 | |
| 1195. | 3-Oxetanyl | Allyl | Et | H | H | T6 | |
| 1196. | 3-Oxetanyl | Allyl | Et | H | Na | T6 | |
| 1197. | 3-Oxetanyl | Allyl | Et | H | H | T7 | |
| 1198. | 3-Oxetanyl | Allyl | Et | H | Na | T7 | |
| 1199. | Et | Allyl | Pr | H | H | T1 | |
| 1200. | Et | Allyl | Pr | H | Na | T1 | |
| 1201. | Et | Allyl | Pr | H | H | T2 | |
| 1202. | Et | Allyl | Pr | H | Na | T2 | |
| 1203. | Et | Allyl | Pr | H | H | T5 | |
| 1204. | Et | Allyl | Pr | H | Na | T5 | |
| 1205. | Et | Allyl | Pr | H | H | T6 | |
| 1206. | Et | Allyl | Pr | H | Na | T6 | |
| 1207. | Et | Allyl | Pr | H | H | T7 | |
| 1208. | Et | Allyl | Pr | H | Na | T7 | |
| 1209. | Pr | Allyl | Pr | H | H | T1 | |
| 1210. | Pr | Allyl | Pr | H | Na | T1 | |
| 1211. | Pr | Allyl | Pr | H | H | T2 | |
| 1212. | Pr | Allyl | Pr | H | Na | T2 | |
| 1213. | Pr | Allyl | Pr | H | H | T5 | |
| 1214. | Pr | Allyl | Pr | H | Na | T5 | |
| 1215. | Pr | Allyl | Pr | H | H | T6 | |
| 1216. | Pr | Allyl | Pr | H | Na | T6 | |
| 1217. | Pr | Allyl | Pr | H | H | T7 | |

TABLE 1-continued

Compounds of the formula (Ia)

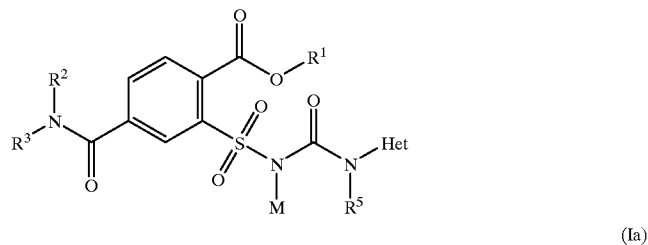

(Ia)

| Ex. | R¹ | R² | R³ | R⁵ | M | Het | m.p. |
|---|---|---|---|---|---|---|---|
| 1218. | Pr | Allyl | Pr | H | Na | T7 | |
| 1219. | i-Pr | Allyl | Pr | H | H | T1 | |
| 1220. | i-Pr | Allyl | Pr | H | Na | T1 | |
| 1221. | i-Pr | Allyl | Pr | H | H | T2 | |
| 1222. | i-Pr | Allyl | Pr | H | Na | T2 | |
| 1223. | i-Pr | Allyl | Pr | H | H | T5 | |
| 1224. | i-Pr | Allyl | Pr | H | Na | T5 | |
| 1225. | i-Pr | Allyl | Pr | H | H | T6 | |
| 1226. | i-Pr | Allyl | Pr | H | Na | T6 | |
| 1227. | i-Pr | Allyl | Pr | H | H | T7 | |
| 1228. | i-Pr | Allyl | Pr | H | Na | T7 | |
| 1229. | c-Pr | Allyl | Pr | H | H | T1 | |
| 1230. | c-Pr | Allyl | Pr | H | Na | T1 | |
| 1231. | c-Pr | Allyl | Pr | H | H | T2 | |
| 1232. | c-Pr | Allyl | Pr | H | Na | T2 | |
| 1233. | c-Pr | Allyl | Pr | H | H | T5 | |
| 1234. | c-Pr | Allyl | Pr | H | Na | T5 | |
| 1235. | c-Pr | Allyl | Pr | H | H | T6 | |
| 1236. | c-Pr | Allyl | Pr | H | Na | T6 | |
| 1237. | c-Pr | Allyl | Pr | H | H | T7 | |
| 1238. | c-Pr | Allyl | Pr | H | Na | T7 | |
| 1239. | Bu | Allyl | Pr | H | H | T1 | |
| 1240. | Bu | Allyl | Pr | H | Na | T1 | |
| 1241. | Bu | Allyl | Pr | H | H | T2 | |
| 1242. | Bu | Allyl | Pr | H | Na | T2 | |
| 1243. | Bu | Allyl | Pr | H | H | T5 | |
| 1244. | Bu | Allyl | Pr | H | Na | T5 | |
| 1245. | Bu | Allyl | Pr | H | H | T6 | |
| 1246. | Bu | Allyl | Pr | H | Na | T6 | |
| 1247. | Bu | Allyl | Pr | H | H | T7 | |
| 1248. | Bu | Allyl | Pr | H | Na | T7 | |
| 1249. | $CH_2$-c-Pr | Allyl | Pr | H | H | T1 | |
| 1250. | $CH_2$-c-Pr | Allyl | Pr | H | Na | T1 | |
| 1251. | $CH_2$-c-Pr | Allyl | Pr | H | H | T2 | |
| 1252. | $CH_2$-c-Pr | Allyl | Pr | H | Na | T2 | |
| 1253. | $CH_2$-c-Pr | Allyl | Pr | H | H | T5 | |
| 1254. | $CH_2$-c-Pr | Allyl | Pr | H | Na | T5 | |
| 1255. | $CH_2$-c-Pr | Allyl | Pr | H | H | T6 | |
| 1256. | $CH_2$-c-Pr | Allyl | Pr | H | Na | T6 | |
| 1257. | $CH_2$-c-Pr | Allyl | Pr | H | H | T7 | |
| 1258. | $CH_2$-c-Pr | Allyl | Pr | H | Na | T7 | |
| 1259. | $CH_2CH_2F$ | Allyl | Pr | H | H | T1 | |
| 1260. | $CH_2CH_2F$ | Allyl | Pr | H | Na | T1 | |
| 1261. | $CH_2CH_2F$ | Allyl | Pr | H | H | T2 | |
| 1262. | $CH_2CH_2F$ | Allyl | Pr | H | Na | T2 | |
| 1263. | $CH_2CH_2F$ | Allyl | Pr | H | H | T5 | |
| 1264. | $CH_2CH_2F$ | Allyl | Pr | H | Na | T5 | |
| 1265. | $CH_2CH_2F$ | Allyl | Pr | H | H | T6 | |
| 1266. | $CH_2CH_2F$ | Allyl | Pr | H | Na | T6 | |
| 1267. | $CH_2CH_2F$ | Allyl | Pr | H | H | T7 | |
| 1268. | $CH_2CH_2F$ | Allyl | Pr | H | Na | T7 | |
| 1269. | $CH_2CH_2CF_3$ | Allyl | Pr | H | H | T1 | |
| 1270. | $CH_2CH_2CF_3$ | Allyl | Pr | H | Na | T1 | |
| 1271. | $CH_2CH_2CF_3$ | Allyl | Pr | H | H | T2 | |
| 1272. | $CH_2CH_2CF_3$ | Allyl | Pr | H | Na | T2 | |
| 1273. | $CH_2CH_2CF_3$ | Allyl | Pr | H | H | T5 | |
| 1274. | $CH_2CH_2CF_3$ | Allyl | Pr | H | Na | T5 | |
| 1275. | $CH_2CH_2CF_3$ | Allyl | Pr | H | H | T6 | |
| 1276. | $CH_2CH_2CF_3$ | Allyl | Pr | H | Na | T6 | |
| 1277. | $CH_2CH_2CF_3$ | Allyl | Pr | H | H | T7 | |
| 1278. | $CH_2CH_2CF_3$ | Allyl | Pr | H | Na | T7 | |
| 1279. | 3-Oxetanyl | Allyl | Pr | H | H | T1 | |

TABLE 1-continued

Compounds of the formula (Ia)

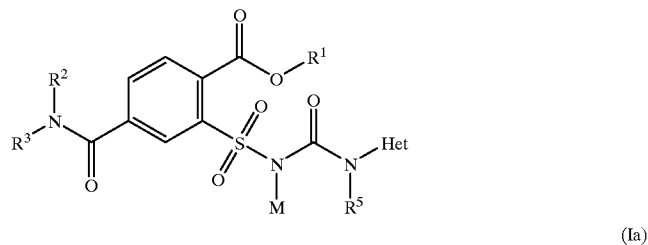

(Ia)

| Ex. | R¹ | R² | R³ | R⁵ | M | Het | m.p. |
|---|---|---|---|---|---|---|---|
| 1280. | 3-Oxetanyl | Allyl | Pr | H | Na | T1 | |
| 1281. | 3-Oxetanyl | Allyl | Pr | H | H | T2 | |
| 1282. | 3-Oxetanyl | Allyl | Pr | H | Na | T2 | |
| 1283. | 3-Oxetanyl | Allyl | Pr | H | H | T5 | |
| 1284. | 3-Oxetanyl | Allyl | Pr | H | Na | T5 | |
| 1285. | 3-Oxetanyl | Allyl | Pr | H | H | T6 | |
| 1286. | 3-Oxetanyl | Allyl | Pr | H | Na | T6 | |
| 1287. | 3-Oxetanyl | Allyl | Pr | H | H | T7 | |
| 1288. | 3-Oxetanyl | Allyl | Pr | H | Na | T7 | |
| 1289. | Et | Allyl | i-Pr | H | H | T1 | 144–147 |
| 1290. | Et | Allyl | i-Pr | H | Na | T1 | 179–183 |
| 1291. | Et | Allyl | i-Pr | H | H | T2 | |
| 1292. | Et | Allyl | i-Pr | H | Na | T2 | |
| 1293. | Et | Allyl | i-Pr | H | H | T5 | |
| 1294. | Et | Allyl | i-Pr | H | Na | T5 | |
| 1295. | Et | Allyl | i-Pr | H | H | T6 | |
| 1296. | Et | Allyl | i-Pr | H | Na | T6 | |
| 1297. | Et | Allyl | i-Pr | H | H | T7 | |
| 1298. | Et | Allyl | i-Pr | H | Na | T7 | |
| 1299. | Pr | Allyl | i-Pr | H | H | T1 | |
| 1300. | Pr | Allyl | i-Pr | H | Na | T1 | |
| 1301. | Pr | Allyl | i-Pr | H | H | T2 | |
| 1302. | Pr | Allyl | i-Pr | H | Na | T2 | |
| 1303. | Pr | Allyl | i-Pr | H | H | T5 | |
| 1304. | Pr | Allyl | i-Pr | H | Na | T5 | |
| 1305. | Pr | Allyl | i-Pr | H | H | T6 | |
| 1306. | Pr | Allyl | i-Pr | H | Na | T6 | |
| 1307. | Pr | Allyl | i-Pr | H | H | T7 | |
| 1308. | Pr | Allyl | i-Pr | H | Na | T7 | |
| 1309. | i-Pr | Allyl | i-Pr | H | H | T1 | |
| 1310. | i-Pr | Allyl | i-Pr | H | Na | T1 | |
| 1311. | i-Pr | Allyl | i-Pr | H | H | T2 | |
| 1312. | i-Pr | Allyl | i-Pr | H | Na | T2 | |
| 1313. | i-Pr | Allyl | i-Pr | H | H | T5 | |
| 1314. | i-Pr | Allyl | i-Pr | H | Na | T5 | |
| 1315. | i-Pr | Allyl | i-Pr | H | H | T6 | |
| 1316. | i-Pr | Allyl | i-Pr | H | Na | T6 | |
| 1317. | i-Pr | Allyl | i-Pr | H | H | T7 | |
| 1318. | i-Pr | Allyl | i-Pr | H | Na | T7 | |
| 1319. | c-Pr | Allyl | i-Pr | H | H | T1 | |
| 1320. | c-Pr | Allyl | i-Pr | H | Na | T1 | |
| 1321. | c-Pr | Allyl | i-Pr | H | H | T2 | |
| 1322. | c-Pr | Allyl | i-Pr | H | Na | T2 | |
| 1323. | c-Pr | Allyl | i-Pr | H | H | T5 | |
| 1324. | c-Pr | Allyl | i-Pr | H | Na | T5 | |
| 1325. | c-Pr | Allyl | i-Pr | H | H | T6 | |
| 1326. | c-Pr | Allyl | i-Pr | H | Na | T6 | |
| 1327. | c-Pr | Allyl | i-Pr | H | H | T7 | |
| 1328. | c-Pr | Allyl | i-Pr | H | Na | T7 | |
| 1329. | Bu | Allyl | i-Pr | H | H | T1 | |
| 1330. | Bu | Allyl | i-Pr | H | Na | T1 | |
| 1331. | Bu | Allyl | i-Pr | H | H | T2 | |
| 1332. | Bu | Allyl | i-Pr | H | Na | T2 | |
| 1333. | Bu | Allyl | i-Pr | H | H | T5 | |
| 1334. | Bu | Allyl | i-Pr | H | Na | T5 | |
| 1335. | Bu | Allyl | i-Pr | H | H | T6 | |
| 1336. | Bu | Allyl | i-Pr | H | Na | T6 | |
| 1337. | Bu | Allyl | i-Pr | H | H | T7 | |
| 1338. | Bu | Allyl | i-Pr | H | Na | T7 | |
| 1339. | CH₂-c-Pr | Allyl | i-Pr | H | H | T1 | |
| 1340. | CH₂-c-Pr | Allyl | i-Pr | H | Na | T1 | |
| 1341. | CH₂-c-Pr | Allyl | i-Pr | H | H | T2 | |

TABLE 1-continued

Compounds of the formula (Ia)

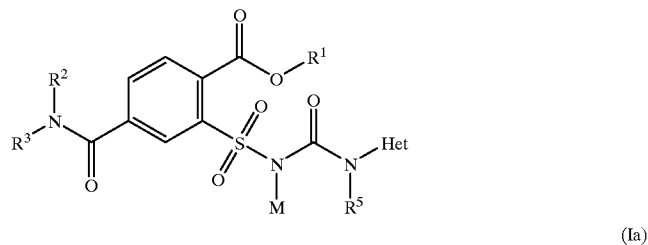

(Ia)

| Ex. | R¹ | R² | R³ | R⁵ | M | Het | m.p. |
|---|---|---|---|---|---|---|---|
| 1342. | CH₂-c-Pr | Allyl | i-Pr | H | Na | T2 | |
| 1343. | CH₂-c-Pr | Allyl | i-Pr | H | H | T5 | |
| 1344. | CH₂-c-Pr | Allyl | i-Pr | H | Na | T5 | |
| 1345. | CH₂-c-Pr | Allyl | i-Pr | H | H | T6 | |
| 1346. | CH₂-c-Pr | Allyl | i-Pr | H | Na | T6 | |
| 1347. | CH₂-c-Pr | Allyl | i-Pr | H | H | T7 | |
| 1348. | CH₂-c-Pr | Allyl | i-Pr | H | Na | T7 | |
| 1349. | CH₂CH₂F | Allyl | i-Pr | H | H | T1 | |
| 1350. | CH₂CH₂F | Allyl | i-Pr | H | Na | T1 | |
| 1351. | CH₂CH₂F | Allyl | i-Pr | H | H | T2 | |
| 1352. | CH₂CH₂F | Allyl | i-Pr | H | Na | T2 | |
| 1353. | CH₂CH₂F | Allyl | i-Pr | H | H | T5 | |
| 1354. | CH₂CH₂F | Allyl | i-Pr | H | Na | T5 | |
| 1355. | CH₂CH₂F | Allyl | i-Pr | H | H | T6 | |
| 1356. | CH₂CH₂F | Allyl | i-Pr | H | Na | T6 | |
| 1357. | CH₂CH₂F | Allyl | i-Pr | H | H | T7 | |
| 1358. | CH₂CH₂F | Allyl | i-Pr | H | Na | T7 | |
| 1359. | CH₂CH₂CF₃ | Allyl | i-Pr | H | H | T1 | |
| 1360. | CH₂CH₂CF₃ | Allyl | i-Pr | H | Na | T1 | |
| 1361. | CH₂CH₂CF₃ | Allyl | i-Pr | H | H | T2 | |
| 1362. | CH₂CH₂CF₃ | Allyl | i-Pr | H | Na | T2 | |
| 1363. | CH₂CH₂CF₃ | Allyl | i-Pr | H | H | T5 | |
| 1364. | CH₂CH₂CF₃ | Allyl | i-Pr | H | Na | T5 | |
| 1365. | CH₂CH₂CF₃ | Allyl | i-Pr | H | H | T6 | |
| 1366. | CH₂CH₂CF₃ | Allyl | i-Pr | H | Na | T6 | |
| 1367. | CH₂CH₂CF₃ | Allyl | i-Pr | H | H | T7 | |
| 1368. | CH₂CH₂CF₃ | Allyl | i-Pr | H | Na | T7 | |
| 1369. | 3-Oxetanyl | Allyl | i-Pr | H | H | T1 | |
| 1370. | 3-Oxetanyl | Allyl | i-Pr | H | Na | T1 | |
| 1371. | 3-Oxetanyl | Allyl | i-Pr | H | H | T2 | |
| 1372. | 3-Oxetanyl | Allyl | i-Pr | H | Na | T2 | |
| 1373. | 3-Oxetanyl | Allyl | i-Pr | H | H | T5 | |
| 1374. | 3-Oxetanyl | Allyl | i-Pr | H | Na | T5 | |
| 1375. | 3-Oxetanyl | Allyl | i-Pr | H | H | T6 | |
| 1376. | 3-Oxetanyl | Allyl | i-Pr | H | Na | T6 | |
| 1377. | 3-Oxetanyl | Allyl | i-Pr | H | H | T7 | |
| 1378. | 3-Oxetanyl | Allyl | i-Pr | H | Na | T7 | |
| 1379. | Et | Propargyl | H | H | H | T1 | |
| 1380. | Et | Propargyl | H | H | Na | T1 | |
| 1381. | Et | Propargyl | H | H | H | T2 | |
| 1382. | Et | Propargyl | H | H | Na | T2 | |
| 1383. | Et | Propargyl | H | H | H | T5 | |
| 1384. | Et | Propargyl | H | H | Na | T5 | |
| 1385. | Et | Propargyl | H | H | H | T6 | |
| 1386. | Et | Propargyl | H | H | Na | T6 | |
| 1387. | Et | Propargyl | H | H | H | T7 | |
| 1388. | Et | Propargyl | H | H | Na | T7 | |
| 1389. | Pr | Propargyl | H | H | H | T1 | |
| 1390. | Pr | Propargyl | H | H | Na | T1 | |
| 1391. | Pr | Propargyl | H | H | H | T2 | |
| 1392. | Pr | Propargyl | H | H | Na | T2 | |
| 1393. | Pr | Propargyl | H | H | H | T5 | |
| 1394. | Pr | Propargyl | H | H | Na | T5 | |
| 1395. | Pr | Propargyl | H | H | H | T6 | |
| 1396. | Pr | Propargyl | H | H | Na | T6 | |
| 1397. | Pr | Propargyl | H | H | H | T7 | |
| 1398. | Pr | Propargyl | H | H | Na | T7 | |
| 1399. | i-Pr | Propargyl | H | H | H | T1 | |
| 1400. | i-Pr | Propargyl | H | H | Na | T1 | |
| 1401. | i-Pr | Propargyl | H | H | H | T2 | |
| 1402. | i-Pr | Propargyl | H | H | Na | T2 | |
| 1403. | i-Pr | Propargyl | H | H | H | T5 | |

TABLE 1-continued

Compounds of the formula (Ia)

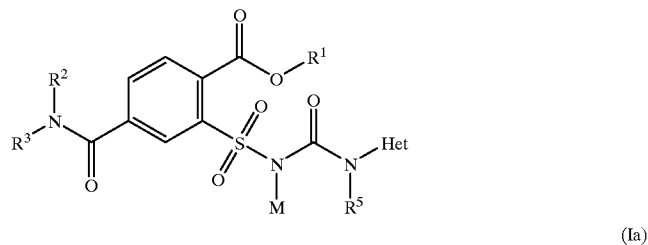

(Ia)

| Ex. | R¹ | R² | R³ | R⁵ | M | Het | m.p. |
|---|---|---|---|---|---|---|---|
| 1404. | i-Pr | Propargyl | H | H | Na | T5 | |
| 1405. | i-Pr | Propargyl | H | H | H | T6 | |
| 1406. | i-Pr | Propargyl | H | H | Na | T6 | |
| 1407. | i-Pr | Propargyl | H | H | H | T7 | |
| 1408. | i-Pr | Propargyl | H | H | Na | T7 | |
| 1409. | c-Pr | Propargyl | H | H | H | T1 | |
| 1410. | c-Pr | Propargyl | H | H | Na | T1 | |
| 1411. | c-Pr | Propargyl | H | H | H | T2 | |
| 1412. | c-Pr | Propargyl | H | H | Na | T2 | |
| 1413. | c-Pr | Propargyl | H | H | H | T5 | |
| 1414. | c-Pr | Propargyl | H | H | Na | T5 | |
| 1415. | c-Pr | Propargyl | H | H | H | T6 | |
| 1416. | c-Pr | Propargyl | H | H | Na | T6 | |
| 1417. | c-Pr | Propargyl | H | H | H | T7 | |
| 1418. | c-Pr | Propargyl | H | H | Na | T7 | |
| 1419. | Bu | Propargyl | H | H | H | T1 | |
| 1420. | Bu | Propargyl | H | H | Na | T1 | |
| 1421. | Bu | Propargyl | H | H | H | T2 | |
| 1422. | Bu | Propargyl | H | H | Na | T2 | |
| 1423. | Bu | Propargyl | H | H | H | T5 | |
| 1424. | Bu | Propargyl | H | H | Na | T5 | |
| 1425. | Bu | Propargyl | H | H | H | T6 | |
| 1426. | Bu | Propargyl | H | H | Na | T6 | |
| 1427. | Bu | Propargyl | H | H | H | T7 | |
| 1428. | Bu | Propargyl | H | H | Na | T7 | |
| 1429. | CH₂-c-Pr | Propargyl | H | H | H | T1 | |
| 1430. | CH₂-c-Pr | Propargyl | H | H | Na | T1 | |
| 1431. | CH₂-c-Pr | Propargyl | H | H | H | T2 | |
| 1432. | CH₂-c-Pr | Propargyl | H | H | Na | T2 | |
| 1433. | CH₂-c-Pr | Propargyl | H | H | H | T5 | |
| 1434. | CH₂-c-Pr | Propargyl | H | H | Na | T5 | |
| 1435. | CH₂-c-Pr | Propargyl | H | H | H | T6 | |
| 1436. | CH₂-c-Pr | Propargyl | H | H | Na | T6 | |
| 1437. | CH₂-c-Pr | Propargyl | H | H | H | T7 | |
| 1438. | CH₂-c-Pr | Propargyl | H | H | Na | T7 | |
| 1439. | CH₂CH₂F | Propargyl | H | H | H | T1 | |
| 1440. | CH₂CH₂F | Propargyl | H | H | Na | T1 | |
| 1441. | CH₂CH₂F | Propargyl | H | H | H | T2 | |
| 1442. | CH₂CH₂F | Propargyl | H | H | Na | T2 | |
| 1443. | CH₂CH₂F | Propargyl | H | H | H | T5 | |
| 1444. | CH₂CH₂F | Propargyl | H | H | Na | T5 | |
| 1445. | CH₂CH₂F | Propargyl | H | H | H | T6 | |
| 1446. | CH₂CH₂F | Propargyl | H | H | Na | T6 | |
| 1447. | CH₂CH₂F | Propargyl | H | H | H | T7 | |
| 1448. | CH₂CH₂F | Propargyl | H | H | Na | T7 | |
| 1449. | CH₂CH₂CF₃ | Propargyl | H | H | H | T1 | |
| 1450. | CH₂CH₂CF₃ | Propargyl | H | H | Na | T1 | |
| 1451. | CH₂CH₂CF₃ | Propargyl | H | H | H | T2 | |
| 1452. | CH₂CH₂CF₃ | Propargyl | H | H | Na | T2 | |
| 1453. | CH₂CH₂CF₃ | Propargyl | H | H | H | T5 | |
| 1454. | CH₂CH₂CF₃ | Propargyl | H | H | Na | T5 | |
| 1455. | CH₂CH₂CF₃ | Propargyl | H | H | H | T6 | |
| 1456. | CH₂CH₂CF₃ | Propargyl | H | H | Na | T6 | |
| 1457. | CH₂CH₂CF₃ | Propargyl | H | H | H | T7 | |
| 1458. | CH₂CH₂CF₃ | Propargyl | H | H | Na | T7 | |
| 1459. | 3-Oxetanyl | Propargyl | H | H | H | T1 | |
| 1460. | 3-Oxetanyl | Propargyl | H | H | Na | T1 | |
| 1461. | 3-Oxetanyl | Propargyl | H | H | H | T2 | |
| 1462. | 3-Oxetanyl | Propargyl | H | H | Na | T2 | |
| 1463. | 3-Oxetanyl | Propargyl | H | H | H | T5 | |
| 1464. | 3-Oxetanyl | Propargyl | H | H | Na | T5 | |
| 1465. | 3-Oxetanyl | Propargyl | H | H | H | T6 | |

TABLE 1-continued

Compounds of the formula (Ia)

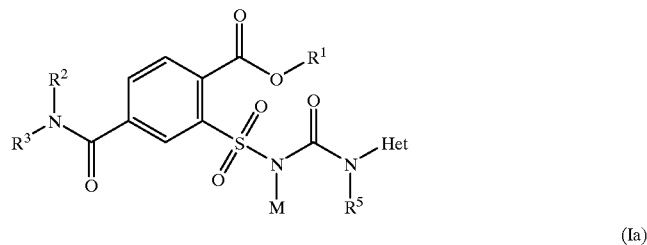

(Ia)

| Ex. | R¹ | R² | R³ | R⁵ | M | Het | m.p. |
|---|---|---|---|---|---|---|---|
| 1466. | 3-Oxetanyl | Propargyl | H | H | Na | T6 | |
| 1467. | 3-Oxetanyl | Propargyl | H | H | H | T7 | |
| 1468. | 3-Oxetanyl | Propargyl | H | H | Na | T7 | |
| 1469. | Et | CH₂CH₂F | H | H | H | T1 | |
| 1470. | Et | CH₂CH₂F | H | H | Na | T1 | |
| 1471. | Et | CH₂CH₂F | H | H | H | T2 | |
| 1472. | Et | CH₂CH₂F | H | H | Na | T2 | |
| 1473. | Et | CH₂CH₂F | H | H | H | T5 | |
| 1474. | Et | CH₂CH₂F | H | H | Na | T5 | |
| 1475. | Et | CH₂CH₂F | H | H | H | T6 | |
| 1476. | Et | CH₂CH₂F | H | H | Na | T6 | |
| 1477. | Et | CH₂CH₂F | H | H | H | T7 | |
| 1478. | Et | CH₂CH₂F | H | H | Na | T7 | |
| 1479. | Pr | CH₂CH₂F | H | H | H | T1 | |
| 1480. | Pr | CH₂CH₂F | H | H | Na | T1 | |
| 1481. | Pr | CH₂CH₂F | H | H | H | T2 | |
| 1482. | Pr | CH₂CH₂F | H | H | Na | T2 | |
| 1483. | Pr | CH₂CH₂F | H | H | H | T5 | |
| 1484. | Pr | CH₂CH₂F | H | H | Na | T5 | |
| 1485. | Pr | CH₂CH₂F | H | H | H | T6 | |
| 1486. | Pr | CH₂CH₂F | H | H | Na | T6 | |
| 1487. | Pr | CH₂CH₂F | H | H | H | T7 | |
| 1488. | Pr | CH₂CH₂F | H | H | Na | T7 | |
| 1489. | i-Pr | CH₂CH₂F | H | H | H | T1 | |
| 1490. | i-Pr | CH₂CH₂F | H | H | Na | T1 | |
| 1491. | i-Pr | CH₂CH₂F | H | H | H | T2 | |
| 1492. | i-Pr | CH₂CH₂F | H | H | Na | T2 | |
| 1493. | i-Pr | CH₂CH₂F | H | H | H | T5 | |
| 1494. | i-Pr | CH₂CH₂F | H | H | Na | T5 | |
| 1495. | i-Pr | CH₂CH₂F | H | H | H | T6 | |
| 1496. | i-Pr | CH₂CH₂F | H | H | Na | T6 | |
| 1497. | i-Pr | CH₂CH₂F | H | H | H | T7 | |
| 1498. | i-Pr | CH₂CH₂F | H | H | Na | T7 | |
| 1499. | c-Pr | CH₂CH₂F | H | H | H | T1 | |
| 1500. | c-Pr | CH₂CH₂F | H | H | Na | T1 | |
| 1501. | c-Pr | CH₂CH₂F | H | H | H | T2 | |
| 1502. | c-Pr | CH₂CH₂F | H | H | Na | T2 | |
| 1503. | c-Pr | CH₂CH₂F | H | H | H | T5 | |
| 1504. | c-Pr | CH₂CH₂F | H | H | Na | T5 | |
| 1505. | c-Pr | CH₂CH₂F | H | H | H | T6 | |
| 1506. | c-Pr | CH₂CH₂F | H | H | Na | T6 | |
| 1507. | c-Pr | CH₂CH₂F | H | H | H | T7 | |
| 1508. | c-Pr | CH₂CH₂F | H | H | Na | T7 | |
| 1509. | Bu | CH₂CH₂F | H | H | H | T1 | |
| 1510. | Bu | CH₂CH₂F | H | H | Na | T1 | |
| 1511. | Bu | CH₂CH₂F | H | H | H | T2 | |
| 1512. | Bu | CH₂CH₂F | H | H | Na | T2 | |
| 1513. | Bu | CH₂CH₂F | H | H | H | T5 | |
| 1514. | Bu | CH₂CH₂F | H | H | Na | T5 | |
| 1515. | Bu | CH₂CH₂F | H | H | H | T6 | |
| 1516. | Bu | CH₂CH₂F | H | H | Na | T6 | |
| 1517. | Bu | CH₂CH₂F | H | H | H | T7 | |
| 1518. | Bu | CH₂CH₂F | H | H | Na | T7 | |
| 1519. | CH₂-c-Pr | CH₂CH₂F | H | H | H | T1 | |
| 1520. | CH₂-c-Pr | CH₂CH₂F | H | H | Na | T1 | |
| 1521. | CH₂-c-Pr | CH₂CH₂F | H | H | H | T2 | |
| 1522. | CH₂-c-Pr | CH₂CH₂F | H | H | Na | T2 | |
| 1523. | CH₂-c-Pr | CH₂CH₂F | H | H | H | T5 | |
| 1524. | CH₂-c-Pr | CH₂CH₂F | H | H | Na | T5 | |
| 1525. | CH₂-c-Pr | CH₂CH₂F | H | H | H | T6 | |
| 1526. | CH₂-c-Pr | CH₂CH₂F | H | H | Na | T6 | |
| 1527. | CH₂-c-Pr | CH₂CH₂F | H | H | H | T7 | |

TABLE 1-continued

Compounds of the formula (Ia)

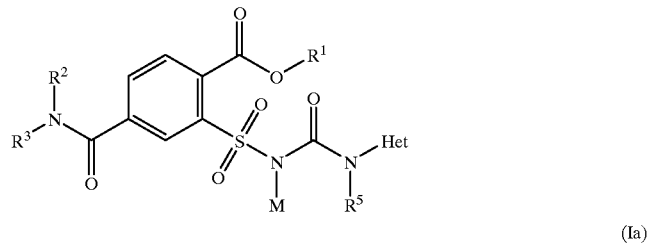

(Ia)

| Ex. | R¹ | R² | R³ | R⁵ | M | Het | m.p. |
|---|---|---|---|---|---|---|---|
| 1528. | CH₂-c-Pr | CH₂CH₂F | H | H | Na | T7 | |
| 1529. | CH₂CH₂F | CH₂CH₂F | H | H | H | T1 | |
| 1530. | CH₂CH₂F | CH₂CH₂F | H | H | Na | T1 | |
| 1531. | CH₂CH₂F | CH₂CH₂F | H | H | H | T2 | |
| 1532. | CH₂CH₂F | CH₂CH₂F | H | H | Na | T2 | |
| 1533. | CH₂CH₂F | CH₂CH₂F | H | H | H | T5 | |
| 1534. | CH₂CH₂F | CH₂CH₂F | H | H | Na | T5 | |
| 1535. | CH₂CH₂F | CH₂CH₂F | H | H | H | T6 | |
| 1536. | CH₂CH₂F | CH₂CH₂F | H | H | Na | T6 | |
| 1537. | CH₂CH₂F | CH₂CH₂F | H | H | H | T7 | |
| 1538. | CH₂CH₂F | CH₂CH₂F | H | H | Na | T7 | |
| 1539. | CH₂CH₂CF₃ | CH₂CH₂F | H | H | H | T1 | |
| 1540. | CH₂CH₂CF₃ | CH₂CH₂F | H | H | Na | T1 | |
| 1541. | CH₂CH₂CF₃ | CH₂CH₂F | H | H | H | T2 | |
| 1542. | CH₂CH₂CF₃ | CH₂CH₂F | H | H | Na | T2 | |
| 1543. | CH₂CH₂CF₃ | CH₂CH₂F | H | H | H | T5 | |
| 1544. | CH₂CH₂CF₃ | CH₂CH₂F | H | H | Na | T5 | |
| 1545. | CH₂CH₂CF₃ | CH₂CH₂F | H | H | H | T6 | |
| 1546. | CH₂CH₂CF₃ | CH₂CH₂F | H | H | Na | T6 | |
| 1547. | CH₂CH₂CF₃ | CH₂CH₂F | H | H | H | T7 | |
| 1548. | CH₂CH₂CF₃ | CH₂CH₂F | H | H | Na | T7 | |
| 1549. | 3-Oxetanyl | CH₂CH₂F | H | H | H | T1 | |
| 1550. | 3-Oxetanyl | CH₂CH₂F | H | H | Na | T1 | |
| 1551. | 3-Oxetanyl | CH₂CH₂F | H | H | H | T2 | |
| 1552. | 3-Oxetanyl | CH₂CH₂F | H | H | Na | T2 | |
| 1553. | 3-Oxetanyl | CH₂CH₂F | H | H | H | T5 | |
| 1554. | 3-Oxetanyl | CH₂CH₂F | H | H | Na | T5 | |
| 1555. | 3-Oxetanyl | CH₂CH₂F | H | H | H | T6 | |
| 1556. | 3-Oxetanyl | CH₂CH₂F | H | H | Na | T6 | |
| 1557. | 3-Oxetanyl | CH₂CH₂F | H | H | H | T7 | |
| 1558. | 3-Oxetanyl | CH₂CH₂F | H | H | Na | T7 | |
| 1559. | Et | Allyl | Allyl | H | H | T1 | 146–148 |
| 1560. | Et | Allyl | Allyl | H | Na | T1 | 128–129 |
| 1561. | Et | Allyl | Allyl | H | H | T2 | 140–142 |
| 1562. | Et | Allyl | Allyl | H | Na | T2 | 112–115(D) |
| 1563. | Et | Allyl | Allyl | H | H | T5 | |
| 1564. | Et | Allyl | Allyl | H | Na | T5 | |
| 1565. | Et | Allyl | Allyl | H | H | T6 | 139–141 |
| 1566. | Et | Allyl | Allyl | H | Na | T6 | 132–135 |
| 1567. | Et | Allyl | Allyl | H | H | T7 | 114–116 |
| 1568. | Et | Allyl | Allyl | H | Na | T7 | 144–146 |
| 1569. | Pr | Allyl | Allyl | H | H | T1 | 111–113 |
| 1570. | Pr | Allyl | Allyl | H | Na | T1 | 143–145 |
| 1571. | Pr | Allyl | Allyl | H | H | T2 | |
| 1572. | Pr | Allyl | Allyl | H | Na | T2 | |
| 1573. | Pr | Allyl | Allyl | H | H | T5 | |
| 1574. | Pr | Allyl | Allyl | H | Na | T5 | |
| 1575. | Pr | Allyl | Allyl | H | H | T6 | |
| 1576. | Pr | Allyl | Allyl | H | Na | T6 | |
| 1577. | Pr | Allyl | Allyl | H | H | T7 | |
| 1578. | Pr | Allyl | Allyl | H | Na | T7 | |
| 1579. | i-Pr | Allyl | Allyl | H | H | T1 | 123–126 |
| 1580. | i-Pr | Allyl | Allyl | H | Na | T1 | |
| 1581. | i-Pr | Allyl | Allyl | H | H | T2 | |
| 1582. | i-Pr | Allyl | Allyl | H | Na | T2 | |
| 1583. | i-Pr | Allyl | Allyl | H | H | T5 | |
| 1584. | i-Pr | Allyl | Allyl | H | Na | T5 | |
| 1585. | i-Pr | Allyl | Allyl | H | H | T6 | |
| 1586. | i-Pr | Allyl | Allyl | H | Na | T6 | |
| 1587. | i-Pr | Allyl | Allyl | H | H | T7 | |
| 1588. | i-Pr | Allyl | Allyl | H | Na | T7 | |
| 1589. | c-Pr | Allyl | Allyl | H | H | T1 | |

TABLE 1-continued

Compounds of the formula (Ia)

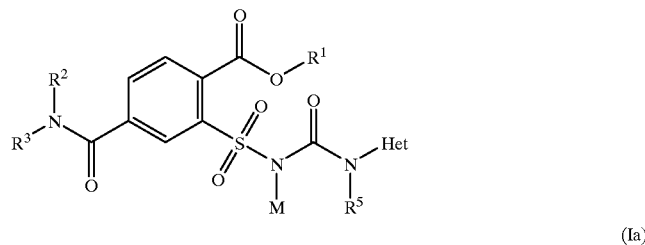

(Ia)

| Ex. | R¹ | R² | R³ | R⁵ | M | Het | m.p. |
|---|---|---|---|---|---|---|---|
| 1590. | c-Pr | Allyl | Allyl | H | Na | T1 | |
| 1591. | c-Pr | Allyl | Allyl | H | H | T2 | |
| 1592. | c-Pr | Allyl | Allyl | H | Na | T2 | |
| 1593. | c-Pr | Allyl | Allyl | H | H | T5 | |
| 1594. | c-Pr | Allyl | Allyl | H | Na | T5 | |
| 1595. | c-Pr | Allyl | Allyl | H | H | T6 | |
| 1596. | c-Pr | Allyl | Allyl | H | Na | T6 | |
| 1597. | c-Pr | Allyl | Allyl | H | H | T7 | |
| 1598. | c-Pr | Allyl | Allyl | H | Na | T7 | |
| 1599. | Bu | Allyl | Allyl | H | H | T1 | 105–106 |
| 1600. | Bu | Allyl | Allyl | H | Na | T1 | 119–123 |
| 1601. | Bu | Allyl | Allyl | H | H | T2 | |
| 1602. | Bu | Allyl | Allyl | H | Na | T2 | |
| 1603. | Bu | Allyl | Allyl | H | H | T5 | |
| 1604. | Bu | Allyl | Allyl | H | Na | T5 | |
| 1605. | Bu | Allyl | Allyl | H | H | T6 | |
| 1606. | Bu | Allyl | Allyl | H | Na | T6 | |
| 1607. | Bu | Allyl | Allyl | H | H | T7 | |
| 1608. | Bu | Allyl | Allyl | H | Na | T7 | |
| 1609. | $CH_2$-c-Pr | Allyl | Allyl | H | H | T1 | 120–122 |
| 1610. | $CH_2$-c-Pr | Allyl | Allyl | H | Na | T1 | |
| 1611. | $CH_2$-c-Pr | Allyl | Allyl | H | H | T2 | |
| 1612. | $CH_2$-c-Pr | Allyl | Allyl | H | Na | T2 | |
| 1613. | $CH_2$-c-Pr | Allyl | Allyl | H | H | T5 | |
| 1614. | $CH_2$-c-Pr | Allyl | Allyl | H | Na | T5 | |
| 1615. | $CH_2$-c-Pr | Allyl | Allyl | H | H | T6 | |
| 1616. | $CH_2$-c-Pr | Allyl | Allyl | H | Na | T6 | |
| 1617. | $CH_2$-c-Pr | Allyl | Allyl | H | H | T7 | |
| 1618. | $CH_2$-c-Pr | Allyl | Allyl | H | Na | T7 | |
| 1619. | $CH_2CH_2F$ | Allyl | Allyl | H | H | T1 | 134–136 |
| 1620. | $CH_2CH_2F$ | Allyl | Allyl | H | Na | T1 | 138–141 |
| 1621. | $CH_2CH_2F$ | Allyl | Allyl | H | H | T2 | |
| 1622. | $CH_2CH_2F$ | Allyl | Allyl | H | Na | T2 | |
| 1623. | $CH_2CH_2F$ | Allyl | Allyl | H | H | T5 | |
| 1624. | $CH_2CH_2F$ | Allyl | Allyl | H | Na | T5 | |
| 1625. | $CH_2CH_2F$ | Allyl | Allyl | H | H | T6 | |
| 1626. | $CH_2CH_2F$ | Allyl | Allyl | H | Na | T6 | |
| 1627. | $CH_2CH_2F$ | Allyl | Allyl | H | H | T7 | |
| 1628. | $CH_2CH_2F$ | Allyl | Allyl | H | Na | T7 | |
| 1629. | $CH_2CH_2CF_3$ | Allyl | Allyl | H | H | T1 | 101–103 |
| 1630. | $CH_2CH_2CF_3$ | Allyl | Allyl | H | Na | T1 | 143–146 |
| 1631. | $CH_2CH_2CF_3$ | Allyl | Allyl | H | H | T2 | |
| 1632. | $CH_2CH_2CF_3$ | Allyl | Allyl | H | Na | T2 | |
| 1633. | $CH_2CH_2CF_3$ | Allyl | Allyl | H | H | T5 | |
| 1634. | $CH_2CH_2CF_3$ | Allyl | Allyl | H | Na | T5 | |
| 1635. | $CH_2CH_2CF_3$ | Allyl | Allyl | H | H | T6 | |
| 1636. | $CH_2CH_2CF_3$ | Allyl | Allyl | H | Na | T6 | |
| 1637. | $CH_2CH_2CF_3$ | Allyl | Allyl | H | H | T7 | |
| 1638. | $CH_2CH_2CF_3$ | Allyl | Allyl | H | Na | T7 | |
| 1639. | 3-Oxetanyl | Allyl | Allyl | H | H | T1 | |
| 1640. | 3-Oxetanyl | Allyl | Allyl | H | Na | T1 | |
| 1641. | 3-Oxetanyl | Allyl | Allyl | H | H | T2 | |
| 1642. | 3-Oxetanyl | Allyl | Allyl | H | Na | T2 | |
| 1643. | 3-Oxetanyl | Allyl | Allyl | H | H | T5 | |
| 1644. | 3-Oxetanyl | Allyl | Allyl | H | Na | T5 | |
| 1645. | 3-Oxetanyl | Allyl | Allyl | H | H | T6 | |
| 1646. | 3-Oxetanyl | Allyl | Allyl | H | Na | T6 | |
| 1647. | 3-Oxetanyl | Allyl | Allyl | H | H | T7 | |
| 1648. | 3-Oxetanyl | Allyl | Allyl | H | Na | T7 | |
| 1649. | Et | Allyl | $CH_2CF_3$ | H | H | T1 | |
| 1650. | Et | Allyl | $CH_2CF_3$ | H | Na | T1 | |
| 1651. | Et | Allyl | $CH_2CF_3$ | H | H | T2 | |

TABLE 1-continued

Compounds of the formula (Ia)

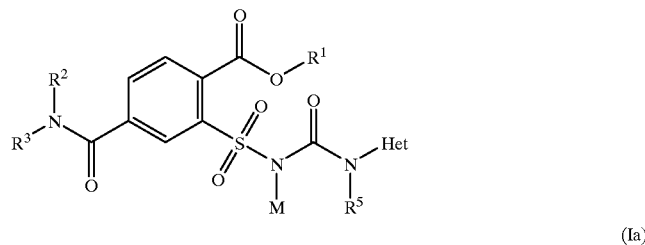

| Ex. | $R^1$ | $R^2$ | $R^3$ | $R^5$ | M | Het | m.p. |
|---|---|---|---|---|---|---|---|
| 1652. | Et | Allyl | $CH_2CF_3$ | H | Na | T2 | |
| 1653. | Et | Allyl | $CH_2CF_3$ | H | H | T5 | |
| 1654. | Et | Allyl | $CH_2CF_3$ | H | Na | T5 | |
| 1655. | Et | Allyl | $CH_2CF_3$ | H | H | T6 | |
| 1656. | Et | Allyl | $CH_2CF_3$ | H | Na | T6 | |
| 1657. | Et | Allyl | $CH_2CF_3$ | H | H | T7 | |
| 1658. | Et | Allyl | $CH_2CF_3$ | H | Na | T7 | |
| 1659. | Pr | Allyl | $CH_2CF_3$ | H | H | T1 | |
| 1660. | Pr | Allyl | $CH_2CF_3$ | H | Na | T1 | |
| 1661. | Pr | Allyl | $CH_2CF_3$ | H | H | T2 | |
| 1662. | Pr | Allyl | $CH_2CF_3$ | H | Na | T2 | |
| 1663. | Pr | Allyl | $CH_2CF_3$ | H | H | T5 | |
| 1664. | Pr | Allyl | $CH_2CF_3$ | H | Na | T5 | |
| 1665. | Pr | Allyl | $CH_2CF_3$ | H | H | T6 | |
| 1666. | Pr | Allyl | $CH_2CF_3$ | H | Na | T6 | |
| 1667. | Pr | Allyl | $CH_2CF_3$ | H | H | T7 | |
| 1668. | Pr | Allyl | $CH_2CF_3$ | H | Na | T7 | |
| 1669. | i-Pr | Allyl | $CH_2CF_3$ | H | H | T1 | |
| 1670. | i-Pr | Allyl | $CH_2CF_3$ | H | Na | T1 | |
| 1671. | i-Pr | Allyl | $CH_2CF_3$ | H | H | T2 | |
| 1672. | i-Pr | Allyl | $CH_2CF_3$ | H | Na | T2 | |
| 1673. | i-Pr | Allyl | $CH_2CF_3$ | H | H | T5 | |
| 1674. | i-Pr | Allyl | $CH_2CF_3$ | H | Na | T5 | |
| 1675. | i-Pr | Allyl | $CH_2CF_3$ | H | H | T6 | |
| 1676. | i-Pr | Allyl | $CH_2CF_3$ | H | Na | T6 | |
| 1677. | i-Pr | Allyl | $CH_2CF_3$ | H | H | T7 | |
| 1678. | i-Pr | Allyl | $CH_2CF_3$ | H | Na | T7 | |
| 1679. | c-Pr | Allyl | $CH_2CF_3$ | H | H | T1 | |
| 1680. | c-Pr | Allyl | $CH_2CF_3$ | H | Na | T1 | |
| 1681. | c-Pr | Allyl | $CH_2CF_3$ | H | H | T2 | |
| 1682. | c-Pr | Allyl | $CH_2CF_3$ | H | Na | T2 | |
| 1683. | c-Pr | Allyl | $CH_2CF_3$ | H | H | T5 | |
| 1684. | c-Pr | Allyl | $CH_2CF_3$ | H | Na | T5 | |
| 1685. | c-Pr | Allyl | $CH_2CF_3$ | H | H | T6 | |
| 1686. | c-Pr | Allyl | $CH_2CF_3$ | H | Na | T6 | |
| 1687. | c-Pr | Allyl | $CH_2CF_3$ | H | H | T7 | |
| 1688. | c-Pr | Allyl | $CH_2CF_3$ | H | Na | T7 | |
| 1689. | Bu | Allyl | $CH_2CF_3$ | H | H | T1 | |
| 1690. | Bu | Allyl | $CH_2CF_3$ | H | Na | T1 | |
| 1691. | Bu | Allyl | $CH_2CF_3$ | H | H | T2 | |
| 1692. | Bu | Allyl | $CH_2CF_3$ | H | Na | T2 | |
| 1693. | Bu | Allyl | $CH_2CF_3$ | H | H | T5 | |
| 1694. | Bu | Allyl | $CH_2CF_3$ | H | Na | T5 | |
| 1695. | Bu | Allyl | $CH_2CF_3$ | H | H | T6 | |
| 1696. | Bu | Allyl | $CH_2CF_3$ | H | Na | T6 | |
| 1697. | Bu | Allyl | $CH_2CF_3$ | H | H | T7 | |
| 1698. | Bu | Allyl | $CH_2CF_3$ | H | Na | T7 | |
| 1699. | $CH_2$-c-Pr | Allyl | $CH_2CF_3$ | H | H | T1 | |
| 1700. | $CH_2$-c-Pr | Allyl | $CH_2CF_3$ | H | Na | T1 | |
| 1701. | $CH_2$-c-Pr | Allyl | $CH_2CF_3$ | H | H | T2 | |
| 1702. | $CH_2$-c-Pr | Allyl | $CH_2CF_3$ | H | Na | T2 | |
| 1703. | $CH_2$-c-Pr | Allyl | $CH_2CF_3$ | H | H | T5 | |
| 1704. | $CH_2$-c-Pr | Allyl | $CH_2CF_3$ | H | Na | T5 | |
| 1705. | $CH_2$-c-Pr | Allyl | $CH_2CF_3$ | H | H | T6 | |
| 1706. | $CH_2$-c-Pr | Allyl | $CH_2CF_3$ | H | Na | T6 | |
| 1707. | $CH_2$-c-Pr | Allyl | $CH_2CF_3$ | H | H | T7 | |
| 1708. | $CH_2$-c-Pr | Allyl | $CH_2CF_3$ | H | Na | T7 | |
| 1709. | $CH_2CH_2F$ | Allyl | $CH_2CF_3$ | H | H | T1 | |
| 1710. | $CH_2CH_2F$ | Allyl | $CH_2CF_3$ | H | Na | T1 | |
| 1711. | $CH_2CH_2F$ | Allyl | $CH_2CF_3$ | H | H | T2 | |
| 1712. | $CH_2CH_2F$ | Allyl | $CH_2CF_3$ | H | Na | T2 | |
| 1713. | $CH_2CH_2F$ | Allyl | $CH_2CF_3$ | H | H | T5 | |

TABLE 1-continued

Compounds of the formula (Ia)

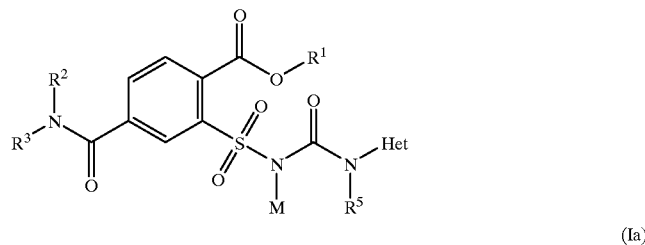

(Ia)

| Ex. | R¹ | R² | R³ | R⁵ | M | Het | m.p. |
|---|---|---|---|---|---|---|---|
| 1714. | CH₂CH₂F | Allyl | CH₂CF₃ | H | Na | T5 | |
| 1715. | CH₂CH₂F | Allyl | CH₂CF₃ | H | H | T6 | |
| 1716. | CH₂CH₂F | Allyl | CH₂CF₃ | H | Na | T6 | |
| 1717. | CH₂CH₂F | Allyl | CH₂CF₃ | H | H | T7 | |
| 1718. | CH₂CH₂F | Allyl | CH₂CF₃ | H | Na | T7 | |
| 1719. | CH₂CH₂CF₃ | Allyl | CH₂CF₃ | H | H | T1 | |
| 1720. | CH₂CH₂CF₃ | Allyl | CH₂CF₃ | H | Na | T1 | |
| 1721. | CH₂CH₂CF₃ | Allyl | CH₂CF₃ | H | H | T2 | |
| 1722. | CH₂CH₂CF₃ | Allyl | CH₂CF₃ | H | Na | T2 | |
| 1723. | CH₂CH₂CF₃ | Allyl | CH₂CF₃ | H | H | T5 | |
| 1724. | CH₂CH₂CF₃ | Allyl | CH₂CF₃ | H | Na | T5 | |
| 1725. | CH₂CH₂CF₃ | Allyl | CH₂CF₃ | H | H | T6 | |
| 1726. | CH₂CH₂CF₃ | Allyl | CH₂CF₃ | H | Na | T6 | |
| 1727. | CH₂CH₂CF₃ | Allyl | CH₂CF₃ | H | H | T7 | |
| 1728. | CH₂CH₂CF₃ | Allyl | CH₂CF₃ | H | Na | T7 | |
| 1729. | 3-Oxetanyl | Allyl | CH₂CF₃ | H | H | T1 | |
| 1730. | 3-Oxetanyl | Allyl | CH₂CF₃ | H | Na | T1 | |
| 1731. | 3-Oxetanyl | Allyl | CH₂CF₃ | H | H | T2 | |
| 1732. | 3-Oxetanyl | Allyl | CH₂CF₃ | H | Na | T2 | |
| 1733. | 3-Oxetanyl | Allyl | CH₂CF₃ | H | H | T5 | |
| 1734. | 3-Oxetanyl | Allyl | CH₂CF₃ | H | Na | T5 | |
| 1735. | 3-Oxetanyl | Allyl | CH₂CF₃ | H | H | T6 | |
| 1736. | 3-Oxetanyl | Allyl | CH₂CF₃ | H | Na | T6 | |
| 1737. | 3-Oxetanyl | Allyl | CH₂CF₃ | H | H | T7 | |
| 1738. | 3-Oxetanyl | Allyl | CH₂CF₃ | H | Na | T7 | |
| 1739. | Me | c-Pr | H | H | H | T1 | 170–173(D) |
| 1740. | Me | c-Pr | H | H | Na | T1 | 202–205(D) |
| 1741. | Me | c-Pr | H | H | H | T2 | |
| 1742. | Me | c-Pr | H | H | Na | T2 | |
| 1743. | Me | c-Pr | H | H | H | T5 | |
| 1744. | Me | c-Pr | H | H | Na | T5 | |
| 1745. | Me | c-Pr | H | H | H | T6 | |
| 1746. | Me | c-Pr | H | H | Na | T6 | |
| 1747. | Me | c-Pr | H | H | H | T7 | |
| 1748. | Me | c-Pr | H | H | Na | T7 | |
| 1749. | Me | CH₂c-Pr | H | H | H | T1 | 146–149(D) |
| 1750. | Me | CH₂c-Pr | H | H | Na | T1 | 203–205(D) |
| 1751. | Me | CH₂c-Pr | H | H | H | T2 | |
| 1752. | Me | CH₂c-Pr | H | H | Na | T2 | |
| 1753. | Me | CH₂c-Pr | H | H | H | T5 | |
| 1754. | Me | CH₂c-Pr | H | H | Na | T5 | |
| 1755. | Me | CH₂c-Pr | H | H | H | T6 | |
| 1756. | Me | CH₂c-Pr | H | H | Na | T6 | |
| 1757. | Me | CH₂c-Pr | H | H | H | T7 | |
| 1758. | Me | CH₂c-Pr | H | H | Na | T7 | |
| 1759. | Me | Bu | H | H | H | T1 | 122–125(D) |
| 1760. | Me | Bu | H | H | Na | T1 | 200–204(D) |
| 1761. | Me | Bu | H | H | H | T2 | |
| 1762. | Me | Bu | H | H | Na | T2 | |
| 1763. | Me | Bu | H | H | H | T5 | |
| 1764. | Me | Bu | H | H | Na | T5 | |
| 1765. | Me | Bu | H | H | H | T6 | |
| 1766. | Me | Bu | H | H | Na | T6 | |
| 1767. | Me | Bu | H | H | H | T7 | |
| 1768. | Me | Bu | H | H | Na | T7 | |
| 1769. | Me | CH₂CF₃ | H | H | H | T1 | |
| 1770. | Me | CH₂CF₃ | H | H | Na | T1 | |
| 1771. | Me | CH₂CF₃ | H | H | H | T2 | |
| 1772. | Me | CH₂CF₃ | H | H | Na | T2 | |
| 1773. | Me | CH₂CF₃ | H | H | H | T5 | |
| 1774. | Me | CH₂CF₃ | H | H | Na | T5 | |
| 1775. | Me | CH₂CF₃ | H | H | H | T6 | |

TABLE 1-continued

Compounds of the formula (Ia)

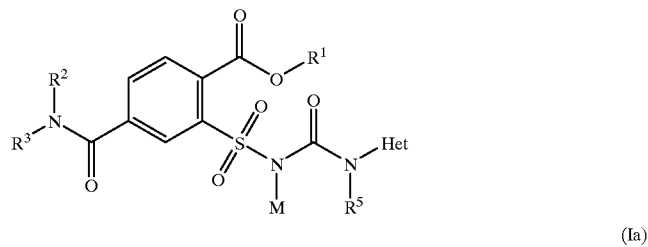

(Ia)

| Ex. | R$^1$ | R$^2$ | R$^3$ | R$^5$ | M | Het | m.p. |
|---|---|---|---|---|---|---|---|
| 1776. | Me | CH$_2$CF$_3$ | H | H | Na | T6 | |
| 1777. | Me | CH$_2$CF$_3$ | H | H | H | T7 | |
| 1778. | Me | CH$_2$CF$_3$ | H | H | Na | T7 | |
| 1779. | Me | Et | Me | H | H | T1 | 92–94(D) |
| 1780. | Me | Et | Me | H | Na | T1 | 115–117(D) |
| 1781. | Me | Et | Me | H | H | T2 | |
| 1782. | Me | Et | Me | H | Na | T2 | |
| 1783. | Me | Et | Me | H | H | T5 | |
| 1784. | Me | Et | Me | H | Na | T5 | |
| 1785. | Me | Et | Me | H | H | T6 | |
| 1786. | Me | Et | Me | H | Na | T6 | |
| 1787. | Me | Et | Me | H | H | T7 | |
| 1788. | Me | Et | Me | H | Na | T7 | |
| 1789. | Me | Et | Et | H | H | T1 | |
| 1790. | Me | Et | Et | H | Na | T1 | |
| 1791. | Me | Et | Et | H | H | T2 | |
| 1792. | Me | Et | Et | H | Na | T2 | |
| 1793. | Me | Et | Et | H | H | T5 | |
| 1794. | Me | Et | Et | H | Na | T5 | |
| 1795. | Me | Et | Et | H | H | T6 | |
| 1796. | Me | Et | Et | H | Na | T6 | |
| 1797. | Me | Et | Et | H | H | T7 | |
| 1798. | Me | Et | Et | H | Na | T7 | |
| 1799. | Me | Pr | Me | H | H | T1 | 174–176 |
| 1800. | Me | Pr | Me | H | Na | T1 | 148–150(D) |
| 1801. | Me | Pr | Me | H | H | T2 | |
| 1802. | Me | Pr | Me | H | Na | T2 | |
| 1803. | Me | Pr | Me | H | H | T5 | |
| 1804. | Me | Pr | Me | H | Na | T5 | |
| 1805. | Me | Pr | Me | H | H | T6 | |
| 1806. | Me | Pr | Me | H | Na | T6 | |
| 1807. | Me | Pr | Me | H | H | T7 | |
| 1808. | Me | Pr | Me | H | Na | T7 | |
| 1809. | Me | Pr | Pr | H | H | T1 | 137–139(D) |
| 1810. | Me | Pr | Pr | H | Na | T1 | 151–153(D) |
| 1811. | Me | Pr | Pr | H | H | T2 | |
| 1812. | Me | Pr | Pr | H | Na | T2 | |
| 1813. | Me | Pr | Pr | H | H | T5 | |
| 1814. | Me | Pr | Pr | H | Na | T5 | |
| 1815. | Me | Pr | Pr | H | H | T6 | |
| 1816. | Me | Pr | Pr | H | Na | T6 | |
| 1817. | Me | Pr | Pr | H | H | T7 | |
| 1818. | Me | Pr | Pr | H | Na | T7 | |
| 1819. | Me | Pr | CH$_2$CMe=CH$_2$ | H | H | T1 | 150–152(D) |
| 1820. | Me | Pr | CH$_2$CMe=CH$_2$ | H | Na | T1 | |
| 1821. | Me | Pr | CH$_2$CMe=CH$_2$ | H | H | T2 | |
| 1822. | Me | Pr | CH$_2$CMe=CH$_2$ | H | Na | T2 | |
| 1823. | Me | Pr | CH$_2$CMe=CH$_2$ | H | H | T5 | |
| 1824. | Me | Pr | CH$_2$CMe=CH$_2$ | H | Na | T5 | |
| 1825. | Me | Pr | CH$_2$CMe=CH$_2$ | H | H | T6 | |
| 1826. | Me | Pr | CH$_2$CMe=CH$_2$ | H | Na | T6 | |
| 1827. | Me | Pr | CH$_2$CMe=CH$_2$ | H | H | T7 | |
| 1828. | Me | Pr | CH$_2$CMe=CH$_2$ | H | Na | T7 | |
| 1829. | Me | Propargyl | Me | H | H | T1 | |
| 1830. | Me | Propargyl | Me | H | Na | T1 | |
| 1831. | Me | Propargyl | Me | H | H | T2 | |
| 1832. | Me | Propargyl | Me | H | Na | T2 | |
| 1833. | Me | Propargyl | Me | H | H | T5 | |
| 1834. | Me | Propargyl | Me | H | Na | T5 | |
| 1835. | Me | Propargyl | Me | H | H | T6 | |
| 1836. | Me | Propargyl | Me | H | Na | T6 | |
| 1837. | Me | Propargyl | Me | H | H | T7 | |

TABLE 1-continued

Compounds of the formula (Ia)

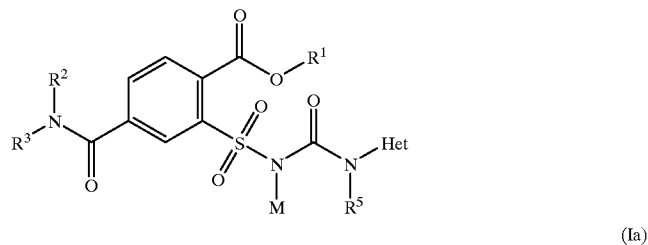

(Ia)

| Ex. | R¹ | R² | R³ | R⁵ | M | Het | m.p. |
|---|---|---|---|---|---|---|---|
| 1838. | Me | Propargyl | Me | H | Na | T7 | |
| 1839. | Me | Propargyl | Propargyl | H | H | T1 | 153–155(D) |
| 1840. | Me | Propargyl | Propargyl | H | Na | T1 | 145–147(D) |
| 1841. | Me | Propargyl | Propargyl | H | H | T2 | |
| 1842. | Me | Propargyl | Propargyl | H | Na | T2 | |
| 1843. | Me | Propargyl | Propargyl | H | H | T5 | |
| 1844. | Me | Propargyl | Propargyl | H | Na | T5 | |
| 1845. | Me | Propargyl | Propargyl | H | H | T6 | |
| 1846. | Me | Propargyl | Propargyl | H | Na | T6 | |
| 1847. | Me | Propargyl | Propargyl | H | H | T7 | |
| 1848. | Me | Propargyl | Propargyl | H | Na | T7 | |
| 1849. | Me | Allyl | $CH_2$-i-Pr | H | H | T1 | |
| 1850. | Me | Allyl | $CH_2$-i-Pr | H | Na | T1 | |
| 1851. | Me | Allyl | $CH_2$-i-Pr | H | H | T2 | |
| 1852. | Me | Allyl | $CH_2$-i-Pr | H | Na | T2 | |
| 1853. | Me | Allyl | $CH_2$-i-Pr | H | H | T5 | |
| 1854. | Me | Allyl | $CH_2$-i-Pr | H | Na | T5 | |
| 1855. | Me | Allyl | $CH_2$-i-Pr | H | H | T6 | |
| 1856. | Me | Allyl | $CH_2$-i-Pr | H | Na | T6 | |
| 1857. | Me | Allyl | $CH_2$-i-Pr | H | H | T7 | |
| 1858. | Me | Allyl | $CH_2$-i-Pr | H | Na | T7 | |
| 1859. | Me | Allyl | Propargyl | H | H | T1 | 157–159(D) |
| 1860. | Me | Allyl | Propargyl | H | Na | T1 | 146–148(D) |
| 1861. | Me | Allyl | Propargyl | H | H | T2 | |
| 1862. | Me | Allyl | Propargyl | H | Na | T2 | |
| 1863. | Me | Allyl | Propargyl | H | H | T5 | |
| 1864. | Me | Allyl | Propargyl | H | Na | T5 | |
| 1865. | Me | Allyl | Propargyl | H | H | T6 | |
| 1866. | Me | Allyl | Propargyl | H | Na | T6 | |
| 1867. | Me | Allyl | Propargyl | H | H | T7 | |
| 1868. | Me | Allyl | Propargyl | H | Na | T7 | |
| 1869. | Me | Allyl | $CH_2CH=CHCl$ | H | H | T1 | 145–147 |
| 1870. | Me | Allyl | $CH_2CH=CHCl$ | H | Na | T1 | 136–138(D) |
| 1871. | Me | Allyl | $CH_2CH=CHCl$ | H | H | T2 | |
| 1872. | Me | Allyl | $CH_2CH=CHCl$ | H | Na | T2 | |
| 1873. | Me | Allyl | $CH_2CH=CHCl$ | H | H | T5 | |
| 1874. | Me | Allyl | $CH_2CH=CHCl$ | H | Na | T5 | |
| 1875. | Me | Allyl | $CH_2CH=CHCl$ | H | H | T6 | |
| 1876. | Me | Allyl | $CH_2CH=CHCl$ | H | Na | T6 | |
| 1877. | Me | Allyl | $CH_2CH=CHCl$ | H | H | T7 | |
| 1878. | Me | Allyl | $CH_2CH=CHCl$ | H | Na | T7 | |
| 1879. | Me | Allyl | c-Pr | H | H | T1 | |
| 1880. | Me | Allyl | c-Pr | H | Na | T1 | |
| 1881. | Me | Allyl | c-Pr | H | H | T2 | |
| 1882. | Me | Allyl | c-Pr | H | Na | T2 | |
| 1883. | Me | Allyl | c-Pr | H | H | T5 | |
| 1884. | Me | Allyl | c-Pr | H | Na | T5 | |
| 1885. | Me | Allyl | c-Pr | H | H | T6 | |
| 1886. | Me | Allyl | c-Pr | H | Na | T6 | |
| 1887. | Me | Allyl | c-Pr | H | H | T7 | |
| 1888. | Me | Allyl | c-Pr | H | Na | T7 | |
| 1889. | Me | Allyl | c-Pr | H | H | T1 | |
| 1890. | Me | Allyl | c-Pr | H | Na | T1 | |
| 1891. | Me | Allyl | c-Pr | H | H | T2 | |
| 1892. | Me | Allyl | c-Pr | H | Na | T2 | |
| 1893. | Me | Allyl | c-Pr | H | H | T5 | |
| 1894. | Me | Allyl | c-Pr | H | Na | T5 | |
| 1895. | Me | Allyl | c-Pr | H | H | T6 | |
| 1896. | Me | Allyl | c-Pr | H | Na | T6 | |
| 1897. | Me | Allyl | c-Pr | H | H | T7 | |
| 1898. | Me | Allyl | c-Pr | H | Na | T7 | |
| 1899. | Me | Allyl | $CHMeCH_2CH_3$ | H | H | T1 | |

TABLE 1-continued

Compounds of the formula (Ia)

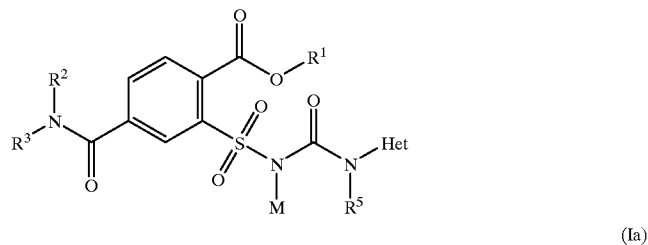

(Ia)

| Ex. | $R^1$ | $R^2$ | $R^3$ | $R^5$ | M | Het | m.p. |
|---|---|---|---|---|---|---|---|
| 1900. | Me | Allyl | CHMeCH$_2$CH$_3$ | H | Na | T1 | |
| 1901. | Me | Allyl | CHMeCH$_2$CH$_3$ | H | H | T2 | |
| 1902. | Me | Allyl | CHMeCH$_2$CH$_3$ | H | Na | T2 | |
| 1903. | Me | Allyl | CHMeCH$_2$CH$_3$ | H | H | T5 | |
| 1904. | Me | Allyl | CHMeCH$_2$CH$_3$ | H | Na | T5 | |
| 1905. | Me | Allyl | CHMeCH$_2$CH$_3$ | H | H | T6 | |
| 1906. | Me | Allyl | CHMeCH$_2$CH$_3$ | H | Na | T6 | |
| 1907. | Me | Allyl | CHMeCH$_2$CH$_3$ | H | H | T7 | |
| 1908. | Me | Allyl | CHMeCH$_2$CH$_3$ | H | Na | T7 | |
| 1909. | Me | Allyl | CH$_2$CHMe$_2$ | H | H | T1 | 123–125(D) |
| 1910. | Me | Allyl | CH$_2$CHMe$_2$ | H | Na | T1 | 118–120(D) |
| 1911. | Me | Allyl | CH$_2$CHMe$_2$ | H | H | T2 | |
| 1912. | Me | Allyl | CH$_2$CHMe$_2$ | H | Na | T2 | |
| 1913. | Me | Allyl | CH$_2$CHMe$_2$ | H | H | T5 | |
| 1914. | Me | Allyl | CH$_2$CHMe$_2$ | H | Na | T5 | |
| 1915. | Me | Allyl | CH$_2$CHMe$_2$ | H | H | T6 | |
| 1916. | Me | Allyl | CH$_2$CHMe$_2$ | H | Na | T6 | |
| 1917. | Me | Allyl | CH$_2$CHMe$_2$ | H | H | T7 | |
| 1918. | Me | Allyl | CH$_2$CHMe$_2$ | H | Na | T7 | |
| 1919. | Me | Allyl | CH$_2$CH$_2$F | H | H | T1 | |
| 1920. | Me | Allyl | CH$_2$CH$_2$F | H | Na | T1 | |
| 1921. | Me | Allyl | CH$_2$CH$_2$F | H | H | T2 | |
| 1922. | Me | Allyl | CH$_2$CH$_2$F | H | Na | T2 | |
| 1923. | Me | Allyl | CH$_2$CH$_2$F | H | H | T5 | |
| 1924. | Me | Allyl | CH$_2$CH$_2$F | H | Na | T5 | |
| 1925. | Me | Allyl | CH$_2$CH$_2$F | H | H | T6 | |
| 1926. | Me | Allyl | CH$_2$CH$_2$F | H | Na | T6 | |
| 1927. | Me | Allyl | CH$_2$CH$_2$F | H | H | T7 | |
| 1928. | Me | Allyl | CH$_2$CH$_2$F | H | Na | T7 | |
| 1929. | Me | Allyl | OMe | H | H | T1 | |
| 1930. | Me | Allyl | OMe | H | Na | T1 | |
| 1931. | Me | Allyl | OMe | H | H | T2 | |
| 1932. | Me | Allyl | OMe | H | Na | T2 | |
| 1933. | Me | Allyl | OMe | H | H | T5 | |
| 1934. | Me | Allyl | OMe | H | Na | T5 | |
| 1935. | Me | Allyl | OMe | H | H | T6 | |
| 1936. | Me | Allyl | OMe | H | Na | T6 | |
| 1937. | Me | Allyl | OMe | H | H | T7 | |
| 1938. | Me | Allyl | OMe | H | Na | T7 | |
| 1939. | Me | Allyl | OEt | H | H | T1 | |
| 1940. | Me | Allyl | OEt | H | Na | T1 | |
| 1941. | Me | Allyl | OEt | H | H | T2 | |
| 1942. | Me | Allyl | OEt | H | Na | T2 | |
| 1943. | Me | Allyl | OEt | H | H | T5 | |
| 1944. | Me | Allyl | OEt | H | Na | T5 | |
| 1945. | Me | Allyl | OEt | H | H | T6 | |
| 1946. | Me | Allyl | OEt | H | Na | T6 | |
| 1947. | Me | Allyl | OEt | H | H | T7 | |
| 1948. | Me | Allyl | OEt | H | Na | T7 | |
| 1949. | Me | Allyl | OPr | H | H | T1 | |
| 1950. | Me | Allyl | OPr | H | Na | T1 | |
| 1951. | Me | Allyl | OPr | H | H | T2 | |
| 1952. | Me | Allyl | OPr | H | Na | T2 | |
| 1953. | Me | Allyl | OPr | H | H | T5 | |
| 1954. | Me | Allyl | OPr | H | Na | T5 | |
| 1955. | Me | Allyl | OPr | H | H | T6 | |
| 1956. | Me | Allyl | OPr | H | Na | T6 | |
| 1957. | Me | Allyl | OPr | H | H | T7 | |
| 1958. | Me | Allyl | OPr | H | Na | T7 | |
| 1959. | Me | Allyl | OAllyl | H | H | T1 | |
| 1960. | Me | Allyl | OAllyl | H | Na | T1 | |
| 1961. | Me | Allyl | OAllyl | H | H | T2 | |

TABLE 1-continued

Compounds of the formula (Ia)

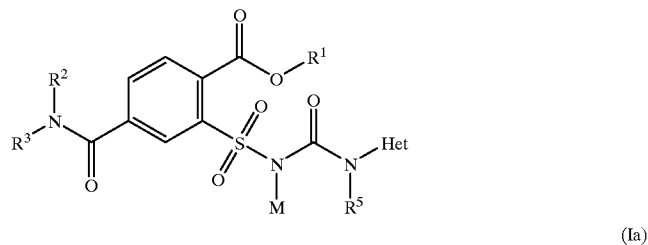

(Ia)

| Ex. | R$^1$ | R$^2$ | R$^3$ | R$^5$ | M | Het | m.p. |
|---|---|---|---|---|---|---|---|
| 1962. | Me | Allyl | OAllyl | H | Na | T2 | |
| 1963. | Me | Allyl | OAllyl | H | H | T5 | |
| 1964. | Me | Allyl | OAllyl | H | Na | T5 | |
| 1965. | Me | Allyl | OAllyl | H | H | T6 | |
| 1966. | Me | Allyl | OAllyl | H | Na | T6 | |
| 1967. | Me | Allyl | OAllyl | H | H | T7 | |
| 1968. | Me | Allyl | OAllyl | H | Na | T7 | |
| 1969. | Me | Allyl | NMe$_2$ | H | H | T1 | |
| 1970. | Me | Allyl | NMe$_2$ | H | Na | T1 | |
| 1971. | Me | Allyl | NMe$_2$ | H | H | T2 | |
| 1972. | Me | Allyl | NMe$_2$ | H | Na | T2 | |
| 1973. | Me | Allyl | NMe$_2$ | H | H | T5 | |
| 1974. | Me | Allyl | NMe$_2$ | H | Na | T5 | |
| 1975. | Me | Allyl | NMe$_2$ | H | H | T6 | |
| 1976. | Me | Allyl | NMe$_2$ | H | Na | T6 | |
| 1977. | Me | Allyl | NMe$_2$ | H | H | T7 | |
| 1978. | Me | Allyl | NMe$_2$ | H | Na | T7 | |
| 1979. | Me | Allyl | MeSO$_2$ | H | H | T1 | |
| 1980. | Me | Allyl | MeSO$_2$ | H | Na | T1 | |
| 1981. | Me | Allyl | MeSO$_2$ | H | H | T2 | |
| 1982. | Me | Allyl | MeSO$_2$ | H | Na | T2 | |
| 1983. | Me | Allyl | MeSO$_2$ | H | H | T5 | |
| 1984. | Me | Allyl | MeSO$_2$ | H | Na | T5 | |
| 1985. | Me | Allyl | MeSO$_2$ | H | H | T6 | |
| 1986. | Me | Allyl | MeSO$_2$ | H | Na | T6 | |
| 1987. | Me | Allyl | MeSO$_2$ | H | H | T7 | |
| 1988. | Me | Allyl | MeSO$_2$ | H | Na | T7 | |
| 1989. | Me | Allyl | Cyclopentyl | H | H | T1 | 187–189(D) |
| 1990. | Me | Allyl | Cyclopentyl | H | Na | T1 | 135–137(D) |
| 1991. | Me | Allyl | Cyclopentyl | H | H | T2 | |
| 1992. | Me | Allyl | Cyclopentyl | H | Na | T2 | |
| 1993. | Me | Allyl | Cyclopentyl | H | H | T5 | |
| 1994. | Me | Allyl | Cyclopentyl | H | Na | T5 | |
| 1995. | Me | Allyl | Cyclopentyl | H | H | T6 | |
| 1996. | Me | Allyl | Cyclopentyl | H | Na | T6 | |
| 1997. | Me | Allyl | Cyclopentyl | H | H | T7 | |
| 1998. | Me | Allyl | Cyclopentyl | H | Na | T7 | |
| 1999. | Me | Hexyl | H | H | H | T1 | |
| 2000. | Me | Hexyl | H | H | Na | T1 | |
| 2001. | Me | Hexyl | H | H | H | T2 | |
| 2002. | Me | Hexyl | H | H | Na | T2 | |
| 2003. | Me | MeOCH$_2$CH$_2$ | H | H | H | T1 | 138–141(D) |
| 2004. | Me | MeOCH$_2$CH$_2$ | H | H | Na | T1 | 196–199(D) |
| 2005. | Me | MeOCH$_2$CH$_2$ | H | H | H | T2 | |
| 2006. | Me | MeOCH$_2$CH$_2$ | H | H | Na | T2 | |
| 2007. | Me | MeSCH$_2$CH$_2$ | H | H | H | T1 | |
| 2008. | Me | MeSCH$_2$CH$_2$ | H | H | Na | T1 | |
| 2009. | Me | MeSCH$_2$CH$_2$ | H | H | H | T2 | |
| 2010. | Me | MeSCH$_2$CH$_2$ | H | H | Na | T2 | |
| 2011. | Me | MeSCH$_2$CH$_2$ | H | H | H | T1 | |
| 2012. | Me | MeSCH$_2$CH$_2$ | H | H | Na | T1 | |
| 2013. | Me | MeSCH$_2$CH$_2$ | H | H | H | T2 | |
| 2014. | Me | MeSCH$_2$CH$_2$ | H | H | Na | T2 | |
| 2011. | Me | MeSO$_2$CH$_2$CH$_2$ | H | H | H | T1 | |
| 2012. | Me | MeSO$_2$CH$_2$CH$_2$ | H | H | Na | T1 | |
| 2013. | Me | MeSO$_2$CH$_2$CH$_2$ | H | H | H | T2 | |
| 2014. | Me | MeSO$_2$CH$_2$CH$_2$ | H | H | Na | T2 | |
| 2015. | Me | HOCH$_2$CH$_2$ | H | H | H | T1 | |
| 2016. | Me | HOCH$_2$CH$_2$ | H | H | Na | T1 | |
| 2017. | Me | HOCH$_2$CH$_2$ | H | H | H | T2 | |
| 2018. | Me | HOCH$_2$CH$_2$ | H | H | Na | T2 | |
| 2019. | Me | Me$_2$NCH$_2$CH$_2$ | H | H | H | T1 | |

TABLE 1-continued

Compounds of the formula (Ia)

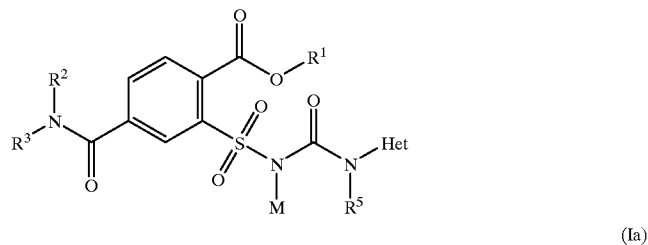

(Ia)

| Ex. | R¹ | R² | R³ | R⁵ | M | Het | m.p. |
|---|---|---|---|---|---|---|---|
| 2020. | Me | Me₂NCH₂CH₂ | H | H | Na | T1 | |
| 2021. | Me | Me₂NCH₂CH₂ | H | H | H | T2 | |
| 2022. | Me | Me₂NCH₂CH₂ | H | H | Na | T2 | |
| 2023. | Me | ClCH₂CH₂ | H | H | H | T1 | |
| 2024. | Me | ClCH₂CH₂ | H | H | Na | T1 | |
| 2025. | Me | ClCH₂CH₂ | H | H | H | T2 | |
| 2026. | Me | ClCH₂CH₂ | H | H | Na | T2 | |
| 2027. | Me | MeO₂CCH₂ | H | H | H | T1 | |
| 2028. | Me | MeO₂CCH₂ | H | H | Na | T1 | |
| 2029. | Me | MeO₂CCH₂ | H | H | H | T2 | |
| 2030. | Me | MeO₂CCH₂ | H | H | Na | T2 | |
| 2031. | Me | MeO₂CCH(Me) | H | H | H | T1 | 94–96(D) |
| 2032. | Me | MeO₂CCH(Me) | H | H | Na | T1 | |
| 2033. | Me | MeO₂CCH(Me) | H | H | H | T2 | |
| 2034. | Me | MeO₂CCH(Me) | H | H | Na | T2 | |
| 2035. | Me | 2-Hexen-1-yl | H | H | H | T1 | |
| 2036. | Me | 2-Hexen-1-yl | H | H | Na | T1 | |
| 2037. | Me | 2-Hexen-1-yl | H | H | H | T2 | |
| 2038. | Me | 2-Hexen-1-yl | H | H | Na | T2 | |
| 2039. | Me | 2-Hexyn-1-yl | H | H | H | T1 | |
| 2040. | Me | 2-Hexyn-1-yl | H | H | Na | T1 | |
| 2041. | Me | 2-Hexyn-1-yl | H | H | H | T2 | |
| 2042. | Me | 2-Hexyn-1-yl | H | H | Na | T2 | |
| 2043. | Me | Ph | H | H | H | T1 | 190–192(D) |
| 2044. | Me | Ph | H | H | Na | T1 | >260 |
| 2045. | Me | Ph | H | H | H | T2 | |
| 2046. | Me | Ph | H | H | Na | T2 | |
| 2047. | Me | 4-MePh | H | H | H | T1 | |
| 2048. | Me | 4-MePh | H | H | Na | T1 | |
| 2049. | Me | 4-MePh | H | H | H | T2 | |
| 2050. | Me | 4-MePh | H | H | Na | T2 | |
| 2051. | Me | 3-CF₂Ph | H | H | H | T1 | |
| 2052. | Me | 3-CF₂Ph | H | H | Na | T1 | |
| 2053. | Me | 3-CF₂Ph | H | H | H | T2 | |
| 2054. | Me | 3-CF₂Ph | H | H | Na | T2 | |
| 2055. | Me | 2-ClPh | H | H | H | T1 | |
| 2056. | Me | 2-ClPh | H | H | Na | T1 | |
| 2057. | Me | 2-ClPh | H | H | H | T2 | |
| 2058. | Me | 2-ClPh | H | H | Na | T2 | |
| 2059. | Me | 4-MeOPh | H | H | H | T1 | |
| 2060. | Me | 4-MeOPh | H | H | Na | T1 | |
| 2061. | Me | 4-MeOPh | H | H | H | T2 | |
| 2062. | Me | 4-MeOPh | H | H | Na | T2 | |
| 2063. | Me | PhCH₂ | H | H | H | T1 | 148–149(D) |
| 2064. | Me | PhCH₂ | H | H | Na | T1 | 221–224(D) |
| 2065. | Me | PhCH₂ | H | H | H | T2 | |
| 2066. | Me | PhCH₂ | H | H | Na | T2 | |
| 2067. | Me | CH₂=CClCH₂ | H | H | H | T1 | |
| 2068. | Me | CH₂=CClCH₂ | H | H | Na | T1 | |
| 2069. | Me | CH₂=CClCH₂ | H | H | H | T2 | |
| 2070. | Me | CH₂=CClCH₂ | H | H | Na | T2 | |
| 2071. | Me | 2-Cyclopenten-1-yl | H | H | H | T1 | |
| 2072. | Me | 2-Cyclopenten-1-yl | H | H | Na | T1 | |
| 2073. | Me | 2-Cyclopenten-1-yl | H | H | H | T2 | |
| 2074. | Me | 2-Cyclopenten-1-yl | H | H | Na | T2 | |
| 2075. | Me | Cyclohexyl | H | H | H | T1 | 189–192(D) |
| 2076. | Me | Cyclohexyl | H | H | Na | T1 | 202–206(D) |
| 2077. | Me | Cyclohexyl | H | H | H | T2 | |
| 2078. | Me | Cyclohexyl | H | H | Na | T2 | |
| 2079. | Me | CyclohexylCH₂ | H | H | H | T1 | |
| 2080. | Me | CyclohexylCH₂ | H | H | Na | T1 | |
| 2081. | Me | CyclohexylCH₂ | H | H | H | T2 | |

TABLE 1-continued

Compounds of the formula (Ia)

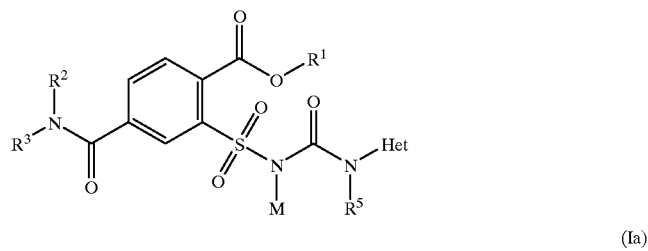

(Ia)

| Ex. | R¹ | R² | R³ | R⁵ | M | Het | m.p. |
|---|---|---|---|---|---|---|---|
| 2082. | Me | CyclohexylCH₂ | H | H | Na | T2 | |
| 2083. | Me | CH₂=CClCH₂ | H | H | H | T1 | |
| 2084. | Me | CH₂=CClCH₂ | H | H | Na | T1 | |
| 2085. | Me | CH₂=CClCH₂ | H | H | H | T2 | |
| 2086. | Me | CH₂=CClCH₂ | H | H | Na | T2 | |
| 2087. | Me | MeSO₂ | H | H | H | T1 | 142–145(D) |
| 2088. | Me | MeSO₂ | H | H | Na | T1 | 194–196(D) |
| 2089. | Me | MeSO₂ | H | H | H | T2 | |
| 2090. | Me | MeSO₂ | H | H | Na | T2 | |
| 2091. | Me | NCCH₂ | H | H | H | T1 | |
| 2092. | Me | NCCH₂ | H | H | Na | T1 | |
| 2093. | Me | NCCH₂ | H | H | H | T2 | |
| 2094. | Me | NCCH₂ | H | H | Na | T2 | |
| 2095. | Me | MeO | H | H | H | T1 | 127–130(D) |
| 2096. | Me | MeO | H | H | Na | T1 | |
| 2097. | Me | MeO | H | H | H | T2 | |
| 2098. | Me | MeO | H | H | Na | T2 | |
| 2099. | Me | AllylO | H | H | H | T1 | |
| 2100. | Me | AllylO | H | H | Na | T1 | |
| 2101. | Me | AllylO | H | H | H | T2 | |
| 2102. | Me | AllylO | H | H | Na | T2 | |
| 2103. | Me | MeO | Me | H | H | T1 | 180–184(D) |
| 2104. | Me | MeO | Me | H | Na | T1 | |
| 2105. | Me | MeO | Me | H | H | T2 | |
| 2106. | Me | MeO | Me | H | Na | T2 | |
| 2107. | Me | MeO | Allyl | H | H | T1 | |
| 2108. | Me | MeO | Allyl | H | Na | T1 | |
| 2109. | Me | MeO | Allyl | H | H | T2 | |
| 2110. | Me | MeO | Allyl | H | Na | T2 | |
| 2111. | Me | AllylNH | H | H | H | T1 | |
| 2112. | Me | AllylNH | H | H | Na | T1 | |
| 2113. | Me | AllylNH | H | H | H | T2 | |
| 2114. | Me | AllylNH | H | H | Na | T2 | |
| 2115. | Me | Me₂N | H | H | H | T1 | 178–180(D) |
| 2116. | Me | Me₂N | H | H | Na | T1 | |
| 2117. | Me | Me₂N | H | H | H | T2 | |
| 2118. | Me | Me₂N | H | H | Na | T2 | |
| 2119. | Me | Piperidino | H | H | H | T1 | 142–144(D) |
| 2120. | Me | Piperidino | H | H | Na | T1 | 187–189(D) |
| 2121. | Me | Piperidino | H | H | H | T2 | |
| 2122. | Me | Piperidino | H | H | Na | T2 | |
| 2123. | Me | EtO₂CNH | H | H | H | T1 | 155–157(D) |
| 2124. | Me | EtO₂CNH | H | H | Na | T1 | |
| 2125. | Me | EtO₂CNH | H | H | H | T2 | |
| 2126. | Me | EtO₂CNH | H | H | Na | T2 | |
| 2127. | Me | HOCH₂CH₂ | HOCH₂CH₂ | H | H | T1 | |
| 2128. | Me | HOCH₂CH₂ | HOCH₂CH₂ | H | Na | T1 | |
| 2129. | Me | HOCH₂CH₂ | HOCH₂CH₂ | H | H | T2 | |
| 2130. | Me | HOCH₂CH₂ | HOCH₂CH₂ | H | Na | T2 | |
| 2131. | Me | 3-Pyridyl | H | H | H | T1 | 101–103(D) |
| 2132. | Me | 3-Pyridyl | H | H | Na | T1 | 138–140(D) |
| 2133. | Me | 3-Pyridyl | H | H | H | T2 | |
| 2134. | Me | 3-Pyridyl | H | H | Na | T2 | |
| 2135. | Me | 2-Thiazolyl | H | H | H | T1 | 204–207(D) |
| 2136. | Me | 2-Thiazolyl | H | H | Na | T1 | 194–197(D) |
| 2137. | Me | 2-Thiazolyl | H | H | H | T2 | |
| 2138. | Me | 2-Thiazolyl | H | H | Na | T2 | |

TABLE 1-continued

Compounds of the formula (Ia)

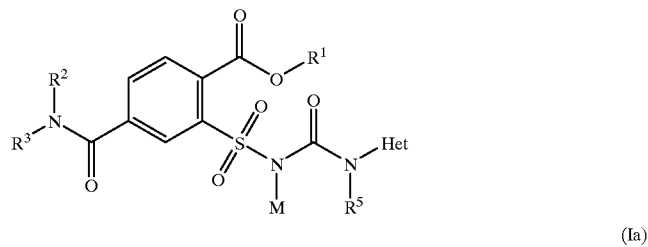

(Ia)

| Ex. | R¹ | R² | R³ | R⁵ | M | Het | m.p. |
|---|---|---|---|---|---|---|---|
| 2139. | Me | | H₃C-CH₂-CH / H₃C-CH₂ (pyrrolidinyl-like with 2 Me) | H | H | T1 | 134–139(D) |
| 2140. | Me | 2-Thiazolyl | | H | Na | T1 | 233–235(D) |
| 2141. | Me | 2-Thiazolyl | | H | H | T2 | |
| 2142. | Me | 2-Thiazolyl | | H | Na | T2 | |
| 2143. | Me | | cyclohexyl (H₂C-CH₂ / H₂C \ / H₂C-CH₂) | H | H | T1 | 209–211(D) |
| 2144. | Me | 2-Thiazolyl | | H | Na | T1 | |
| 2145. | Me | 2-Thiazolyl | | H | H | T2 | |
| 2146. | Me | 2-Thiazolyl | | H | Na | T2 | |
| 2147. | Me | | HC-CH₂ / HC=... \ / HC-CH₂ | H | H | T1 | |
| 2148. | Me | 2-Thiazolyl | | H | Na | T1 | |
| 2149. | Me | 2-Thiazolyl | | H | H | T2 | |
| 2150. | Me | 2-Thiazolyl | | H | Na | T2 | |
| 2151. | Me | | HC=CH-CH₂ / HC \ / H₃C-CH₂ | H | H | T1 | |
| 2152. | Me | 2-Thiazolyl | | H | Na | T1 | |
| 2153. | Me | 2-Thiazolyl | | H | H | T2 | |
| 2154. | Me | 2-Thiazolyl | | H | Na | T2 | |
| 2155. | Me | | N=CH / \ HC=C-H (pyrazole/imidazole-like) | H | H | T1 | |
| 2156. | Me | 2-Thiazolyl | | H | Na | T1 | |
| 2157. | Me | 2-Thiazolyl | | H | H | T2 | |
| 2158. | Me | 2-Thiazolyl | | H | Na | T2 | |
| 2159. | Me | | S-CH₂ / \ H₃C-CH₂ | H | H | T1 | |
| 2160. | Me | 2-Thiazolyl | | H | Na | T1 | |
| 2161. | Me | 2-Thiazolyl | | H | H | T2 | |
| 2162. | Me | 2-Thiazolyl | | H | Na | T2 | |

TABLE 1-continued

Compounds of the formula (Ia)

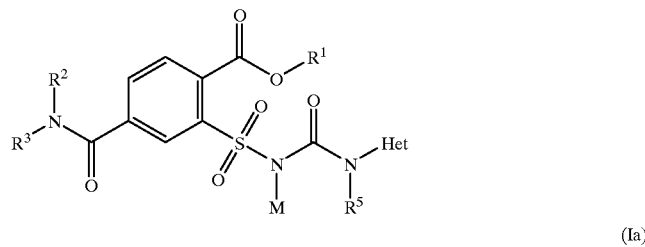

(Ia)

| Ex. | R¹ | R² | R³ | R⁵ | M | Het | m.p. |
|---|---|---|---|---|---|---|---|
| 2163. | Me | | $H_3C\underset{CH_2}{\overset{O}{\underset{|}{\diagup}}}\overset{O}{\diagdown}$ | H | H | T1 | |
| 2164. | Me | 2-Thiazolyl | | H | Na | T1 | |
| 2165. | Me | 2-Thiazolyl | | H | H | T2 | |
| 2166. | Me | 2-Thiazolyl | | H | Na | T2 | |
| 2167. | Me | Allyl | c-Hexyl | H | H | T1 | 147–149(D) |
| 2168. | Me | Allyl | c-Hexyl | H | Na | T1 | 162–164(D) |
| 2169. | Me | Allyl | c-Hexyl | H | H | T2 | |
| 2170. | Me | Allyl | c-Hexyl | H | Na | T2 | |
| 2171. | Me | Allyl | CH₂CH=CHMe | H | H | T1 | 142–145(D) |
| 2172. | Me | Allyl | CH₂CH=CHMe | H | Na | T1 | 129–131(D) |
| 2173. | Me | Allyl | CH₂CH=CHMe | H | H | T2 | |
| 2174. | Me | Allyl | CH₂CH=CHMe | H | Na | T2 | |
| 2175. | Me | Allyl | CH₂CCl=CH₂ | H | H | T1 | 163–165(D) |
| 2176. | Me | Allyl | CH₂CCl=CH₂ | H | Na | T1 | 133–135(D) |
| 2177. | Me | Allyl | CH₂CCl=CH₂ | H | H | T2 | |
| 2178. | Me | Allyl | CH₂CCl=CH₂ | H | Na | T2 | |
| 2179. | Me | Allyl | CH₂CBr=CH₂ | H | H | T1 | 166–168 |
| 2180. | Me | Allyl | CH₂CBr=CH₂ | H | Na | T1 | 136–139 |
| 2181. | Me | Allyl | CH₂CBr=CH₂ | H | H | T2 | |
| 2182. | Me | Allyl | CH₂CBr=CH₂ | H | Na | T2 | |
| 2183. | Me | Allyl | CH₂CMe=CH₂ | H | H | T1 | 160–162(D) |
| 2184. | Me | Allyl | CH₂CMe=CH₂ | H | Na | T1 | 141–143(D) |
| 2185. | Me | Allyl | CH₂CMe=CH₂ | H | H | T2 | |
| 2186. | Me | Allyl | CH₂CMe=CH₂ | H | Na | T2 | |
| 2187. | Me | Et | CH₂CMe=CH₂ | H | H | T1 | 158–160(D) |
| 2188. | Me | Et | CH₂CMe=CH₂ | H | Na | T1 | 149–151(D) |
| 2189. | Me | Et | CH₂CMe=CH₂ | H | H | T2 | |
| 2190. | Me | Et | CH₂CMe=CH₂ | H | Na | T2 | |
| 2191. | Me | Pr | CH₂CMe=CH₂ | H | H | T1 | |
| 2192. | Me | Pr | CH₂CMe=CH₂ | H | Na | T1 | 148–150(D) |
| 2193. | Me | Pr | CH₂CMe=CH₂ | H | H | T2 | |
| 2194. | Me | Pr | CH₂CMe=CH₂ | H | Na | T2 | |
| 2195. | Me | Allyl | $-N{\overset{CH_2}{\underset{CH_2}{\diagdown}}}$ | H | H | T1 | |
| 2196. | Me | Allyl | CH₂CMe=CH₂ | H | Na | T1 | |
| 2197. | Me | Allyl | CH₂CMe=CH₂ | H | H | T2 | |
| 2198. | Me | Allyl | CH₂CMe=CH₂ | H | Na | T2 | |
| 2199. | Allyl | H | H | H | H | T1 | 116–118 |
| 2200. | Allyl | H | H | H | Na | T1 | 202–205 |
| 2201. | Allyl | H | H | H | H | T2 | |
| 2202. | Allyl | H | H | H | Na | T2 | |
| 2203. | Allyl | Me | H | H | H | T1 | |
| 2204. | Allyl | Me | H | H | Na | T1 | |
| 2205. | Allyl | Me | H | H | H | T2 | |
| 2206. | Allyl | Me | H | H | Na | T2 | |
| 2207. | Allyl | Et | H | H | H | T1 | |
| 2208. | Allyl | Et | H | H | Na | T1 | |
| 2209. | Allyl | Et | H | H | H | T2 | |
| 2210. | Allyl | Et | H | H | Na | T2 | |
| 2211. | Allyl | i-Pr | H | H | H | T1 | |
| 2212. | Allyl | i-Pr | H | H | Na | T1 | |
| 2213. | Allyl | i-Pr | H | H | H | T2 | |

TABLE 1-continued

Compounds of the formula (Ia)

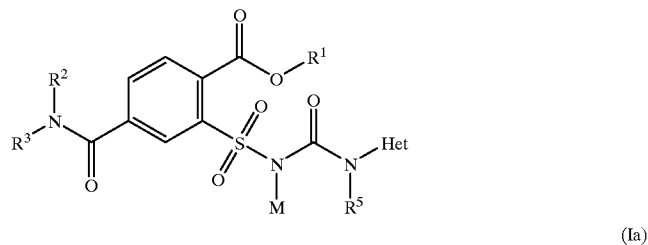

(Ia)

| Ex. | R¹ | R² | R³ | R⁵ | M | Het | m.p. |
|---|---|---|---|---|---|---|---|
| 2214. | Allyl | i-Pr | H | H | Na | T2 | |
| 2215. | Allyl | Allyl | H | H | H | T1 | |
| 2216. | Allyl | Allyl | H | H | Na | T1 | |
| 2217. | Allyl | Allyl | H | H | H | T2 | |
| 2218. | Allyl | Allyl | H | H | Na | T2 | |
| 2219. | Allyl | Allyl | Allyl | H | H | T1 | 104–107 |
| 2220. | Allyl | Allyl | Allyl | H | Na | T1 | |
| 2221. | Allyl | Allyl | Allyl | H | H | T2 | |
| 2222. | Allyl | Allyl | Allyl | H | Na | T2 | |
| 2223. | Allyl | Me | Me | H | H | T1 | |
| 2224. | Allyl | Me | Me | H | Na | T1 | |
| 2225. | Allyl | Me | Me | H | H | T2 | |
| 2226. | Allyl | Me | Me | H | Na | T2 | |
| 2227. | Propargyl | H | H | H | H | T1 | 185–188 |
| 2228. | Propargyl | H | H | H | Na | T1 | 190–193 |
| 2229. | Propargyl | H | H | H | H | T2 | |
| 2230. | Propargyl | H | H | H | Na | T2 | |
| 2231. | Propargyl | Me | H | H | H | T1 | |
| 2232. | Propargyl | Me | H | H | Na | T1 | |
| 2233. | Propargyl | Me | H | H | H | T2 | |
| 2234. | Propargyl | Me | H | H | Na | T2 | |
| 2235. | Propargyl | Et | H | H | H | T1 | |
| 2236. | Propargyl | Et | H | H | Na | T1 | |
| 2237. | Propargyl | Et | H | H | H | T2 | |
| 2238. | Propargyl | Et | H | H | Na | T2 | |
| 2239. | Propargyl | i-Pr | H | H | H | T1 | |
| 2240. | Propargyl | i-Pr | H | H | Na | T1 | |
| 2241. | Propargyl | i-Pr | H | H | H | T2 | |
| 2242. | Propargyl | i-Pr | H | H | Na | T2 | |
| 2243. | Propargyl | Allyl | H | H | H | T1 | |
| 2244. | Propargyl | Allyl | H | H | Na | T1 | |
| 2245. | Propargyl | Allyl | H | H | H | T2 | |
| 2246. | Propargyl | Allyl | H | H | Na | T2 | |
| 2247. | Propargyl | Allyl | Allyl | H | H | T1 | 126–128 |
| 2248. | Propargyl | Allyl | Allyl | H | Na | T1 | |
| 2249. | Propargyl | Allyl | Allyl | H | H | T2 | |
| 2250. | Propargyl | Allyl | Allyl | H | Na | T2 | |
| 2251. | Propargyl | Me | Me | H | H | T1 | 147–149 |
| 2252. | Propargyl | Me | Me | H | Na | T1 | |
| 2253. | Propargyl | Me | Me | H | HNEt₃ | T1 | 119–122 |
| 2254. | Propargyl | Me | Me | H | Na | T2 | |
| 2255. | Propargyl | Me | Me | H | H | T2 | |
| 2256. | MeOCH₂CH₂ | H | H | H | H | T1 | 134–137 |
| 2257. | MeOCH₂CH₂ | H | H | H | Na | T1 | |
| 2258. | MeOCH₂CH₂ | H | H | H | H | T2 | |
| 2259. | MeOCH₂CH₂ | H | H | H | Na | T2 | |
| 2260. | MeOCH₂CH₂ | Me | H | H | H | T1 | |
| 2261. | MeOCH₂CH₂ | Me | H | H | Na | T1 | |
| 2262. | MeOCH₂CH₂ | Me | H | H | H | T2 | |
| 2263. | MeOCH₂CH₂ | Me | H | H | Na | T2 | |
| 2264. | MeOCH₂CH₂ | Et | H | H | H | T1 | |
| 2265. | MeOCH₂CH₂ | Et | H | H | Na | T1 | |
| 2266. | MeOCH₂CH₂ | Et | H | H | H | T2 | |
| 2267. | MeOCH₂CH₂ | Et | H | H | Na | T2 | |
| 2268. | MeOCH₂CH₂ | i-Pr | H | H | H | T1 | |
| 2269. | MeOCH₂CH₂ | i-Pr | H | H | Na | T1 | |
| 2270. | MeOCH₂CH₂ | i-Pr | H | H | H | T2 | |
| 2271. | MeOCH₂CH₂ | i-Pr | H | H | Na | T2 | |
| 2272. | MeOCH₂CH₂ | Allyl | H | H | H | T1 | |
| 2273. | MeOCH₂CH₂ | Allyl | H | H | Na | T1 | |
| 2274. | MeOCH₂CH₂ | Allyl | H | H | H | T2 | |
| 2275. | MeOCH₂CH₂ | Allyl | H | H | Na | T2 | |

TABLE 1-continued

Compounds of the formula (Ia)

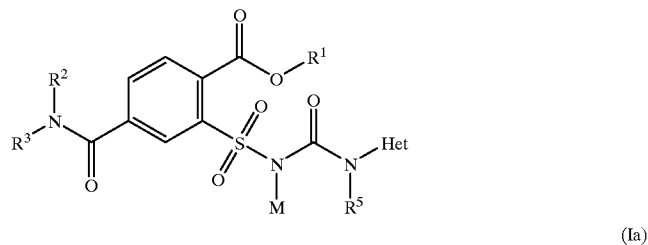

(Ia)

| Ex. | R¹ | R² | R³ | R⁵ | M | Het | m.p. |
|---|---|---|---|---|---|---|---|
| 2276. | MeOCH₂CH₂ | Allyl | Allyl | H | H | T1 | 107–109 |
| 2277. | MeOCH₂CH₂ | Allyl | Allyl | H | Na | T1 | 243–245 |
| 2278. | MeOCH₂CH₂ | Allyl | Allyl | H | H | T2 | |
| 2279. | MeOCH₂CH₂ | Allyl | Allyl | H | Na | T2 | |
| 2280. | MeOCH₂CH₂ | Me | Me | H | H | T1 | 103–106 |
| 2281. | MeOCH₂CH₂ | Me | Me | H | Na | T1 | 202–204 |
| 2282. | MeOCH₂CH₂ | Me | Me | H | H | T2 | |
| 2283. | MeOCH₂CH₂ | Me | Me | H | Na | T2 | |
| 2284. | ClCH₂CH₂ | H | H | H | H | T1 | 128–132 |
| 2285. | ClCH₂CH₂ | H | H | H | Na | T1 | 154–157 |
| 2286. | ClCH₂CH₂ | H | H | H | H | T2 | |
| 2287. | ClCH₂CH₂ | H | H | H | Na | T2 | |
| 2288. | ClCH₂CH₂ | Me | H | H | H | T1 | |
| 2289. | ClCH₂CH₂ | Me | H | H | Na | T1 | |
| 2290. | ClCH₂CH₂ | Me | H | H | H | T2 | |
| 2291. | ClCH₂CH₂ | Me | H | H | Na | T2 | |
| 2292. | ClCH₂CH₂ | Et | H | H | H | T1 | |
| 2293. | ClCH₂CH₂ | Et | H | H | Na | T1 | |
| 2294. | ClCH₂CH₂ | Et | H | H | H | T2 | |
| 2295. | ClCH₂CH₂ | Et | H | H | Na | T2 | |
| 2296. | ClCH₂CH₂ | i-Pr | H | H | H | T1 | |
| 2297. | ClCH₂CH₂ | i-Pr | H | H | Na | T1 | |
| 2298. | ClCH₂CH₂ | i-Pr | H | H | H | T2 | |
| 2299. | ClCH₂CH₂ | i-Pr | H | H | Na | T2 | |
| 2300. | ClCH₂CH₂ | Allyl | H | H | H | T1 | |
| 2301. | ClCH₂CH₂ | Allyl | H | H | Na | T1 | |
| 2302. | ClCH₂CH₂ | Allyl | H | H | H | T2 | |
| 2303. | ClCH₂CH₂ | Allyl | H | H | Na | T2 | |
| 2304. | ClCH₂CH₂ | Allyl | Allyl | H | H | T1 | 119–121 |
| 2305. | ClCH₂CH₂ | Allyl | Allyl | H | Na | T1 | 159–161 |
| 2306. | ClCH₂CH₂ | Allyl | Allyl | H | H | T2 | |
| 2307. | ClCH₂CH₂ | Allyl | Allyl | H | Na | T2 | |
| 2308. | ClCH₂CH₂ | Me | Me | H | H | T1 | |
| 2309. | ClCH₂CH₂ | Me | Me | H | Na | T1 | |
| 2310. | ClCH₂CH₂ | Me | Me | H | H | T2 | |
| 2311. | ClCH₂CH₂ | Me | Me | H | Na | T2 | |
| 2312. | Me | H | H | Me | H | T1 | |
| 2313. | Me | H | H | Me | Na | T1 | |
| 2314. | Me | H | H | Me | H | T2 | |
| 2315. | Me | H | H | Me | Na | T2 | |
| 2316. | Me | Me | H | Me | H | T1 | |
| 2317. | Me | Me | H | Me | Na | T1 | |
| 2318. | Me | Me | H | Me | H | T2 | |
| 2319. | Me | Me | H | Me | Na | T2 | |
| 2320. | Me | Et | H | Me | H | T1 | |
| 2321. | Me | Et | H | Me | Na | T1 | |
| 2322. | Me | Et | H | Me | H | T2 | |
| 2323. | Me | Et | H | Me | Na | T2 | |
| 2324. | Me | i-Pr | H | Me | H | T1 | |
| 2325. | Me | i-Pr | H | Me | Na | T1 | |
| 2326. | Me | i-Pr | H | Me | H | T2 | |
| 2327. | Me | i-Pr | H | Me | Na | T2 | |
| 2328. | Me | Allyl | H | Me | H | T1 | |
| 2329. | Me | Allyl | H | Me | Na | T1 | |
| 2330. | Me | Allyl | H | Me | H | T2 | |
| 2331. | Me | Allyl | H | Me | Na | T2 | |
| 2332. | Me | Me | Me | Me | H | T1 | |
| 2333. | Me | Me | Me | Me | Na | T1 | |
| 2334. | Me | Me | Me | Me | H | T2 | |
| 2335. | Me | Me | Me | Me | Na | T2 | |

TABLE 2

Compounds of the formula (Ib)

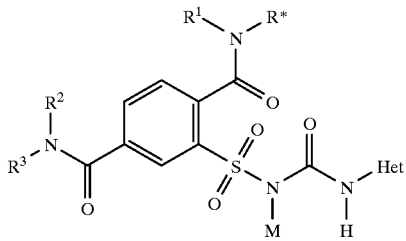

(Ib)

| Ex. No. | R¹ | R* | R² | R³ | M | Het | m.p. |
|---|---|---|---|---|---|---|---|
| 2-1 | Me | Me | H | H | H | T1 | 194–196(D) |
| 2-2 | Me | Me | H | H | Na | T1 | 233–235(D) |
| 2-3 | Me | Me | H | H | H | T2 | |
| 2-4 | Me | Me | H | H | Na | T2 | |
| 2-5 | Me | Me | Me | H | H | T1 | |
| 2-6 | Me | Me | Me | H | Na | T1 | |
| 2-7 | Me | Me | Me | H | H | T2 | |
| 2-8 | Me | Me | Me | H | Na | T2 | |
| 2-9 | Me | Me | Et | H | H | T1 | 113–115(D) |
| 2-10 | Me | Me | Et | H | Na | T1 | 196–198(D) |
| 2-11 | Me | Me | Et | H | H | T2 | |
| 2-12 | Me | Me | Et | H | Na | T2 | |
| 2-13 | Me | Me | i-Pr | H | H | T1 | |
| 2-14 | Me | Me | i-Pr | H | Na | T1 | |
| 2-15 | Me | Me | i-Pr | H | H | T2 | |
| 2-16 | Me | Me | i-Pr | H | Na | T2 | |
| 2-17 | Me | Me | Allyl | H | H | T1 | 114–116(D) |
| 2-18 | Me | Me | Allyl | H | Na | T1 | 202–204(D) |
| 2-19 | Me | Me | Allyl | H | H | T2 | |
| 2-20 | Me | Me | Allyl | H | Na | T2 | |
| 2-21 | Me | Me | Me | Me | H | T1 | |
| 2-22 | Me | Me | Me | Me | Na | T1 | |
| 2-23 | Me | Me | Me | Me | H | T2 | |
| 2-24 | Me | Me | Me | Me | Na | T2 | |
| 2-25 | H | H | Allyl | Allyl | H | T1 | 168–170(D) |
| 2-26 | H | H | Allyl | Allyl | Na | T1 | 224–226 |
| 2-27 | H | H | Allyl | Allyl | H | T2 | |
| 2-28 | H | H | Allyl | Allyl | Na | T2 | |
| 2-29 | Me | H | Allyl | Allyl | H | T1 | 181–183(D) |
| 2-30 | Me | H | Allyl | Allyl | Na | T1 | 197–199(D) |
| 2-31 | Me | H | Allyl | Allyl | H | T2 | |
| 2-32 | Me | H | Allyl | Allyl | Na | T2 | |
| 2-33 | Me | Me | Allyl | Allyl | H | T1 | 147–149(D) |
| 2-34 | Me | Me | Allyl | Allyl | Na | T1 | 142–144(D) |
| 2-35 | Me | Me | Allyl | Allyl | H | T2 | |
| 2-36 | Me | Me | Allyl | Allyl | Na | T2 | |
| 2-37 | Et | H | Allyl | Allyl | H | T1 | 189–191(D) |
| 2-38 | Et | H | Allyl | Allyl | Na | T1 | 145–147 |
| 2-39 | Et | H | Allyl | Allyl | H | T2 | |
| 2-40 | Et | H | Allyl | Allyl | Na | T2 | |
| 2-41 | Me | H | H | H | H | T1 | |
| 2-42 | Me | H | H | H | Na | T1 | |
| 2-43 | Me | H | H | H | H | T2 | |
| 2-44 | Me | H | H | H | Na | T2 | |
| 2-45 | Et | H | Me | H | H | T1 | |
| 2-46 | Et | H | Me | H | Na | T1 | |
| 2-47 | Et | H | Me | H | H | T2 | |
| 2-48 | Et | H | Me | H | Na | T2 | |
| 2-49 | Et | Me | Allyl | H | H | T1 | |
| 2-50 | Et | Me | Allyl | H | Na | T1 | |
| 2-51 | Et | Me | Allyl | H | H | T2 | |
| 2-52 | Et | Me | Allyl | H | Na | T2 | |
| 2-53 | Et | Et | i-Pr | H | H | T1 | |
| 2-54 | Et | Et | i-Pr | H | Na | T1 | |
| 2-55 | Et | Et | i-Pr | H | H | T2 | |
| 2-56 | Et | Et | i-Pr | H | Na | T2 | |
| 2-57 | Allyl | H | Me | Me | H | T1 | |
| 2-58 | Allyl | H | Me | Me | Na | T1 | |
| 2-59 | Allyl | H | Me | Me | H | T2 | |
| 2-60 | Allyl | H | Me | Me | Na | T2 | |
| 2-61 | Allyl | Allyl | Et | H | H | T1 | |
| 2-61 | Allyl | Allyl | Et | H | Na | T1 | |
| 2-63 | Allyl | Allyl | Et | H | H | T2 | |
| 2-64 | Allyl | Allyl | Et | H | Na | T2 | |
| 2-65 | Propargyl | H | H | H | H | T1 | |
| 2-66 | Propargyl | H | H | H | Na | T1 | |
| 2-67 | Propargyl | H | H | H | H | T2 | |
| 2-68 | Propargyl | H | H | H | Na | T2 | |
| 2-69 | MeOCH₂CH₂ | H | Me | H | H | T1 | |
| 2-70 | MeOCH₂CH₂ | H | Me | H | Na | T1 | |
| 2-71 | MeOCH₂CH₂ | H | Me | H | H | T2 | |
| 2-72 | MeOCH₂CH₂ | H | Me | H | Na | T2 | |
| 2-73 | ClCH₂CH₂ | H | Me | Me | H | T1 | |
| 2-74 | ClCH₂CH₂ | H | Me | Me | Na | T1 | |
| 2-75 | ClCH₂CH₂ | H | Me | Me | H | T2 | |
| 2-76 | ClCH₂CH₂ | H | Me | Me | Na | T2 | |

B. FORMULATION EXAMPLES a) A dust is obtained by mixing 10 parts by weight of a compound of the formula (I) and 90 parts by weight of talc as inert substance and comminuting the mixture in a hammer mill.

b) A wettable powder which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurinate as wetter and dispersant and grinding the mixture in a pinned-disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example approx. 255 to above 277° C.) and grinding the mixture in a ball mill to a fineness of below 5 microns.

d) An emulsifiable concentrate is obtained from 15 parts by weight of a compound of the formula (I), 75 parts by weight of cyclohexanone as the solvent and 10 parts by weight of ethoxylated nonylphenol as the emulsifier.

e) Water-dispersible granules are obtained by mixing 75 parts by weight of a compound of the formula (I), 10 parts by weight of calcium lignosulfonate, 5 parts by weight of sodium lauryl sulfate, 3 parts by weight of polyvinyl alcohol and 7 parts by weight of kaolin, grinding the mixture on a pinned-disk mill and granulating the powder in a fluidized bed by spraying on water as the granulation liquid.

f) Water-dispersible granules are also obtained by homogenizing and precomminuting, on a colloid mill,
   25 parts by weight of a compound of the formula (I),
   5 parts by weight of sodium 2,2'-dinaphthylmethane-6,6'-disulfonate
   2 parts by weight of sodium oleoylmethyltaurinate,
   1 part by weight of polyvinyl alcohol,
   17 parts by weight of calcium carbonate and
   50 parts by weight of water,
   subsequently grinding the mixture in a bead mill and atomizing and drying the resulting suspension in a spray tower by means of a single-substance nozzle.

C. BIOLOGICAL EXAMPLES

1. Pre-Emergence Effect on Weeds

Seeds or rhizome pieces of monocotyledonous and dicotyledonous weed plants were placed in sandy loam soil in cardboard pots and covered with soil. The compounds according to the invention which were formulated in the form of wettable powders or emulsion concentrates were then applied to the surface of the soil cover in the form of aqueous suspensions or emulsions at an application rate of 600 to 800 l of water/ha (converted), in various dosages.

After the treatment, the pots were placed in a greenhouse and kept under good growth conditions for the weeds. After the test plants had emerged, the damage to the plants or the negative effects on the emergence was scored visually after a test period of 3 to 4 weeks by comparison with untreated controls. As shown by the test results, the compounds according to the invention have a good herbicidal pre-emergence activity against a broad spectrum of grass weeds and dicotyledonous weeds. For example, the compounds of Examples No. 1, 2, 3, 4, 11, 12, 13, 14, 31, 32, 33, 34, 41, 42, 43, 44, 61, 62, 63, 64, 71, 72, 91, 92, 93, 94, 101, 102, 103, 104, 121, 122, 123, 124, 131, 132, 133, 134, 151, 152, 271, 272, 273, 274, 301, 302, 331, 361, 362, 391, 392, 405, 406, 435, 436, 449, 450, 479, 480, 499, 500, 529, 539, 749, 769, 770, 839, 840, 859, 860, 889, 890, 1289, 1290, 1559, 1560, 1561, 1562, 1565, 1566, 1567, 1568, 1569, 1570, 1579, 1599, 1600, 1609, 1619, 1620, 1629, 1630, 1739, 1740, 1749, 1750, 1759, 1760, 1779, 1780, 1799, 1800, 1809, 1810, 1819, 1839, 1840, 1859, 1860, 1869, 1870, 1909, 1910, 1989, 1990, 2003, 2004, 2031, 2043, 2044, 2063, 2064, 2075, 2076, 2087, 2088, 2095, 2103, 2115, 2119, 2120, 2123, 2131, 2132, 2135, 2136, 2139, 2140, 2143, 2167, 2168, 2171, 2172, 2175, 2176, 2179, 2180, 2183, 2184, 2187, 2188, 2192, 2199, 2219, 2227, 2228, 2247, 2251, 2253, 2256, 2276, 2277, 2280, 2281, 2284, 2285, 2304, 2305, 2-1, 2-2, 2-9, 2-10, 2-17, 2-18, 2-25, 2-26, 2-29, 2-30, 2-33, 2-34, 2-37, 2-38 and other compounds of Tables 1 and 2 have a very good herbicidal activity against harmful plants such as *Sinapis alba, Chrysanthemum segetum, Avena sativa, Stellaria media, Echinochloa crus-galli, Lolium multiflorum*, Setaria spp., *Abutilon theophrasti, Amaranthus retroflexus* and *Panicum miliaceum*, pre-emergence at an application rate of 0.3 kg and less of active substance per hectare.

2. Post-Emergence Effect on Weeds

Seeds or rhizome pieces of monocotyledonous and dicotyledonous weeds were placed in sandy loam soil in plastic pots, covered with soil and grown in a greenhouse under good growth conditions. Three weeks after sowing, the test plants were treated at the three-leaf stage. The compounds according to the invention which were formulated as wettable powders or emulsion concentrates were sprayed, at various dosages, onto the green parts of the plants at an application rate of 600 to 800 l of water/ha (converted). After the test plants had remained in the greenhouse for about 3 to 4 weeks under ideal growth conditions, the effect of the preparations was scored visually by comparison with untreated controls. The agents according to the invention also have a good herbicidal activity post-emergence against a broad spectrum of economically important grass weeds and dicotyledonous weeds. For example, the compounds of Examples No. 1, 2, 3, 4, 11, 12, 13, 14, 31, 32, 33, 34, 41, 42, 43, 44, 61, 62, 63, 64, 71, 72, 91, 92, 93, 94, 101, 102, 103, 104, 121, 122, 123, 124, 131, 132, 133, 134, 151, 152, 271, 272, 273, 274, 301, 302, 331, 361, 362, 391, 392, 405, 406, 435, 436, 449, 450, 479, 480, 499, 500, 529, 539, 749, 769, 770, 839, 840, 859, 860, 889, 890, 1289, 1290, 1559, 1560, 1561, 1562, 1565, 1566, 1567, 1568, 1569, 1570, 1579, 1599, 1600, 1609, 1619, 1620, 1629, 1630, 1739, 1740, 1749, 1750, 1759, 1760, 1779, 1780, 1799, 1800, 1809, 1810, 1819, 1839, 1840, 1859, 1860, 1869, 1870, 1909, 1910, 1989, 1990, 2003, 2004, 2031, 2043, 2044, 2063, 2064, 2075, 2076, 2087, 2088, 2095, 2103, 2115, 2119, 2120, 2123, 2131, 2132, 2135, 2136, 2139, 2140, 2143, 2167, 2168, 2171, 2172, 2175, 2176, 2179, 2180, 2183, 2184, 2187, 2188, 2192, 2199, 2219, 2227, 2228, 2247, 2251, 2253, 2256, 2276, 2277, 2280, 2281, 2284, 2285, 2304, 2305, 2-1, 2-2, 2-9, 2-10, 2-17, 2-18, 2-25, 2-26, 2-29, 2-30, 2-33, 2-34, 2-37, 2-38 and other compounds of the Tables 1 and 2 have a very good herbicidal activity against harmful plants such as *Sinapis alba, Echinochloa crus-galli, Lolium multiflorum, Chrysanthemum segetum*, Setaria spp., *Abutilon theophrasti, Amaranthus retroflexus, Panicum miliaceum* and *Avena sativa* post-emergence at an application rate of 0.3 kg and less of active substance per hectare.

3. Tolerance by Crop Plants

In further greenhouse experiments, seeds of a substantial number of crop plants and weeds were placed in sandy loam soil and covered with soil. Some of the pots were treated immediately as described under Section 1, and the remaining pots were placed in a greenhouse until the plants had developed two to three true leaves and then sprayed with various dosages of the substances of the formula (I) according to the invention, as described under Section 2.

Visual scoring four to five weeks after the application and after the plants had been in the greenhouse revealed that the compounds according to the invention did not inflict any damage to Gramineae crops such as, for example, barley, wheat, rye, sorghum species, corn or rice when used pre- and post-emergence, even when high dosages of active ingredient were used. Moreover, some substances also left dicotyledonous crops such as, for example, soya, cotton, oil seed rape, sugar beet and potatos unharmed. Some of the compounds of the formula (I) have a high selectivity, and they are therefore suitable for controlling undesired plant growth in agricultural crops.

What is claimed is:

1. A compound of the formula (I) or a salt thereof

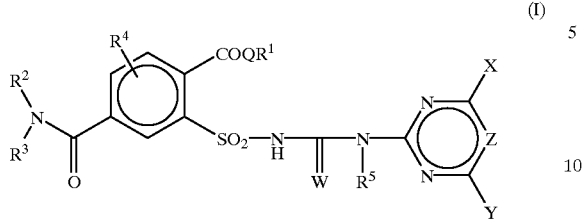

(I)

in which

R¹ is a hydrogen atom, a hydrocarbon radical or a heterocyclyl radical, where each of the two last mentioned radicals is unsubstituted or substituted and has, including substituents, 1 to 30 carbon atoms, R² is a group of the formula R⁰—Q⁰—, in which R⁰ is a hydrogen atom, a hydrocarbon radical or a heterocyclyl radical, where each of the two last mentioned radicals is unsubstituted or substituted and has, including substituents, 1 to 30 carbon atoms, and Q⁰ is a direct bond or a divalent group of the formula —O—, —SO²—, —NH—, —N[(C₁–C₆)alkyl]-, —CO—, —CO—NH— or —O—CO—NH—, R³ is a hydrogen atom, a hydrocarbon radical or a heterocyclyl radical, where each of the two last mentioned radicals is unsubstituted or substituted and has, including substituents, 1 to 30 carbon atoms, R⁴ is H, halogen, NO₂, CN, (C₁–C₄)alkyl, (C₁–C₄)alkoxy, [(C₁–C₄)alkyl]-carbonyl or [(C₁–C₄)alkoxy]carbonyl, where each of the four last mentioned radicals is unsubstituted or substituted in the alkyl moiety by one or more halogen atoms, R⁵ is H or (C₁–C₄)alkyl, Q is O or NR*, R* is H, (C₁–C₄)alkyl, (C₃–C₄)alkenyl or (C₃–C₄) alkynyl, where each of the three last mentioned radicals is unsubstituted or substituted by one or more radicals selected from the group consisting of halogen, (C₁–C₄) alkoxy and (C₁–C₄)alkylthio, W is an oxygen or sulfur atom, X,Y independently of one another are H, halogen, (C₁–C₄)alkyl, (C₁–C₄)alkoxy, (C₁–C₄)alkylthio, where each of the three last mentioned radicals is unsubstituted or substituted by one or more radicals selected from the group consisting of halogen, (C₁–C₄)alkoxy and (C₁–C₄)alkylthio, or are mono- or di[(C₁–C₄)alkyl] amino, (C₃–C₄)cycloalkyl, (C₂–C₅)alkenyl, (C₂–C₅) alkynyl, (C₂–C₅)alkenyloxy or (C₂–C₅)alkynyloxy and Z is CH.

2. The compound or a salt thereof as claimed in claim 1, wherein

R¹ is H, (C₁–C₆)alkyl, (C₃–C₆)alkenyl, (C₃–C₆)alkynyl, where each of the three last mentioned radicals is unsubstituted or substituted by one or more radicals selected from the group consisting of halogen, unsubstituted and substituted phenyl, unsubstituted and substituted heterocyclyl having 3 to 6 ring atoms, unsubstituted and substituted (C₃–C₆)cycloalkyl, (C₁–C₄) alkoxy, (C₁–C₄)alkylthio, [(C₁–C₄)alkoxy]carbonyl and [(C₁–C₄)haloalkoxy]carbonyl, or is unsubstituted or substituted (C₃–C₆)cycloalkyl, unsubstituted or substituted phenyl, unsubstituted or substituted heterocyclyl having 3 to 6 ring atoms and R² is a group of the formula R⁰—Q⁰—, in which R⁰ is a hydrogen atom, (C₁–C₁₂)alkyl, (C₃–C₁₂)alkenyl or (C₃–C₁₂)alkynyl, where each of the three last mentioned radicals is unsubstituted or substituted by one or more radicals selected from the group consisting of halogen, (C₁–C₆)alkoxy, (C₁–C₆)haloalkoxy, (C₁–C₆)alkylthio, (C₁–C₆) haloalkylthio, (C₁–C₆)alkylsulfinyl, (C₁–C₆) haloalkylsulfinyl, (C₁–C₆)alkylsulfonyl, (C₁–C₆) haloalkylsulfonyl, [(C₁–C₆)alkoxy]carbonyl, [(C₁–C₆)haloalkoxy]carbonyl, CONR⁶R⁷, SO₂NR⁶R⁷, CN, OH, (C₃–C₆)cycloalkyl, NR⁸R⁹, unsubstituted phenyl, substituted phenyl, unsubstituted heterocyclyl and substituted heterocyclyl, or is unsubstituted or substituted (C₃–C₆)cycloalkyl, unsubstituted or substituted (C₃–C₆)cycloalkenyl, unsubstituted or substituted heterocyclyl or unsubstituted or substituted phenyl and in which Q⁰ is a direct bond or a divalent group of the formula —O—, —SO₂—, —NH—, —N[(C₁–C₈)alkyl]-, —CO—, —CO—NH— or —O—CO—NH—, R³ independently of one another are defined as R⁰ in the radical R², or R² and R³ together with the nitrogen atom are a heterocycle of 3–6 ring atoms which is saturated or unsaturated, which may, in addition to the nitrogen atom, contain one or two atoms selected from the group consisting of N, O and S and which is unsubstituted or substituted by one or more radicals selected from the group consisting of (C₁–C₆)alkyl, (C₁–C₆)alkoxy, halogen, [(C₁–C₆)alkoxy]carbonyl, (C₁–C₆)haloalkyl and oxo, and R⁶ and R⁷ independently of one another are H, (C₁–C₆) alkyl, (C₃–C₆)alkenyl, (C₃–C₆)alkynyl or unsubstituted or substituted phenyl or R⁶ and R⁷ together with the nitrogen atom are a heterocyclic ring having 5 or 6 ring members which may optionally contain further heteroatoms selected from the group consisting of N, O and S and which is unsubstituted or mono- or polysubstituted by radicals selected from the group consisting of (C₁–C₄)alkyl and oxo, and R⁸ and R⁹ independently of one another and independently of R⁶ and R⁷ are as defined under R⁶ and R⁷ or are (C₁–C₄)alkylcarbonyl, (C₁–C₄)haloalkylcarbonyl, (C₁–C₄)-alkoxycarbonyl or (C₁–C₄)alkylsulfonyl, Q is O or NR*, where R* is as defined above, X and Y independently of one another are H, halogen, (C₁–C₄)alkyl, (C₁–C₄)alkoxy, (C₁–C₄)alkylthio, where each of the three last mentioned radicals is unsubstituted or substituted by one or more radicals selected from the group consisting of halogen, (C₁–C₃)alkoxy and (C₁–C₄)alkylthio, are mono- or di[(C₁–C₄)alkyl] amino, (C₃–C₆)cycloalkyl, (C₃–C₅)alkenyl, (C₃–C₅) alkenyloxy or (C₃–C₅)alkynyloxy and Z is CH, where substituted phenyl, substituted heterocyclyl, substituted cycloalkyl or substituted cycloalkenyl carries one or more radicals selected from the group consisting of halogen, (C₁–C₄)alkyl, (C₁–C₄)haloalkyl, (C₁–C₄) alkoxy-(C₁–C₄)alkyl, di[(C₁–C₄)alkoxy]-(C₁–C₄) alkyl, (C₁–C₄)haloalkoxy, (C₁–C₄)alkylthio, (C₁–C₄) alkylsulfinyl, (C₁–C₄)haloalkylsulfinyl, (C₁–C₄)

alkylsulfonyl, $(C_1$–$C_4)$haloalkylsulfonyl, $NR^8R^9$, [$(C_1$–$C_4)$alkoxy]carbonyl, [$(C_1$–$C_4)$haloalkoxy] carbonyl, [$(C_1$–$C_4)$alkyl]carbonyl, OH, phenyl, CN and $NO_2$ as substituents and where each of the radicals $R^1$, $R^2$ and $R^3$ has, including substituents, 1 to 20 carbon atoms.

3. The compound or a salt thereof as claimed in claim 1, wherein $R^1$ is H, $(C_1$–$C_6)$alkyl, $(C_3$–$C_6)$alkenyl or $(C_3$–$C_6)$alkynyl, where each of the three last mentioned radicals is unsubstituted or substituted by one or more radicals selected from the group consisting of halogen, phenyl, $(C_1$–$C_4)$alkoxy, $(C_1$–$C_4)$alkylthio and [$(C_1$–$C_4)$alkoxy]carbonyl or is $(C_3$–$C_8)$cycloalkyl, $(C_3$–$C_6)$cycloalkyl $(C_1$–$C_3)$alkyl, heterocyclyl having 3 to 6 ring atoms or heterocyclyl-$(C_1$–$C_3)$alkyl having 3 to 6 ring atoms, where each of the four last mentioned radicals is unsubstituted or substituted by one or more radicals selected from the group consisting of halogen, $(C_1$–$C_4)$ alkyl and $(C_1$–$C_4)$alkoxy, $R^2$ is a group of the formula $R^0$—$Q^0$—, in which $R^0$ is a hydrogen atom, $(C_1$–$C_8)$alkyl, $(C_3$–$C_8)$alkenyl or $(C_3$–$C_8)$alkynyl, where each of the three last mentioned radicals is unsubstituted or substituted by one or more radicals selected from the group consisting of halogen, $(C_1$–$C_4)$alkoxy, $(C_1$–$C_4)$ haloalkoxy, $(C_1$–$C_4)$alkylthio, $(C_1$–$C_4)$haloalkylthio, $(C_1$–$C_4)$alkylsulfinyl, $(C_1$–$C_4)$haloalkylsulfinyl, $(C_1$–$C_4)$alkylsulfonyl, $(C_1$–$C_4)$haloalkylsulfonyl, [$(C_1$–$C_6)$alkoxy]carbonyl, $CONR^6R^7$, $SO_2NR^6R^7$, CN, OH, $(C_3$–$C_6)$cycloalkyl, $NR^8R^9$, phenyl, which is unsubstituted or substituted by one or more radicals selected from the group consisting of halogen, $(C_1$–$C_4)$alkyl, $(C_1$–$C_4)$haloalkyl, $(C_1$–$C_4)$alkoxy, $(C_1$–$C_4)$haloalkoxy, $(C_1$–$C_4)$alkylthio, $(C_1$–$C_4)$ alkylsulfinyl, $(C_1$–$C_4)$alkylsufonyl, $NR^8R^9$, [$(C_1$–$C_4)$alkoxy]carbonyl, [$(C_1$–$C_4)$alkyl]carbonyl, phenyl, [$(C_1$–$C_4)$alkyl]carbonyl, CN and $NO_2$ and heterocyclyl which is unsubstituted or substituted by one or more radicals selected from the group consisting of halogen, $(C_1$–$C_4)$alkyl, $(C_1$–$C_4)$haloalkyl, $(C_1$–$C_4)$alkoxy, $(C_1$–$C_4)$haloalkoxy, $(C_1$–$C_4)$ alkylthio, $(C_1$–$C_4)$alkylsulfinyl, $(C_1$–$C_4)$ alkylsulfonyl, $NR^8R^9$, [$(C_1$–$C_4)$alkoxy]carbonyl, [$(C_1$–$C_4)$alkyl]carbonyl, phenyl, [$(C_1$–$C_4)$alkyl] carbonyl, CN and $NO_2$, or is $(C_3$–$C_6)$cycloalkyl, which is unsubstituted or substituted by one or more radicals selected from the group consisting of halogen, $(C_1$–$C_4)$alkyl, $(C_1$–$C_4)$haloalkyl, $(C_1$–$C_4)$ alkoxy, $(C_1$–$C_4)$haloalkoxy, [$(C_1$–$C_4)$alkoxy] carbonyl, CN, OH and phenyl, or is $(C_3$–$C_6)$ cycloalkenyl, which is unsubstituted or substituted by one or more radicals selected from the group consisting of halogen, $(C_1$–$C_4)$alkyl, $(C_1$–$C_4)$ haloalkyl, $(C_1$–$C_4)$alkoxy and [$(C_1$–$C_4)$alkoxy] carbonyl, or is heterocyclyl or phenyl, where each of the two last mentioned radicals is unsubstituted or substituted by one or more radicals selected from the group consisting of halogen, $(C_1$–$C_4)$alkyl, $(C_1$–$C_4)$ haloalkyl, $(C_1$–$C_4)$alkoxy, $(C_1$–$C_4)$haloalkoxy, $(C_1$–$C_4)$alkylthio, $(C_1$–$C_4)$alkylsulfinyl, $(C_1$–$C_4)$ alkylsufonyl, $NR^8R^9$, [$(C_1$–$C_4)$alkoxy]carbonyl, [$(C_1$–$C_4)$alkyl]carbonyl, phenyl, [$(C_1$–$C_4)$alkyl] carbonyl, CN and $NO_2$, and $Q^0$ is a direct bond or a divalent group of the formula —O—, —$SO_2$—, —NH—, —CO—NH— or —O—CO—NH—, $R^3$ independently of one another is defined as $R^0$ in the radical $R^2$, $R^2$ and $R^3$ together with the nitrogen atom are a heterocycle of 3–6 ring atoms which is saturated or unsaturated and which may, in addition to the nitrogen atom, contain one or two heteroatoms selected from the group consisting of N, O and S and which is unsubstituted or substituted by one or more radicals selected from the group consisting of $(C_1$–$C_3)$alkyl, $(C_1$–$C_3)$alkoxy, halogen, [$(C_1$–$C_3)$alkoxy]carbonyl, $(C_1$–$C_3)$haloalkyl and oxo, $R^6$ and $R^7$ independently of one another represent H, $(C_1$–$C_4)$alkyl, $(C_3$–$C_4)$alkenyl, $(C_3$–$C_4)$alkynyl or phenyl, which is unsubstituted or substituted by one or more radicals selected from the group consisting of halogen, $(C_1$–$C_4)$alkyl, $(C_1$–$C_4)$haloalkyl, $(C_1$–$C_4)$ alkoxy, $(C_1$–$C_4)$alkylthio, $(C_1$–$C_4)$alkylsulfonyl, [$(C_1$–$C_4)$alkoxy]carbonyl, CN and $NO_2$, or $R^6$ and $R^7$ together with the nitrogen atom are a heterocyclic ring having 5 or 6 ring members which may optionally contain other heteroatoms selected from the group consisting of N, O and S and which is unsubstituted or mono- or polysubstituted by radicals selected from the group consisting of $(C_1$–$C_4)$ alkyl and oxo, $R^8$ and $R^9$ independently of one another and independently of $R^6$ and $R^7$ are as defined under $R^6$ and $R^7$ or are $(C_1$–$C_4)$alkylcarbonyl, $(C_1$–$C_4)$haloalkylcarbonyl, $(C_1$–$C_4)$-alkoxycarbonyl or $(C_1$–$C_4)$alkylsulfonyl, Q is O or NR*, where R* is as defined further above, X and Y independently of one another are H, halogen, $(C_1$–$C_4)$alkyl, $(C_1$–$C_4)$alkoxy, $(C_1$–$C_4)$alkylthio, where each of the three last mentioned radicals is unsubstituted or substituted by one or more radicals selected from the group consisting of halogen, $(C_1$–$C_3)$alkoxy and $(C_1$–$C_4)$alkylthio, are mono- or di[$(C_1$–$C_4)$alkyl] amino, $(C_3$–$C_6)$cycloalkyl, $(C_3$–$C_5)$alkenyl, $(C_3$–$C_5)$ alkenyloxy or $(C_3$–$C_5)$alkynyloxy and Z is CH.

4. The compound or a salt thereof as claimed in claim 1, wherein $R^1$ is $(C_1$–$C_6)$alkyl, which is unsubstituted or substituted by one or more radicals selected from the group consisting of halogen and $(C_1$–$C_4)$alkoxy, or is 3-oxetanyl, $(C_3$–$C_4)$alkenyl or $(C_3$–$C_4)$alkynyl, $R^2$ is H, $(C_1$–$C_6)$alkyl, $(C_3$–$C_6)$alkenyl, $(C_3$–$C_6)$alkynyl, where each of the three last mentioned radicals is unsubstituted or substituted by one or more radicals selected from the group consisting of halogen, $(C_1$–$C_4)$ alkoxy, $(C_1$–$C_4)$alkylthio, $(C_1$–$C_4)$alkylsulfonyl, [$(C_1$–$C_4)$alkoxy]carbonyl, $(C_3$–$C_6)$cycloalkyl, CN and OH, or is $(C_3$–$C_6)$cycloalkyl, which is unsubstituted or substituted by one or more radicals selected from the group consisting of halogen, $(C_1$–$C_4)$alkyl, $(C_1$–$C_4)$ alkoxy, [$(C_1$–$C_4)$alkoxy]carbonyl, CN and OH, or is $(C_3$–$C_6)$cycloalkenyl, $(C_1$–$C_4)$alkoxy, $(C_1$–$C_4)$ alkenyloxy, $(C_1$–$C_4)$alkylsulfonyl, $(C_1$–$C_4)$alkylamino or di[$(C_1$–$C_4)$alkyl]amino and $R^3$ is H, $(C_1$–$C_6)$alkyl, $(C_3$–$C_6)$alkenyl, $(C_3$–$C_6)$alkynyl, where each of the three last mentioned radicals is unsubstituted or substituted by one or more radicals selected from the group consisting of halogen, $(C_1$–$C_4)$ alkoxy, $(C_1$–$C_4)$alkylthio, $(C_1$–$C_4)$alkylsulfonyl, [$(C_1$–$C_4)$alkoxy]carbonyl, $(C_3$–$C_6)$cycloalkyl, CN and OH, or is $(C_3$–$C_6)$cycloalkyl, which is unsubstituted or substituted by one or more radicals selected from the group consisting of halogen, $(C_1-C_4)$alkyl, $(C_1-C_4)$alkoxy, $[(C_1-C_4)$alkoxy]carbonyl, CN and OH, or is $(C_3-C_6)$cycloalkenyl or $R^2$ and $R^3$ together with the nitrogen atom are a heterocycle of 3–6 ring atoms which is saturated or unsaturated, which may, in addition to the nitrogen atom, contain one or two atoms selected from the group consisting of N, O and S and which is unsubstituted or substituted by one or more radicals selected from the group consisting of halogen, $(C_1-C_3)$alkyl, $(C_1-C_3)$alkoxy, oxo and $[(C_1-C_3)$alkoxy]carbonyl, and $R^4$ is H, $(C_1-C_4)$alkyl, $(C_1-C_4)$haloalkyl, $(C_1-C_4)$alkoxy or halogen, $R^5$ is H or methyl, $R^*$ is H or $(C_1-C_4)$alkyl, X and Y independently of one another are $(C_1-C_4)$alkyl, $(C_1-C_4)$alkoxy, where each of the two last mentioned radicals is unsubstituted or substituted by one or more halogen atoms, or are $(C_1-C_4)$alkylthio, halogen or mono- or di[$(C_1-C_2)$alkyl]amino and W is an oxygen atom.

5. The compound or a salt thereof as claimed in claim 1, wherein $R^1$ is $(C_1-C_3)$alkyl, allyl or propargyl, $R^2$ and $R^3$ independently of one another are H, $(C_1-C_4)$alkyl, $(C_1-C_3)$alkenyl, $(C_1-C_3)$alkynyl, $(C_1-C_3)$cycloalkyl or $(C_3-C_6)$cycloalkenyl, $R^4$ is H, $(C_1-C_3)$alkyl or halogen, $R^*$ is $(C_1-C_3)$alkyl, X is $(C_1-C_2)$alkyl, $(C_1-C_2)$alkoxy, $(C_1-C_2)$alkylthio, $(C_1-C_2)$haloalkyl or $(C_1-C_2)$haloalkoxy and Y is $(C_1-C_2)$alkyl, $(C_1-C_2)$alkoxy, halogen, $NHCH_3$ or $N(CH_3)_2$.

6. A process for preparing compounds of the formula (I) or salts thereof as defined in claim 1, which comprises a) reacting a compound of the formula (II)

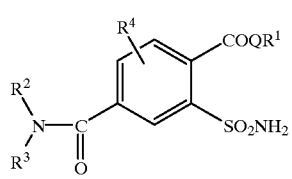

(II)

with a heterocyclic carbamate of the formula (III),

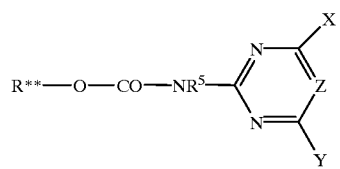

(III)

in which $R^{**}$ is optionally substituted aryl or an aliphatic radical, or b) reacting a sulfonylcarbamate of the formula (IV)

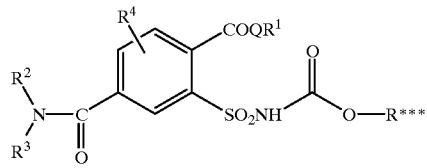

(IV)

in which $R^{***}$ is optionally substituted phenyl or $(C_1-C_4)$alkyl with an amino heterocycle of the formula (V)

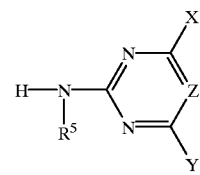

(V)

or c) reacting a sulfonyl isocyanate of the formula (VI)

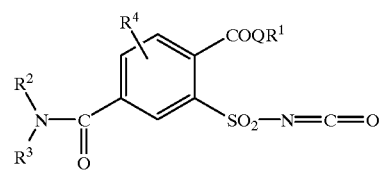

(VI)

with an amino heterocycle of the formula (V) or d) reacting a sulfonamide of the formula (II) with a (thio)isocyanate of the formula (VII)

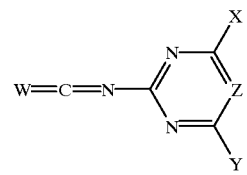

(VII)

in the presence of a base or e) reacting an amino heterocycle of the formula (V) initially under base-catalysis with a carbonate, for example diphenyl carbonate, and reacting the intermediate formed in a one-pot reaction with a sulfonamide of the formula (II) (see variant a), where in the formulae (II)–(VII) the radicals or groups $R^1-R^5$, W, X, Y and Z are as defined in formula (I) and in process variants a) to c) and e), initially compounds (I) where W=O are obtained.

7. A herbicidal or plant-growth-regulating composition, which comprises at least one compound of the formula (I) or a salt thereof as claimed in claim 1 and formulation auxiliaries which are customary in crop protection.

8. A method for controlling harmful plants or for regulating the growth of plants, which comprises applying an effective amount of at least one compound of the formula (I)

or a salt thereof as claimed in claim 1 onto the harmful plants or plants, their plant seeds or the area on which they grow.

9. A method for controlling harmful plants or for regulating the growth in crops of useful plants or ornamentals, which comprises applying an effective amount of a compound of the formula I or salts therefor, as claimed in claim 1, onto the harmful plants or plants ornamentals, their seeds or the area on which they grow.

10. The method of claim 9, wherein the crop plants are transgenic plants.

* * * * *